United States Patent
Wei et al.

(10) Patent No.: US 6,461,843 B1
(45) Date of Patent: Oct. 8, 2002

(54) ISOLATED NUCLEIC ACID MOLECULES ENCODING HUMAN ENZYME PROTEINS, AND USES THEREOF

(75) Inventors: Ming-Hui Wei, Germantown; Jane Ye, Boyds; Karen A. Ketchum, Germantown; Valentina Di Francesco, Rockville; Ellen M. Beasley, Darnestown, all of MD (US)

(73) Assignee: Applera Corporation, Norwalk, CT (US)

( * ) Notice: Subject to any disclaimer, the term of this patent is extended or adjusted under 35 U.S.C. 154(b) by 0 days.

(21) Appl. No.: 09/784,316

(22) Filed: Feb. 16, 2001

(51) Int. Cl.[7] ............................. C12N 9/10; C12N 5/10; C12N 15/79; C07H 21/04; C12Q 1/48

(52) U.S. Cl. ................ 435/193; 536/23.2; 435/15; 435/69.1; 435/325; 435/252.3; 435/320.1

(58) Field of Search ..................... 536/23.2; 435/193, 435/15, 69.1, 325, 252.3, 320.1

(56) References Cited

PUBLICATIONS

Bork, Genome Research, 10:348–400, 2000.*
Broun et al., Science 282:1315–1317, 1998.*
Brenner, TIG 15:132–1333, 1999.*
Smith et al., Nature Biotechnology 15:1222–1223, 1997.*
Van de Loo et al., Proc. Natl. Acad. Sci. 92:6743–6747, 1995.*
Wieland et al., Oncogene 18:4530–4537, 1999; SPTREMBL accesion No. Q9UL03, May 2000.*

* cited by examiner

*Primary Examiner*—Ponnathapu Achutamurthy
*Assistant Examiner*—Delia Ramirez
(74) *Attorney, Agent, or Firm*—Applera Corporation; Justin D. Karjala

(57) ABSTRACT

The present invention provides amino acid sequences of peptides that are encoded by genes within the human genome, the enzyme peptides of the present invention. The present invention specifically provides isolated peptide and nucleic acid molecules, methods of identifying orthologs and paralogs of the enzyme peptides, and methods of identifying modulators of the enzyme peptides.

9 Claims, 33 Drawing Sheets

```
   1 CGCTCTAGTG AGCGCGGACG GATGCTTAGG CAGTAGTCCT GGCAGCGGCA
  51 GTAGTGGTGG CAGCAGAAGA GAGGAAGGGG GAGGGCCCCG AGGGCTACAC
 101 ACGCTCACAC TTTCAAGTTC CCTTGGAGGG AGAGGAGGTG GGGCTGCAGA
 151 AAGAGGAGGC CAGGAGCGGT CCCATCCGTC CCGTCCCGTC CCGTCTCCCC
 201 CTCTTCCTCT TGCTCCTTGC CCCCGGCTC TGCGAGAGTT GAGGGTTCAG
 251 GTGGCCGTAC GCGGCAGTGA GGGCAAGAGG GCCGGGAGAG TGGGGAGCGG
 301 AGGCAGGAGT GCGGGGGAAG ATGCCCATCC TGCTGTTCCT CATAGACACG
 351 TCCGCCTCTA TGAACCAGCG CACTGACCTG GCACCTCTT ATTTGGACAT
 401 TGCCAAAGGC GCTGTGGAGT TATTCTTGAA GCTGCGCGCC CGGGACCCGG
 451 CCAGCCGTGG AGACAGGTAC ATGCTGGTCA CCTACGACGA ACCCCGTAC
 501 TGCATCAAGG CTGGTTGGAA GGAAAATCAT GCAACATTCA TGAGCGAACT
 551 AAAAAATCTT CAGGCTTCTG GACTGACTAC TCTCGGTCAG GCTCTAAGAT
 601 CCTCATTTGA TTTGTTAAAT CTCAATAGAT TAATATCTGG AATAGACAAT
 651 TATGGACAGG GGAGAAATCC ATTTTTTTTA GAACCATCTA TTTTAATTAC
 701 CATCACAGAT GGAAACAAGT TAACAAGTAC TGCTGGTGTT CAAGAAGAGC
 751 TCCATCTTCC TTTGAATTCC CCTCTGCCTG GAAGTGAACT AACCAAAGAA
 801 CCTTTTCGTT GGGATCAAAG GTTATTTGCC CTGGTGTTGC GTTTGCCTGG
 851 AGTGGCTTCT ACCGAACCAG AGCAACTAGG GAGCGTACCA ACTGATGAAT
 901 CTGCCATCAC ACAGATGTGT GAAGTCACAG GAGGTCGCTC CTACTGTGTG
 951 AGAACACAAA GAATGTTGAA TCAATGTTTA GAATCTCTAG TTCAAAAAGT
1001 TCAGAGTGGT GTAGTTATTA ATTTTGAAAA AACAGGACCA GATCCACTTC
1051 CTATTGGAGA AGATGGACTT ATGGATTCAT CCAGGCCAAG CAATTCATTT
1101 GCTGCTCAGC CATGGCATAG TTGTCATAAA CTCATTTATG TACGACCTAA
1151 CTCTAAAACT GGTGTTCCTG TTGGACATTG GCCAATTCCA GAATCTTTTT
1201 GGCCAGATCA GAATTTACCT TCACTACCTC CACGAACATC TCATCCTGTT
1251 GTGAGGTTCT CCTGTGTAGA TTGTGAGCCA ATGGTAATAG ACAAACTTCC
1301 TTTTGACAAA TATGAACTTG AACCTTCGCC CTTAACTCAG TATATCTTGG
1351 AACGAAAGTC TCCCCATACC TGCTGGCAGG TATTTGTTAC TAGCAGTGGA
1401 AAGTACAATG AACTTGGATA TCCATTTGGT TATTTAAAAG CCAGTACAAC
1451 TTTAACTTGT GTAAACCTCT TTGTGATGCC TTACAACTAC CCAGTTTTAC
1501 TTCCTCTTTT AGATGACTTG TTTAAAGTTC ACAAGCTTAA GCCAAATCTG
1551 AAGTGGCGAC AGGCTTTTGA CAGCTACTTA AAAACTCTGC CTCCATACTA
1601 CCTATTAACC AAACTAGAGT CAGAACGAAT ACTAGCATCA GTGGGGAAGA
1651 AACCTCCCCA GGAAATTGGA ATTAAAGTGA AAAATCATTC TGGAGGTGGC
1701 ATGTCCTTGA CTCACAATAA AAATTTTAGA AAACTATTGA AAGAAATCAC
1751 AGGGGAAACT GCACTTAGAC TGACAGAATT GAACACCAAA GAATTTGCTG
1801 GCTTCCAAAT TGGGCTCTTA AACAAGGATT TGAAACCTCA GACATACAGA
1851 AATGCTTATG ATATTCCCCG TAGAGGTCTT TTAGACCAGC TGACCAGAAT
1901 GAGATCCAAT CTGCTGAAAA CGCACAAGTT TATTGTTGGA CAAGATGAAG
1951 ATTCCCTTCA TAGTGTTCCA GTTGCACAAA TGGGTAACTA TCAGGAATAT
2001 CTGAAGACAT TGGCTTCTCC ACTGCGAGAG ATTGATCCAG ACCAACCCAA
2051 AAGACTGCAT ACTTTTGGCA ATCCGTTTAA ACAAGATAAG AAGGGAATGA
2101 TGATTGATGA AGCAGATGAG TTTGTAGCAG GGCCACAAAA CAAAGTGAAA
2151 CGTCCAGGGG AACCCAACAG TCCTATGTCA TCTAAGAGAA GGCGGAGTAT
2201 GTCCCTGCTG TTGAGGAAAC CACAAACACC ACCTACTGTA ACTAACCATG
2251 TGGGCGGAAA GGGACCACCC TCAGCCTCGT GGTTCCCATC TTATCCAAAC
2301 CTCATAAAAC CCACCCTTGT ACATACAGAT GCTACTATCA TTCACGATGG
2351 CCATGAGGAG AAGATGGAAA ATGGTCAGAT CACACCTGAT GGCTTCCTGT
2401 CAAAATCTGC TCCATCAGAG CTTATAAATA TGACAGGAGA TCTTATGCCA
2451 CCCAACCAAG TGGATTCTCT GTCTGACGAC TTCACAAGTC TCAGCAAAGA
2501 TGGGCTGATT CAAAAACCTG GTAGTAACGC ATTTGTAGGA GGAGCCAAAA
2551 ACTGCAGTCT CTCCGTAGAT GACCAAAAAG ACCCAGTAGC ATCTACTTTG
2601 GGAGCTATGC CAAATACATT ACAAATCACT CCTGCTATGG CACAAGGAAT
2651 CAATGCTGAT ATAAAACATC AATTAATGAA GGAAGTTCGA AAGTTTGGTC
```

FIGURE 1A

```
2701 GAAAATATGA AAGAATTTTC ATTTTGCTTG AAGAAGTGCA AGGACCTCTG
2751 GAGATGAAGA AACAGTTTGT TGAATTTACC ATCAAGGAAG CCGCAAGGGT
2801 TAAAAGACGA GTCCTAATTC AGTACCTTGA GAAGGTACTA GAAAAAATAA
2851 ATTCCCACCA CCTTCACAAC AACATTAGTC ACATCAACAG CAGATCATCA
2901 TGTTAGTGCA AAGACCAGTG AGAAAAAAAT GACAAGTTTT CTGTGCTGTA
2951 GGATGGAACA GGATATTGTT GAAGCCTCCT GGAATGTTTG AGTCAAGGGA
3001 ATTGCTTTCC AGATGCTAAG AAGCAGCAGT GGGGCTTTTG AATTTTATGA
3051 TTATCTGGCA GTGAAAGCTG GGCTTTTGCC TTAATAATTT TTTAAAGTAT
3101 GAATTGTTTT GTTTTGTTTT CCTCAATTGA GGAAGCTGAT GTTATTAATT
3151 CACAGGCTAA ATTCGGTAAA CACCACTGCC CCTACCACGG GTAATGAGAG
3201 GTCACTCACT TGAACTTTGC CATTCCAGGC ATTCTCAGAG TGGCGAGGGG
3251 CCACCTGCAA GTGGAGCACA ACTTGGTGCT CTTACTGTGT CCTTCAGAAA
3301 GAATAGGTGT ACAGAAAGGA AATGGCAATC TTATGTGTGC TGAACAAAGT
3351 TTTCAACAAT TCCTAGTTGT GCCTTTTAAA CCATGCAATA TTCAGGATAG
3401 TTTGAATCAA AGAAGTAAGA AGCTGCTATT TGGGTAACTT ATTTCTCTGT
3451 GGGAAGGGGC AGGGAGAGTC ACCAAACAAT CTACCTCCAA CTCTCTTCTC
3501 TTTTGTCTAG AGACATTACA AAGTGCACTT GAGGCTGCCC CCAACCTCTG
3551 ACATTTGTTC TTGCATGTGA TGATAGAAAG TCTTCAGATG GACTTATACA
3601 TTCTGTGCTT TGGAAGCACA AGAAGAACAA AATATGTGTA TATTTCCTTT
3651 AATGTTTATA CAAAAGTTTA TATGGAGCAG TATTGTTATG TTTGTATGAA
3701 TTTGCAAAAA TTAAAGTGTA CAAAGAGATT TTGATTTTGC ATATATAAAA
3751 TAAATCATTT TATTGATTTT CAAAAAAAAA AAAAAAAAAA AAAAAAAAAA
3801 AAAAAAAAAA AA    (SEQ ID NO:1)
```

FEATURES:
5'UTR:        1-320
Start Codon:  321
Stop Codon:   2904
3'UTR:        2907

Homologous proteins:
Top 10 BLAST Hits
```
                                                                        Score      E
CRA|1000682335191  /altid=gi|11024694 /def=ref|NP_036273.1| dele...      1137     0.0
CRA|18000005032338 /altid=gi|6679094  /def=ref|NP_032741.1| Notc...       876     0.0
CRA|18000005238915 /altid=gi|5081650  /def=gb|AAD39481.1|AF14132...       671     0.0
CRA|89000000193461 /altid=gi|7290624  /def=gb|AAF46073.1| (AE003...       406     e-112
CRA|1000682328940  /altid=gi|7512527  /def=pir||T17330 hypothetic...      399     e-110
CRA|113000004114246 /altid=gi|8924242 /def=ref|NP_061136.1| put...        226     1e-57
CRA|18000005027057 /altid=gi|7498598  /def=pir||T29487 hypotheti...       209     1e-52
CRA|1000682331974  /altid=gi|10955424 /def=ref|NP_053136.1| orf7...        38     0.63
```

BLAST dbEST hits:
```
gi|1401373  /dataset=dbest /taxon=9606 ...       878     0.0
gi|10245548 /dataset=dbest /taxon=96...          658     0.0
gi|3423499  /dataset=dbest /taxon=9606 ...       626     e-177
gi|747411   /dataset=dbest /taxon=9606 /...      505     e-140
gi|10837301 /dataset=dbest /taxon=960...         490     e-135
gi|2229972  /dataset=dbest /taxon=9606 ...       478     e-132
gi|1400525  /dataset=dbest /taxon=9606 ...       349     2e-93
gi|2028463  /dataset=dbest /taxon=9606 ...       208     5e-51
```

FIGURE 1B

EXPRESSION INFORMATION FOR MODULATORY USE:
library source:
Expression information from BLAST dbEST hits:
gi|1401373   Fetal Liver Spleen
gi|10245548  Breast-normal
gi|3423499   Fetal liver spleen
gi|747411    Fetal liver spleen
gi|10837301  Hypothalamus
gi|2229972   Ovarian tumor
gi|1400525    Fetal liver spleen
gi|2028463   Lung fibroblast Expression information from PCR-based tissue screening panels:
Human whole brain

FIGURE 1C

```
  1 MPILLFLIDT SASMNQRTDL GTSYLDIAKG AVELFLKLRA RDPASRGDRY
 51 MLVTYDEPPY CIKAGWKENH ATFMSELKNL QASGLTTLGQ ALRSSFDLLN
101 LNRLISGIDN YGQGRNPFFL EPSILITITD GNKLTSTAGV QEELHLPLNS
151 PLPGSELTKE PFRWDQRLFA LVLRLPGVAS TEPEQLGSVP TDESAITQMC
201 EVTGGRSYCV RTQRMLNQCL ESLVQKVQSG WINFEKTGP DPLPIGEDGL
251 MDSSRPSNSF AAQPWHSCHK LIYVRPNSKT GVPVGHWPIP ESFWPDQNLP
301 SLPPRTSHPV VRFSCVDCEP MVIDKLPFDK YELEPSPLTQ YILERKSPHT
351 CWQVFVTSSG KYNELGYPFG YLKASTTLTC VNLFVMPYNY PVLLPLLDDL
401 FKVHKLKPNL KWRQAFDSYL KTLPPYYLLT KLESERILAS VGKKPPQEIG
451 IKVKNHSGGG MSLTHNKNFR KLLKEITGET ALRLTELNTK EFAGFQIGLL
501 NKDLKPQTYR NAYDIPRRGL LDQLTRMRSN LLKTHKFIVG QDEDSLHSVP
551 VAQMGNYQEY LKTLASPLRE IDPDQPKRLH TFGNPFKQDK KGMMIDEADE
601 FVAGPQNKVK RPGEPNSPMS SKRRRSMSLL LRKPQTPPTV TNHVGGKGPP
651 SASWFPSYPN LIKPTLVHTD ATIIHDGHEE KMENGQITPD GFLSKSAPSE
701 LINMTGDLMP PNQVDSLSDD FTSLSKDGLI QKPGSNAFVG GAKNCSLSVD
751 DQKDPVASTL GAMPNTLQIT PAMAQGINAD IKHQLMKEVR KFGRKYERIF
801 ILLEEVQGPL EMKKQFVEFT IKEAARVKRR VLIQYLEKVL EKINSHHLHN
851 NISHINSRSS C  (SEQ ID NO:2)
```

FEATURES:
Functional domains and key regions:
[1] PDOC00001 PS00001 ASN_GLYCOSYLATION
N-glycosylation site Number of matches: 4
    1    455-458 NHSG
    2    703-706 NMTG
    3    744-747 NCSL
    4    851-854 NISH

[2] PDOC00004 PS00004 CAMP_PHOSPHO_SITE
cAMP- and cGMP-dependent protein kinase phosphorylation site 623-626 RRRS

[3] PDOC00005 PS00005 PKC_PHOSPHO_SITE
Protein kinase C phosphorylation site

Number of matches: 9
    1    212-214 TQR
    2    253-255 SSR
    3    359-361 SGK
    4    434-436 SER
    5    508-510 TYR
    6    534-536 THK
    7    620-622 SSK
    8    621-623 SKR
    9    820-822 TIK

FIGURE 2A

[4] PDOC00006 PS00006 CK2_PHOSPHO_SITE
Casein kinase II phosphorylation site

Number of matches: 13
         1     23-26    SYLD
         2     45-48    SRGD
         3     54-57    TYDE
         4     94-97    SSFD
         5    106-109   SGID
         6    127-130   TITD
         7    181-184   TEPE
         8    238-241   TGPD
         9    314-317   SCVD
        10    430-433   TKLE
        11    716-719   SLSD
        12    748-751   SVDD
        13    820-823   TIKE

[5] PDOC00007 PS00007 TYR_PHOSPHO_SITE
Tyrosine kinase phosphorylation site 361-367 KYNELGY

[6] PDOC00008 PS00008 MYRISTYL
N-myristoylation site

Number of matches: 12
         1    131-136   GNKLTS
         2    154-159   GSELTK
         3    177-182   GVASTE
         4    187-192   GSVPTD
         5    230-235   GVVINF
         6    249-254   GLMDSS
         7    281-286   GVPVGH
         8    458-463   GGGMSL
         9    460-465   GMSLTH
        10    740-745   GGAKNC
        11    741-746   GAKNCS
        12    761-766   GAMPNT

[7] PDOC00009 PS00009 AMIDATION
Amidation site

Number of matches: 2
         1    441-444   VGKK
         2    792-795   FGRK

[8] PDOC00016 PS00016 RGD
Cell attachment sequence 46-48 RGD

FIGURE 2B

[9] PDOC00039 PS00039 DEAD_ATP_HELICASE
DEAD-box subfamily ATP-dependent helicases signature 594-602 MIDEADEFV Membrane spanning structure and domains:
 Helix Begin   End   Score  Certainty
   1    377    397   0.990  Putative
   2    755    775   0.843  Putative BLAST Alignment to Top Hit:
>CRA|1000682335191 /altid=gi|11024694 /def=ref|NP_036273.1| deleted
        in cancer 1; RNA helicase HDB [Homo sapiens] /org=Homo
        sapiens /taxon=9606 /dataset=nraa /length=887
        Length = 887

Score = 1137 bits (2910), Expect = 0.0
 Identities = 586/909 (64%), Positives = 689/909 (75%), Gaps = 75/909 (8%)

Query: 1    MPILLFLIDTSASMNQRTDLGTSYLDIAKGAVELFLKLRARDPASRGDRYMLVTYDEPPY 60
            MPILLFLIDTSASMNQR+ LGT+YLD AKGAVE F+KLRARDPASRGDRYMLVT++EPPY
Sbjct: 1    MPILLFLIDTSASMNQRSHLGTTYLDTAKGAVETFMKLRARDPASRGDRYMLVTFEEPPY 60

Query: 61   CIKAGWKENHATFMSELKNLQASGLTTLGQALRSSFDLLNLNRLISGIDNYGQGRNPFFL 120
             IKAGWKENHATFM+ELKNLQA GLTTLGQ+LR++FDLLNLNRL++GIDNYGQGRNPFFL
Sbjct: 61   AIKAGWKENHATFMNELKNLQAEGLTTLGQSLRTAFDLLNLNRLVTGIDNYGQGRNPFFL 120

Query: 121  EPSILITITDGNKLTSTAGVQEELHLPLNSPLPGSELTKEPFRWDQRLFALVLRLPGVAS 180
            EP+I+ITITDG+KLT+T+GVQ+ELHLPLNSPLPGSELTKEPFRWDQRLFALVLRLPG  S
Sbjct: 121  EPAIIITITDGSKLTTTSGVQDELHLPLNSPLPGSELTKEPFRWDQRLFALVLRLPGTMS 180

Query: 181  TEPEQLGSVPTDESAITQMCEVTGGRSYCVRTQRMLNQCLESLVQKVQSGVVINFEKTGP 240
              E EQL  VP D+SAIT MCEVTGGRSY V + RMLNQCLESLVQKVQSGVVINFEK GP
Sbjct: 181  VESEQLTGVPLDDSAITPMCEVTGGRSYSVCSPRMLNQCLESLVQKVQSGVVINFEKAGP 240

Query: 241  DPLPIGEDGLMDSSRPSNSFAAQPWHSCHKLIYVRPNSKTGVPVGHWPIPESFWPDQNLP 300
            DP P+ EDG  D SRP    F +QPWHSCHKLIYVRPN KTGVP+GHWP+PESFWPDQN P
Sbjct: 241  DPSPV-EDGQPDISRP---FGSQPWHSCHKLIYVRPNPKTGVPIGHWPVPESFWPDQNSP 296

Query: 301  SLPPRTSHPVVRFSCVDCEPMVIDKLPFDKYELEPSPLTQYILERKSPHTCWQVFVTSSG 360
            +LPPRTSHPVV+FSC DCEPMVIDKLPFDKYELEPSPLTQ+ILERKSP TCWQV+V++S
Sbjct: 297  TLPPRTSHPVVKFSCTDCEPMVIDKLPFDKYELEPSPLTQFILERKSPQTCWQVYVSNSA 356

Query: 361  KYNELGYPFGYLKASTTLTCVNLFVMPYNYPVLLPLLDDLFKVHKLKPNLKWRQAFDSYL 420
            KY+ELG+PFGYLKAST L CVNLFVMPYNYPVLLPLLDDLFKVHK KP LKWRQ+F+SYL
Sbjct: 357  KYSELGHPFGYLKASTALNCVNLFVMPYNYPVLLPLLDDLFKVHKAKPTLKWRQSFESYL 416

Query: 421  KTLPPYYL------------------------------------LTKLESERILASVGK 443
            KT+PPYYL                                    K+ES+R++ SVGK
Sbjct: 417  KTMPPYYLGPLKKAVRMMGAPNLIADSMEYGLSYSVISYLKKLSQQAKIESDRVIGSVGK 476

FIGURE 2C

```
Query:  444 KPPQEIGIKVKNHSGGGMSLTHNKNFRKLLKEITGETALRLTELNTKEFAGFQIGLLNKD 503
             K  QE GIKV++ S  G+S+ + K+F++LL+ I+ +   RL +LN KE+ GFQ+ LLNKD
Sbjct:  477 KVVQETGIKVRSRS-HGLSMAYRKDFQQLLQGISEDVPHRLLDLNMKEYTGFQVALLNKD 535

Query:  504 LKPQTYRNAYDIPRRGLLDQLTRMRSNLLK-THKFIVGQDEDSLHSVPVAQMGNYQEYLK 562
             LKPQT+RNAYDIPRR LLD LTRMRSNLLK T +F+ GQDED +HSVP+AQMGNYQEYLK
Sbjct:  536 LKPQTFRNAYDIPRRNLLDHLTRMRSNLLKSTRRFLKGQDEDQVHSVPIAQMGNYQEYLK 595

Query:  563 TLASPLREIDPDQPKRLHTFGNPFKQDKKGMMIDEADEFVAGPQNKVKRPGEPNSPMSSK 622
             +  SPLRE+DPDQP+RLHTFGNPFK DKKGMMIDEADEFVAGPQNK KRPGEPN     K
Sbjct:  596 QVPSPLRELDPDQPRRLHTFGNPFKLDKKGMMIDEADEFVAGPQNKHKRPGEPNMQGIPK 655

Query:  623 RRRSMSLLLRKPQTPPTVTNHVGGKGPPSASWFPSYPNLIKPTLVH-----TDATIIHD- 676
             RRR MS LLR  Q   P V NH+GGKGPP A    + P+LIKP +H      T+ +IIHD
Sbjct:  656 RRRCMSPLLRGRQQNPVVNNHIGGKGPP-APTTQAQPDLIKPLPLHKISETTNDSIIHDV 714

Query:  677 --GHEEKMENGQITP---DGFLSKSAPSELINMTGDLMPPNQVDSLSDDF---TSLSKDG 728
                H  +  ITP    D  S S+P+ L+         PN +++L D       L+  G
Sbjct:  715 VENHVADQLSSDITPNAMDTEFSASSPASLLE-----RPTNHMEALGHDHLGTNDLTVGG 769

Query:  729 LIQKPGSNAFVGGAKNCSLSVDDQKDPVASTLGAMPNTLQITPAMAQGINADIKHQLMKE 788
              ++    ++      + C+    +++ AS+L     +      + +N ++K Q+MKE
Sbjct:  770 FLE---NHEEPRDKEQCA-----EENIPASSLNKGKKLMHC--RSHEEVNTELKAQIMKE 819

Query:  789 VRKFGRKYERIFILLEEVQGPLEMKKQFVEFTIKEAARVKRRVLIQYLEKVLEKINSHHL 848
             +RK GRKYERIF LL+ VQG L+ +   F++  IKEA+R K+R+LI+ LE   L++I  H
Sbjct:  820 IRKPGRKYERIFTLLKHVQGSLQTRLIFLQNVIKEASRFKKRMLIEQLENFLDEI--HRR 877

Query:  849 HNNISHINS 857   (residues 1-857 of SEQ ID NO:2)
             N I+HINS
Sbjct:  878 ANQINHINS 886   (SEQ ID NO:4)

>CRA|18000005032338 /altid=gi|6679094 /def=ref|NP_032741.1|
        Notch2-like [Mus musculus] /org=Mus musculus /taxon=10090
        /dataset=nraa /length=1687
        Length = 1687

Score =  876 bits (2239), Expect = 0.0
 Identities = 470/797 (58%), Positives = 561/797 (69%), Gaps = 80/797 (10%)

Query:  114 GRNPFFL-EPSILITITDGNKLTSTAGVQEELHLPLNSPLPGSELTKEPFRWDQRLFALV 172
             G+  P FL +P+I+TITDG+KLT+T+GVQ+ELHLPLNSPL GSELTKEPF  +   LV
Sbjct:  917 GKKPLFLGKPAIIITITDGSKLTTTSGVQDELHLPLNSPLAGSELTKEPFVGIRDYLLLV 976

Query:  173 LRLPGVASTEPEQLGSVPTDESAITQMCEVTGGRSYCVRTQRMLNQCLESLVQKVQSGVV 232
             LRLPG  S E EQL  VP D+SAIT MCEVTGGRSY V + RMLNQCLESLVQKVQSGVV
Sbjct:  977 LRLPGTMSVESEQLTGVPLDDSAITPMCEVTGGRSYSVCSPRMLNQCLESLVQKVQSGVV 1036

Query:  233 INFEKTGPDPLPIGEDGLMDSSRPSNSFAAQPWHSCHKLIYVRPNSKTGPVGHWPIPES 292
             INFEK GPDP P   +G  D SRP   F  +QPWHSCHKLIYVRPN KTGP+GHWP+PES
Sbjct: 1037 INFEKAGPDPPPAEAEGQPDISRP---FGSQPWHSCHKLIYVRPNPKTGVPIGHWPVPES 1093
```

FIGURE 2D

```
Query:  293 FWPDQNLPSLPPRTSHPVVRFSCVDCEPMVIDKLPFDKYELEPSPLTQYILERKSPHTCW 352
            FWPDQN P+LPPRTSHPVV+FSC DCEPMVIDKLPFDKYELEPSPLTQY   RKSP TCW
Sbjct: 1094 FWPDQNSPTLPPRTSHPVVKFSCTDCEPMVIDKLPFDKYELEPSPLTQY-SRRKSPQTCW 1152

Query:  353 QVFVTSSGKYNELGYPFGYLKASTTLTCVNLFVMPYNYPVLLPLLDDLFKVHKLKPNLKW 412
            QV+V++S KYNELG+PFGYLKAST LTCVNLFVMPYNYPVLLPLLDDLFKVHK KP LKW
Sbjct: 1153 QVYVSNSAKYNELGHPFGYLKASTALTCVNLFVMPYNYPVLLPLLDDLFKVHKAKPTLKW 1212

Query:  413 RQAFDSYLKTLPPYYL--------------------------------LTKLESE 435
            RQ+F+SYLKT+PPYYL                                K+ES+
Sbjct: 1213 RQSFESYLKTMPPYYLGPLKKAVRMMGAPNLIADSMEYGLSYSVISYLKKLSQQAKIESD 1272

Query:  436 RILASVGKKPPQEIGIKVKNHSGGGMSLTHNKNFRKLLKEITGETALRLTELNTKEFAGF 495
            R++ SVGKK QE GIKV++ S  G+S+ H K F ++L+ I+ +   RL +LN KE+ GF
Sbjct: 1273 RVIGSVGKKVVQETGIKVRSRS-HGLSMAHRKGF-QVLQGISEDVPHRLLDLNMKEYTGF 1330

Query:  496 QIGLLNKDLKPQTYRNAYDIPRRGLLDQLTRMRSNLLK-THKFIVGQDEDSLHSVPVAQM 554
            Q+ LLNKDLKPQT+RNAYDIPRR LLD LTRMRSNLLK T KF+ GQDED +HSVP+AQM
Sbjct: 1331 QVALLNKDLKPQTFRNAYDIPRRNLLDHLTRMRSNLLKSTRKFLKGQDEDQVHSVPIAQM 1390

Query:  555 GNYQEYLKTLASPLREIDPDQPKRLHTFGNPFKQDKKGMMIDEADEFVAGPQNKVKRPGE 614
            GNYQEYLK + SPLRE+DPDQP+RLHTFGNPFK DKKGMMIDEADEFVAGPQNK KRPGE
Sbjct: 1391 GNYQEYLKQVPSPLRELDPDQPRRLHTFGNPFKLDKKGMMIDEADEFVAGPQNKHKRPGE 1450

Query:  615 PNSPMSSKRRRSMSLLLRKPQTPPTVTNHVGGKGPPSASWFPSYPNLIKPTLVHTDAT-- 672
            P+    KRRR S LLR + P V +H+GGKGPP A   + P LIKP +H +AT
Sbjct: 1451 PSMQGIPKRRRCASPLLRGRRQSPAVNSHIGGKGPP-APMTQAQPGLIKPLPLHKEATND 1509

Query:  673 -IIHD---GHEEKMENGQITPDGFLSKSAPSELINMTGDLMPPNQVDSLSDDFTSLSKDG 728
             I+ D   H    + +TP+ ++ S          PPN ++ ++   +L +
Sbjct: 1510 SIVDDVVENHVADQLSSDMTPNAMDTEFLTS----------PPNLLEPSTNHTEALGHEH 1559

Query:  729 LIQKPGSNAF-VGG-------AKNCSLSVDDQKDPVASTLGAMPNTLQITPAMAQGINAD 780
            L   G+N   VGG       +N S ++  + AS+L  +      +  + +N +
Sbjct: 1560 L----GNNDLTVGGFLENHEEPRNKEQSAEE--NIPASSLNKGKKLMHC--RSHEEVNTE 1611

Query:  781 IKHQLMKEVRKFGRKYERIFILLEEVQGPLEMKKQFVEFTIKEAARVKRRVLIQYLEKVL 840
            +K Q+MKE+RK GRKYERIF LL+ VQG L+ +   F++  IKEA+R K+R+LI+  LE L
Sbjct: 1612 LKAQIMKEIRKPGRKYERIFTLLKHVQGSLQTRLIFLQNVIKEASRFKKRMLIEQLENFL 1671

Query:  841 EKINSHHLHNNISHINS 857   (residues 114-857 of SEQ ID NO:2)
            ++I H  N I+HINS
Sbjct: 1672 DEI--HRRANQINHINS 1686   (SEQ ID NO:5)
```

FIGURE 2E

```
   1 CCCTAGCCCA TGTAGGCATT GCCCTTCTAC ACTGACATTT GTATCGGAAT
  51 GGAAATGGGG GCTTCTAGTA TCTTTTTCAT CCTTATTTCT TCATTAATTC
 101 CCTACTTTCC ACCAGAATGG CCTGAAATGC ACCATACATA GTACTATCTT
 151 TGGCTGAGTT TTTGTTCATA TCATTCCTTC CAACCCAGAT TCCCTCTCTT
 201 CCCTTTTTGT GCCTTGTTCG TGAAATCCTA TGAATTTCTA GACTGGACCA
 251 TTGTTTCCAT AGCACTTTTT AACTTGCATC CTTGTTTGTC CCTGATTCAT
 301 ATACTGCCAT ATGACTTCTT TTAAAATCGT ATTTCTCTGA GAATGTTATT
 351 GAATGTGCAT ATATAATATA TGAAACATAT ACACAGAACA TACATATATA
 401 TATATATATA GAGAGAGAGA GAGAGAGAGA GTGTATATAA AATATATAAA
 451 ATACTTTTTT GAGATGTTAT CTCATTCTGT TGCCCAGGCT GGAGTGCAGT
 501 GGTGTGATCT CAGTTCACTG CAACCTCCGT CTCCTGGGTT GAAGTGATTC
 551 TCCTGCCTCA GCCTCCCAAG TAGCTGGGAC TACAGGCGCC TGCTCCCATG
 601 CCCGGCTAAT TTTTGTATTT TTAGTAGAGA CGGGGGTTTC ACCATGTTGG
 651 CCAGGCTGGT CTCAAACTCC TGCCCTCAAA TGATCCACCC AACTCGGCCT
 701 CCCAAAGTGC TGGAATTACA GGCATGAGCC ACTGCGCCTG GCCAAAATAT
 751 ATAAAATATT ATGTATGTAT ATGTCATCAT CTCTCCTCAA TGAAACTGCA
 801 AACTCATTGA AGTCCTGGAT TCCACATTGT CAATAGTAAT TGCCAGGAAT
 851 ACACAAGTCC AATTTTTAAA ATTGTGTCAT ATGAAGTAGT CAATCAAGTG
 901 TGGTTGGCCA CTTACTGAGT CTCTTCACAG AGCCAGACCT GAGAGTATCC
 951 GTAATTGTTA CCCTAACCTC AGGGAGCTGC ATTTTCCTCT ACTGAAAATT
1001 GAATACAATG CCATCTGCCA TAATTAATTC AAAGATTAAA CAAGGCTACC
1051 GTGGGTGCCT GGCTCTTCAT AGGCACTCAA TAAATGTGAG TTGAGAGCCT
1101 GCCCCTGTGG TCCCAGCTAC TTGAGAGGCT GAGATGGGAG GATCGCTTAA
1151 GCCCAGGAGC TGGACGCTGC AGGCAGCTAT GATGGGGCCA CTGCACTCCA
1201 GCCTGGGCGA TCAAGCGAGA TCCTCTTTAT TTATTTATAA AAATAAATAA
1251 ATAAATAAAT ATGTGAGTTG AATCACAATC TAGGTTTGCA AACCTCCATG
1301 TGTAAAGGCT GCGCAGAGGG AACAGTGGTG GAATTATCAC AGGCAGGCCA
1351 ATGTTTCAAA GAGCTTAGTG AAACTGAAGA AGCTTGTGCA TACAAAAGGC
1401 CAGTTTAGGT AACTGTAACT GTGTTTAAGC TTTAGTTTCC TTTCTAAGTA
1451 GATATATGTG GAATGCAAGG CCAGCAACCA ACTCACAAAT ACTGATCAAG
1501 ACGGGGAGG GATCTAAAGG AATGTGAGTA CGTCCTGCCA GGAAAGAAGT
1551 TTGCTGCTTC TGAAATATTT TCGTCTTCGC CACTGGCAGG ATTGATCGAT
1601 TGCAGTTAGC GAAGAATTTT CTGTGCAAAC TGTCCAAGCA TCTGCTTCTG
1651 TACTTCTGTA CAACTGTTGC TCAAATTCAC TCTTCTTTTC GAATCACCAT
1701 CTTTGAAGAG AGACAGAAAA ATCCATTTAA ACCACCCGAA CTAATCATTC
1751 GAACTGCTTC CAAGTCCTTT AAAGGAGAAT CCTAGCGAGG GTCCGTAACA
1801 CTTCCCCTTA CCCTCTGCCT GGGTTCAAAC TTCAACTCCC AGGGTTCGCC
1851 CAAGTCCCTC CCCTAGTCCT GTCATCTAAT GAATATGCAA ATACCACATA
1901 ATTGGCAGCC AATGGCATGG GTTCTGGTCA CATGGTGCCG ATGGTAGGTG
1951 AGCAGACAGA AGTTGTCAGT GAACAGAGAC GGCGCTCAGT CTGGGGCGAG
2001 CGCTCTAGTG AGCGCGGACG GATGCTTAGG CAGTAGTCCT GGCAGCGGCA
2051 GTAGTGGTGG CAGCAGAAGA GAGGAAGGGG GAGGGCCCCG AGGGCTACAC
2101 ACGCTCACAC TTTCAAGTTC CCTTGGAGGG AGAGGAGGTG GGGCTGCAGA
2151 AAGAGGAGGC CAGGAGCGGT CCCATCCGTC CCGTCCCGTC CCGTCTCCCC
2201 CTCTTCCTCT TGCTCCTTGC CCCCCGGCTC TGCGAGAGTT GAGGGTTCAG
2251 GTGGCCGTAC GCGGCAGTGA GGGCAAGAGG GCCGGGAGAG TGGGGAGCGG
2301 AGGCAGGAGT GCGGGGGAAG ATGCCCATCC TGCTGTTCCT CATAGACACG
2351 TCCGCCTCTA TGAACCAGCG CACTGACCTG GCACCTCTT ATTTGGACAT
2401 TGCCAAAGGC GCTGTGGAGT TATTCTTGAA GGTAAAGGGA GGGGAGGGGA
2451 GAGATGGGGA GAGCTCCCGA GGGATTTCAG GGTGTGGATT GAGGTGCTTC
2501 TGTAACGTTT GTATCGCCCT CCCCCCTCCT TTCCTACGCG ACCCCCTCCG
2551 TCATCCCTTG CCCCGCAGCT GCGCGCCCGG GACCCGGCCA GCCGTGGAGA
2601 CAGGTACATG CTGGTCACCT ACGACGAACC CCCGTACTGC ATCAAGGTAA
2651 AGGGGCTACG GGTGGGGGGA CAGGCGGGAA GCGGGAGCAA GTCGGCGGGG
```

FIGURE 3A

```
2701 GCTGCTTACC CCCCTGCCCC CGCCTAAGGC GGTCCTGCGT CGCCCGGCGG
2751 GGCGGGCGGC GAGGGGGTGC GCAGAGGGCG GGCGGAGTGG TGCCGTCGGC
2801 GGCTTCGGAG TAGCTGTCGC GCCTGGGGTC GGGGAGAGGG GACCGGGGAG
2851 GAGCAGCCCC GGGGAGAAAC CGCAGGAGGG CCGAGCTCGT GGCGCGACAA
2901 CCGCAGCCGC CTCGGAACAT GGCGGACATT TTGCTTTTGT ATGAGCCTGC
2951 GAGAGGGAGA CTGAGGGCGC TGCTGAGATG GAAAGGAGGG AGGGGAGGGA
3001 GGAGCGGGTA AGGAGGGCCC GAAACCCGGA GGGAGGCTGC GAGGCGGGCC
3051 CGCCCCTTCG AGGCGCACCG CGCGAGGGTG CGGCCGCGGC CGGGGGGCCG
3101 GACGGAGCCT GCGACTCCGC CCCGAGGTCC TGCCGGCCGG GCGCGCGGGC
3151 TTTCCCGGAG CCTGGGCTCC TCCTCTGGCC CCTCCTTCCT CCCCCGGTCT
3201 TCCTCCCCCT CCTTGGGCTC TTCGCTGCAT CTCCTCCTTC TCCCCCTCTT
3251 CCTCCTGGTC CCCTCCCCTT CCTGCTGAGA GCGTGGCAGA GCCAGCCGCC
3301 GGCCTTCAAA GACTAGACAA CCGCCTTTGC ACTCGTTGGC CTCTCACCAC
3351 CCCCGCGCAA TCGGAAATCT GTCCACGACG CCAGTCTCCC CACCCCCAGA
3401 CCCGGAGAAA GTCTTTGCGT TTCTGCTCCG GAATTGGCCA GGTTCAGCCC
3451 CGCTCTCAGT TACCTTAGCT ACTGTTACTG TTTCATTGGA AATTCCAGCG
3501 AAGCAACGAC ACGGAGGGGG ACGTGCCAAG TGCGAACCCA CAGGGGCAGA
3551 GCTTTTTAGG GATCCGCTCT ACCTATTTAC ATCATAAATT AGGTTTGTGC
3601 TAGCCACGTA GGAATTAATC CAGGGACAAG AAAGAAAGGA AGGGGAGGAC
3651 TCAAATGTGA GCATTTGTAA TAGTCAAGTT CGATGATTTG ATTCTGACCT
3701 ACAGGAGAAA AGTAGGGAGG ACGGTCTCTG TGGGGGAATT TATGTTCCTA
3751 TGGTGAGGAG ATAAAGAACT GCTGCTTTGC CTGCAGTGGC CAGATAAAAT
3801 GGAATTTAAA CTGTTAAATC AACCTGCATA AGAGTCCTGC TTGCATATTG
3851 AAATTTTAAA AATACTACCA CAATCCTTGA CGTCTTTTGT TAGGCTTTTT
3901 CTTTTTTCCT CAGAATAATC GTAATAGTGC TAGGGAGACG CAGTCTGGAT
3951 GTGTTGTGAT CCGTTTCTGT AGAGTGAGGT GTTTTAATGA ATGGAACCTA
4001 CCAAGCTGAA TAGTTGGCCA AAGAGTGTTC CTTCAAGCAT AAGGAAACCA
4051 AAGAGAAACT AATTTTGTAA CTCGTAGCTT CGGTTAACTG TTTAATTAGT
4101 AGGTTCCCCT TAAAACTGTT CTTTTTTCGA TAATTTGTTT TCAGTTTGTG
4151 ATTCTATCCA TTTAGAAAAG TGGAACAAGT AGACATCTTT CAAAATGCCG
4201 TAAGCTTTTT AAAAATGTCA GTTTTCCCAA AAGGATGTGA TCATTTTTTT
4251 CCACATAGAA AAGGAGATGT TTATACATCC TAGGTCTGAA TGTCTACACT
4301 CTTCGACTGC TAATACAGAT AAGAACCGAC CATTTGTAGT GTGGCCATTT
4351 GAAGACATGC TCCTTAATTC GAAGTAGTAA AAAAGATAAA CCACAAAGCA
4401 GTGTGCCTTC TTTTCCTTAA AGGAACAACT TATTGGCCGG GTGCGGTGGC
4451 TCAGGCCTGT AATCCCAGCA CTTTGGGAGG TCGAGATGGG CGGATTGCCT
4501 GAGCTCAGGA GTTTGAGACC AGCCTGGGCA ACATGGTGAA ACCCCGTCTT
4551 TACTAAAATA CAAAAAAACA AAACAAAAAA AAAACGGCC GGATGTGGTG
4601 GCGGGCGCCT GTAATCCCAG CTACGCGGGA GNNNNNNNNN NNNNNNNNNN
4651 NNNNNNNNNN NNNNNNNNNN NNNNNNNNNN NNNNNNNNNN NNNNNNNNNN
4701 NNNNNNNNNN NNNNNNNNNN NNNNNNNNNN NNNNNNNNNN NNNNNNNNNN
4751 NNNNNNNNNN NNNNNNNNNN NNNNNNNNNN NNNNNNNNNN NNNNNNNNNN
4801 NNNNNNNNNN NNNNNNNNNN NNNNNNNNNN NNNNNNNNNN NNNNNNNNNN
4851 NNNNNNNNNN NNNNNNNNNN NNNNNNNNNN NNNNNNNNNN NNNNNNNNNN
4901 NNNNNNNNNN NNNNNNNNNN NNNNNNNNNN NNNNNNNNNN NNNNNNNNNN
4951 NNNNNNNNNN NNNNNNNNNN NNNNNNNNNN NNNNNNNNNN NNNNNNNNNN
5001 NNNNNNNNNN NNNNNNNNNN NNNNNNNNNN NNNNNNNNNN NNNNNNNNNN
5051 NNNNNNNNNN NNNNNNNNNN NNNNNNNNNN NNNNNNNNNN NNNNNNNNNN
5101 NNNNNNNNNN NNNNNNNNNN NNNNNNNNNN NNNNNNNNNN NNNNNNNNNN
5151 NNNNNNNNNN NNNNNNNNNN NNNNNNNNNN NNNNNNNNNN NNNNNNNNNN
5201 NNNNNNNNNN NNNNNNNNNN NNNNNNNNNN NNNNNNNNNN NNNNNNNNNN
5251 NNNNNNNNNN NNNNNNNNNN NNNNNNNNNN NNNNNNNNNN NNNNNNNNNN
5301 NNNNNNNNNN NNNNNNNNNN NNNNNNNNNN NNNNNNNNNN NNNNNNNNNN
5351 NNNNNNNNNN NNNNNNNNNN NNNNNNNNNN NNNNNNNNNN NNNNNNNNNN
```

FIGURE 3B

```
5401  NNNNNNNNNN  NNNNNNNNNN  NNNNNNNNNN  NNNNNNNNNN  NNNNNNNNNN
5451  NNNNNNNNNN  NNNNNNNNNN  NNNNNNNNNN  NNNNNNNNNN  NNNNNNNNNN
5501  NNNNNNNNNN  NNNNNNNNNN  NNNNNNNNNN  NNNNNNNNNN  NNNNNNNNNN
5551  NNNNNNNNNN  NNNNNNNNNN  NNNNNNNNNN  NNNNNNNNNN  NNNNNNNNNN
5601  NNNNNNNNNN  NNNNNNNNNN  NNNNNNNNNN  NNNNNNNNNN  NNNNNNNNNN
5651  NNNNNNNNNN  NNNNNNNNNN  NNNNNNNNNN  NNNNNNNNNN  NNNNNNNNNN
5701  NNNNNNNNNN  NNNNNNNNNN  NNNNNNNNNN  NNCTTACTAT  ATAGCTGTGT
5751  GCTCTTTTAA  AATTAGTCAT  ACCTTTTACT  TGCAGTCCCG  GTTTGCATGG
5801  ATAGAATTAA  GTTTGACTTA  AGTACCACAT  AAAAAGCGTA  CGAAATGTAA
5851  GCATCATGTG  CTACATCTGT  TATGTTGCTT  TCTAGACAAG  TTTTATGCAT
5901  AGTGTTACAA  GTGTTGACCC  CACCTTTATA  CCGTGGTATC  TTCAGTGTAC
5951  ACAGCTAGTA  TGAAACCCTG  TTTAACATTT  AAAAACGTCT  AATGTATCCT
6001  TATAAAACTA  GTATGTGGTT  TTTAAAAGTG  TTAATGTTTT  GGGATTTTTT
6051  GGTATAATTG  TTGTTTTTAG  TCTTGGCTGA  GGTTCTGCTG  TCTTGTATGT
6101  TTTGTTTTGC  TATGAATCAT  AATTTCCTTT  TATTTAGTGA  ATAGAAGAGG
6151  CAGGCTTGTC  ACTACTATTA  CTTTGAAAGA  AAGTAAGCCA  TTAGAGTAGG
6201  GTATATATTA  ACAAAGGTAT  TCAAAATAGT  TTTATGTTGG  AAGCTACTTA
6251  AAATTATTTC  TTTTTTGTTG  AAGGAAATTA  TCTTTTTAAA  CATAAAATGG
6301  AGTTACTTTT  CTAGAAATAG  TTGAAACACA  TGTATAAAAT  ACTGGCCAGA
6351  AGATTTTTAT  AAATAGGAAA  TGATAATGTT  TCAAAGAAAT  ATCCTAAGTC
6401  TGTAATTTGA  AGACATACAT  TTGAAAAAGT  AAAATTTTCC  CTGAGTGTTG
6451  CCTTTTCCCA  TCCTGTAGCT  AGCTTTGCTT  ACTGGTGTCT  GCATGCCTTT
6501  GACAACATGT  ATCAGAAAAT  AGCAAAATTT  TGGCTTACAG  ATTTAGGAAG
6551  TAATTTAAGC  TTTTAAAATG  ATATGTGTTA  CAGGCATTTT  TTAGAATTTT
6601  AACTAAGACA  TAACTTTTTC  ATATGCCCAT  GAATATATTT  TATAGATCTT
6651  ATTTGCAAAA  GGAGTGACTT  TTATGGGAGC  CTTTCATTGT  GGTTAAGAAG
6701  CTATGGAAGA  GCTTATCAGT  GAAATAGTAG  CAACATGGCC  TGTGAGAGCA
6751  ATCTTAGACA  ATGAAAGATG  CTTTTAAAAC  TCAAAAAGCC  ACACAGGCAG
6801  TGCATTGACT  TTTACAACGA  ATTGCCTCTC  CCATGATCTT  GCTTTCTTAT
6851  CCACCTTCCT  TTACTGGCCA  TTTGTGGCAT  GCAGCAATAA  TTATTTTGAA
6901  ATAAGAAAAG  GAGAGAGTCA  ACAGTAGAAG  ACTAGACCTC  TGGGCAATAC
6951  AATCTTCAGA  CTAAGGACCA  GCTGTAAGAT  GACTAGGGAA  GATGCCTGAC
7001  AAAACTGTGG  AGGTCTGTCT  GTTCTGTATC  CCCAACCTCT  CTCGTATCCA
7051  TTCATTCTTA  TTTGCTCCTC  GTTTCAACCT  TCATCATTTC  TCACTTGCAA
7101  GCAGCCACTC  AGTTGTTCTC  CCTACTTCCA  GTCTTGCTCT  CCACTGATTC
7151  CTTCCCGTCA  TTGCCCTCAG  ATTGATCATT  CTTTAAATAA  AATAAAGTCA
7201  TTCCCCTATG  AAAAAAAAAT  CCTTCAGTGG  CACTCCATTA  CATTTCCCAA
7251  TAAAAGTAAA  TTTCTTGGCC  TGGCCTCCAT  GGCCGTTCAT  GATCTGGCCC
7301  TATCTTACCA  TGTCTCTGCG  CCCTCTCTTC  TCTTCTCATG  GACCTCAGGC
7351  TTCACCCACA  ATGAAAAATT  AGGTCCTCCT  CTCCAAACAC  ACTATGCCAG
7401  TTGCTTCTGT  GCCATTGTAA  ATGTTATTCC  CTCTGCCTGG  GACACATTGG
7451  TTGGCCAGAC  ATACCTCAGT  TCTTTATTCT  ATGTTTTCAA  AAGTCATTTT
7501  GTCCGTCGGC  TTTTTCCCTA  CTCCAAGCAG  TATAACAACT  TCCTCTGTGA
7551  TCCTTTAACA  TGTTGTCCAC  ACCTTAACTA  TATAGCATTT  AGCATGTTAT
7601  ATGGGGACTA  TTAGTGTTCA  TGTTGACTTC  CCTAATGTGA  GCTCTTGAAG
7651  GGCAAATATT  TGAACTTCTA  GGTATTTGTA  TCCCTAGTAC  CTAAGGGGGT
7701  GTTTAGATTT  TAATATGTAC  TCAACAAATG  GAAAAGGTT   TCAAGCAATA
7751  TGTTAAGTGT  CAAAGCTACT  CATTTCCCTC  ATGTCAAAGC  TTACCTCATT
7801  CCCGGTACTC  TTCCCCATAG  AGTAATCACT  ATTAACAATT  TGATATATTT
7851  AATGTTTATT  ACAGCTAGCA  TTTTCATATA  GGTTCAAGTT  TATAATATGG
7901  TAGAATCTTA  TTGTATTTTT  TACAAGATAA  GTGTATATAT  TTCTCTTTTT
7951  TCTTTTTTAT  AGAAGTATAA  TTCATATATA  GAAAATACAT  GAATCCTAAT
8001  GACTTGATGC  ATTTTTATAT  TTATACATTC  ATGTAACCAC  CATCCCAGGC
8051  CAAGATATAT  AACGTTTCCA  TCAACCAGGA  AAATGCCTCT  TGCATCTTTC
```

FIGURE 3C

```
8101 TGCAATCCAT CTCTCCCCTG CATGTAATTA CCGTTCTGAC TTTTATCACC
8151 ATTGTAGTGA CATGATCAAA ATGGTGTTTC CAAAAGACAA GTGTAACAGT
8201 GGGTTGACAC TACGGCAGTC TCGGCATTCA TTTACCATAT ACTTCTTGAA
8251 CATCTCCTCT GCACCAGGCT CTGTTATAGG GGCCTAAGGT GAAACCAGAA
8301 AGATCTGGCC TAAGAAGGGA CCAGAATAGT AAAAGACATG GTCCTAGTCA
8351 TTAAAGGTCT TGAGGATAGT CACTGGAAAA AGCTGACTAG AGAAGGTGGC
8401 TTAGGATATG GGAAATGTAA AGAGCAGTGG ACTCTTAACC AGAGAATTGG
8451 AGGTGAGGGA GGAGGATGCA CAGGACTCTG AGAATCTGGT GTGTCTCAAG
8501 ACTATAACTA GTTAAGACTG GACCACAGAA AGGCTTTGAA ACTTGTAAGC
8551 TAGATTTTGT ACATTTCTTC TGGGATGCAG AGCTCTTAGG TAGAATTGAA
8601 GAGAAATAGG ACAAAGCTTG TTGTCTATAT GCTTGTTTGG TTATAATTAC
8651 CTTTTAAGTG AGCTAAAGGG AGGGGAGAAT AAAAGGCTAG GGAGACCCAT
8701 AAGTTGTAGT TGAAATTGCC TAGTTTTGTT GCTTGCTGCT TGAGAGCTTT
8751 TGGCCTTATG GTTGGGATTG GGTGGGGGT AGGGAGATGG TGAAGGGCAG
8801 GGCACAGGTA AGGAAAGGGC AGATATTTTT TCTTTTCAGT TTGCCTTTGC
8851 TTTGGGAAGA TAATTATAAT TTAGAACACA GGGTTCTCAG TTTCACAGAG
8901 TGAAAAAATA TGATAGTGGT TCCACATCTC AGGAAGAAAT GTGTTTTCTA
8951 GAGAAGGGTA GGATTGAAGG ACCCTCCTTA TGGGAGTGAG AAGGGCAGTG
9001 AAGAAAGGAA ACTACATGTT TCATTTAAGT TCTTAAATGA AAAAGTCTTT
9051 GTAAACATGG CCTCCTCCCG GTTGCCTTTT ACCGAAAGAG TGTAAATGAG
9101 AGACCCAGGC AGTCCCTTTG TAACTGTGTA TTGGGAGCTT GGAACACATT
9151 ATCTCCTGGA TACAATGTTG GAAGTGGTGA TTATGTTCCC AGACCTTCCC
9201 TCCCAGGAAC CTTTTTAACC CTTCATGTCA CTTAGCCATA GACCTATTGT
9251 GTTTATAATT GTTTCTAATG GGAAATGGGT TTAAGTTTCC AGCTTGATTT
9301 GTTAAAAACA TATTCTTTCT CTCTTCTTCC TCACAACTGG GTGTGGACTT
9351 TGGTTCCATG AGGGGTGGGG ACACTGTAAA GGCTCCGGCA GAGAGGGTGA
9401 GGGGCTGAGG TGGCAGTGGA GGTAGGCGTG GCTCTTCACA TATGCCAGTT
9451 ACTCCTATTC ATAGATTGGC TACATTTACA CGGTTCAGCA TAGCGTCCAC
9501 TTAGCCACGT ATGGTTATTG AGCACTTGAA AGGTGGCTAG TCTGTCAGTG
9551 GGTGCTTCAA CAGACAGTGT AAAATATAAT ATTTTGGATA TATTAAGTAA
9601 ATTATTAATC TAACTTGTTT CTTTTTACTT TTTCAATGTG GTGAGTTGAA
9651 AATTTGAAAT TCCATATGTG AAATTTGCAC TATATTTCTA TTAGCAGTGT
9701 TTGTCTATAT TCTTTCTTAA GATATTTTAT GATGTTCATA TCCTAGGAAT
9751 TGTTTCTGAA GGAGGATCCT TTCTCTGGAA GTTCCGTTTA AAATGAACAC
9801 CCCCCCCCCC CCGACCCACC GCAATAAAAG ACTCATTTGT GCATGAAAGG
9851 TTATCATACA GTTCAGAGTT GATGGCTTGA TAACCCTTGC CTGTGGGCA
9901 AAATATGAAA GCATCCCATT CTTATTTGTA TTGAAAGCCA GTTTGGTTGC
9951 TTAGTCTTTT GGATGCAGTT GGTGATCCAA CTGGTTGGGT TAGAAGTCTT
10001 TTCCTGGGCT AAGTATAATG GAATATGTAT GTGAATGAAT GTAACTGCAG
10051 TAATTCAGAA TTCTGTTTAT AATATGTGCT CACCAGTAGT GCTAAATGTT
10101 TCATACTTTC AGTGTTATTA GAAATATGTA ACATGTCCGT TGTTTGATTT
10151 ACATAGCTAC TTTGCCCAAG AATTCTCAGG AGCAGCATTC TTTAGGAAGT
10201 GTAGGATAAA GGAGAAATAC TCTAGTTTGT CATAGTGTAA AACTTAACAA
10251 AGGGGAATTT GTATCACTGC TGTTTTTGAG AGCTTTCTTG ATGTTCCCCA
10301 GCGGAGCCCT TGTCTTATAT CATGGCAAGT CATCAGTGGC GTTAAAAGGA
10351 GGGAGAGGCC ACATGACTGG AGGGCTCCTA GGATTCTTAC TTCTGACAGT
10401 CGTTAACTTT CTCAAAACTT AATCCTCCTA GTGGAGGTTA CAGGAGTGAT
10451 TAATTGTTAT TTTTTGGTAA CTATAATGGC TCCCATTTAA GGAATAAGCA
10501 CCAATGTCTA ATTCTGAGGC TGGGTGGATT TATAGATATG CTGATGAATA
10551 GCATCTATAA GAGGTAGGAC CACTTTATAG CCCTAATTTT GGATCCTCCT
10601 AAATCCCATC TTATAGTCGA AGGTGTTATC TAGCTTGTAT AACTATCCCT
10651 GTATTTCAGA TATGATTTGA CTTATATTTG CTTCCTTGTA ATAATGAACA
10701 ATCACGAAAT AGCCTTCAAA TAATAGCAGC TGACATTTAT TGAGTAATGC
10751 TTAGGTACAG GGCAATGTGC TAATGAATGT AAAATGTTTA TTTAGTTTCT
```

FIGURE 3D

```
10801 CTTCCTAGTC AGTCTGTGTA CTGGATTACT AGGTACTATT ATTATACTCT
10851 TTTTATAGAT AAGGGAACCA GGGCCCAGAG AGGTTAAGTA ACCCAGCCAG
10901 TAGTAACCTA GGTCTGTCTC TATTCTAGTC TATTCAGTGA TTAACCACTT
10951 CACTTCTCCT ATCAATTGTG ACAGAAAATT CCTTTTGATA ACTTCTCACT
11001 GGTATTTTCT CATTATGATG CATGTCCTAG AGCCATCATT TTTTAAACAT
11051 AATTATCATG CTGTTATTTA TAGCTGCTTT TAATGTAATA GTGCTTGGCA
11101 TTGTAGCAAG CACTCAATGA ATGAAAATTA TTACTGCTAG TGTTATTATT
11151 TCTAATATTT CTCTGACTGT TGCTGGGTGA GTATTGTGGT GCATATGTTT
11201 GTAAAACACT TTTGCCTTTG ATGTCCCACA GTTATGCCCC TACTGGTGAC
11251 AGATATAGAG TTGTTGAGAC TCTCAGTTGA TGGAGTATGA AATAGTTGAG
11301 GACTGGAGGA TGTGAACTGG TGGCCTAGGC TGAGGAGGCC CTATAGGAAT
11351 AGTGGTAGGT TTGTAAAAGC AGCAGGGTAG TCCTTGGCTA TTTATTAATA
11401 ATAGCCACTA AAAACTGATA TGCCGTCTTC ACTTTACCAA TCTCCTGATA
11451 AATGCTTTTC TTATGAGGAA AAGAAAGATA TTCAGTGTAC TCCACAGTAG
11501 CCATTTGTTT TTTCTAATCC ACAGCCTCTG GAGGAGGTAG ACATGGTTTT
11551 TAAAAACGTC TGGAATACCA TCATGCCTTT GCAGAGTTTT GTGTATCAGC
11601 CTGAGCCTTA TCTGCTGGTG TGGTCTTCAT TTCAACTACT TCTCCCATTT
11651 TCCTCAAGCC ACACACCTGT CATAGCCAGA TCATTGGTTT TTTCCCCTCC
11701 TGTGTAGTTA GATGGCCTGG GGTAGAAGAG TGGATTTTAT AGAAGAAGTA
11751 GAGATGTCAG TCAGTGGGGT CTTAACCAGA GAAACATTGC ATGAAGACTT
11801 TTGGGTGATG TGCCAGATGT TTATAGAAAA AGTAGAATTC TATATCTTAA
11851 ACCATTTTCC CCTGGTTATA CTACTCATTA ATGCCAGTCG CTCTTTTATT
11901 ATCTATATCC TGCCCTGTAG CTCAAATAGT TCAGTGAACT TAGTACCAGG
11951 AGCCAAACAC AGGATTTGAA TGCAATTGAA CAAAAGTCTT GAAACATTTT
12001 TGTTTGTGCA ACTGAAAAAT AGTACTGTTA AGAAAACTAA ATATGATTTA
12051 TTAAGGTCTT AAGATTTACT GTCGAGCTAC TTGGGCAAAG TTACTAATAT
12101 TCATCCTCTT TGTCCTTGAC TACATTTGAA ACTAACTACT TCTTCCTTCC
12151 AGAAACTTAT CACTTCCTAT ATTCTGTTTC TCCACTCCTC TCTCTGATAA
12201 TTCTTTCTCT ATCTTCCAAA GTCTTTCCCT TGGGGAGTGT ATCCTGCTTC
12251 ATTCGTGGTT CCAAATATTC CGACACACAC TGATGCTTCA CCATCTTCAG
12301 CTTCTCACTC AGGCATCTCA GCTGAGTGCA GGACATCTCC ACACATCTCC
12351 ACTGACTGTC TGTCCTGCTG TCAGCTCACA GTCAGACCTC TTCTGTCATT
12401 ATTCAGCTTT GTTTTTTCTT TTTGCCTTCC ATCTTCTCTG GCTTATCTGC
12451 CATCCCTTTG AAATTTCTCT TACATGTGTT CCTTTGACTC AATTTCTGTT
12501 GCCATCACTT TAATCTAGGT CCTCATGTTT TTATGCTTTG ACCACTGTAC
12551 CAGCCTTCTA ACTGGACTCC CAAGTGCCTC CAAAATTCCT GTCTCCACTT
12601 ACATCAATTG CTAACTTTCG AAAAAAGTTG GTTTTATCAT ATCACCCTCC
12651 CCACCAGCCT GCCATTCTGA GCTCTCTAGT ATCTGTTCCA CGTGTCGGTA
12701 AAAACTTATT TCCCATCATT TCCCACAGAA GCCCTGCACT GTCTCTTCTA
12751 CCCTCTGAGT GTATCTCCCC ATTCCTGATG CCAGCCCTTA GAACATCAGT
12801 TAACCAAAGG AAGAAGAGAT ACAGAGCCAG GAGAGCTGAA GGCCTGGGGG
12851 AGGAGAGGAA GTAAACTGAA ATCATTCCAT TAAGGGTGTG ACTTGAGGGT
12901 GAGGACATGA CAGAACATGC TTTAAAATAC TATTATAATG ATGAGAAGTT
12951 GCAGAAGGAA GGAGGGTGGG AGCTGGAGTA TGACCTTTCG TGTTTGATTA
13001 GTCTGAACTC TAGACCAAAA TGGTTTCATT TAAATTGGCC TGAAGTTGCC
13051 TGGAGGCACT GCTGTTTAAT CAGAAGGGCC AGTCCCTCTT TGAATTTTTG
13101 TCTCTGCCAA AGACAGCCCA CATAACTAGA CAGTGGACAA TAGGATTCCA
13151 GGGAGAATAT CTAGCCTTTA ATATAGCCAT GGCATTGGAA AGTGGAGACC
13201 CCCTCCTGTT TTATTTCTTG AAGGAGGATG TTGGCGATAT GCAGAGCAAA
13251 GCTCTCCACT TTTCTTAATA GCTTACGTAG GTGCGTAAAC ATTGTAAACT
13301 CCCTTTCATA GTGATGCCTT TGAGTTGTGT GTTAGAAGTA GATTTAGGCT
13351 ATAGCTAGGT ACTTTTATAA AATCAGATTT TAAAAAGTGG ACATAGTACA
13401 TCCAGTCTAG TAGATCATAC CATCTACTGT CATGTAATAT GGCAAACTGT
13451 ATCATTGTCA CTTCAGTAGC TCTGTCAAAA GTGCTGGACT GGAAGGCAAG
```

FIGURE 3E

```
13501 AGATCCATGT TCTTAACCTG AGTCTGTTAC TAATTACACA CATGACCCCA
13551 GGCAAGTCAC TTAACCTTTT ATGGTGTCAG TTTCCTCATC TGTTAAATGA
13601 AGGGATTAGA CTAGATTATT TCCAGGACTC CTTCCGAAAA AGTACAGGAG
13651 AGAGTTGTAT AACTGAAAGG CAGAAAGTGG AATAATTGAG GCTTGGAATT
13701 CAGGGTGACT TAAAAATTAC TTTAGGCTGG ACATGGTGGC TCACACCTGT
13751 AATCCCAGCA CTTTGGGAGG CTGAGGTGGG AGGACCACTT GAGCCCAGGA
13801 GTTTGAGACA GCCTAGGAAA CACGGCAAGA CCTTGTCTCT ACAAAAAATA
13851 ATTAAAAAAA AATTAGCCTG GCATAGTGGC ACATGCCTGC AGTCCCAGCT
13901 TCTCAGGAGG CTGAGGTGGG AAGATCACTT GAGCCCAGGA TTACAAGACT
13951 GAAGTTAGCT ATGTTCACAC CACTGCAGTC CAGCCTGTGC CACAAAGTGA
14001 GATCCTGTCT CAAAAACAAA AACAAAAACA AAAACAAAAA AACAACTTTT
14051 AAATTTTAGA AAACAGGTCC TGGATGTGTT TAATGTGCTA TATCACACAC
14101 TTAGTGGTTA CATTGGTAAA TGCCACTCCA TCTTATTGAT GTCAATTCTG
14151 TTTGCTGTAA ACAATTTAAT AACGTTCATG ACAGAGTCCT ATCAATACTT
14201 TGGAAGAGTG AGAGTGAGGG TTTGGTGAAC AGACAGACTA ACTTTGTATT
14251 TTGTTGGGAT TTTTAACAAT GAATGCATGT TACTTTTACC ACGTAAAAAG
14301 TAGCTCATAA CAATTTTTTT GAAATTATTT ATTTTCATTA ACTTTTATTT
14351 TAAGTTCTAG TGTACATGTG CAAAATGTGC AGGTTTGTTA ACATGTGCCA
14401 TGGTGGTTTG CTGCATAGAT CATCCCATTA CCTATGTGTT AAGCCCAGCA
14451 TCCATTAGCT ATTCTTCCTG ATGCTCTCCC TTCCCCCACC CCCATTCACA
14501 GGCCCCACCC AGTGTGTGTG GTTCCCCCCA TGTGCCCATG TGTTCTCATG
14551 GAAGAATTTT TCCTAAAAGA ATTAGTCCTG GGGAAAGAGG TGCTGTGTAA
14601 TCTTCAGAAC GTAATAAATG GCCATTCTGC TATCTCATAT GTTCAACACT
14651 TTCTGCAATG CTTAGGTGGC TTAGTCTCAC TCCTGTCCAT GTATGTTTTT
14701 TCCAAGGCCA AAAATTTTTA TTATTTTGTG TATCTGTCCA TAAATGAGCC
14751 AAAATGTAAC TAACTGAATG TGTGATATGC ACAATAGCAG TTTTTTTTCC
14801 TGATAATAGG TATTAGTTGA TAGCTGCAGT TGAAATAGTC TGAGACTGGG
14851 AAAGGAAACT TTTCACATTT AAGTATGACC AAGTTTAGTA AGTTCTAAGA
14901 TGTTTCTGCT TCAGTAGCAG TGCAATTGAC TTTTGGAGGG AGGAGAAAAG
14951 CTTCTAAAAT TATTGGTTTC TACGTGTTAC TGTCCACTGG TGAAGGTCAG
15001 ATTTCTTTGG ATATTATCAT GTTTTCCAGT AAACTTTGAG AAGTGTGCTG
15051 CTTCACAATT TTATCCTAAT TCCCTGGGGT AATAATTGAA AACTTCATAA
15101 ACATATTTTT AAAATTTTCT AGATCCTTAT GATTGTTTAT ATGCTTAAAA
15151 AACTTCATAC TAGATATTAA TTTAAAGAGG TCAGTAAAAC AAAATGGTGA
15201 ACTATGTGTC AGTGGAATCA AACTGTGAAT CATTTCTTTG CCCAGTTTCG
15251 TTAAAATATG TGATCATGTG AGTCTTTAAC TGTCTGCTGA AGATCAGTGC
15301 AGCAGGCCAC AGACTGTTAA ATACATTTCT GCAATATATC GGGGGAGGTC
15351 AATTTCTTAA TATCTTTGTT AAAAAGTAGA AGACGCAAGT AAACTAGATT
15401 TCATACATGT AGTCTTGGTT GGTAGTATCT CCTGAAGCAT GTGGAGGAAA
15451 ATTGGTAGAT CGAAACAGAA TGATAGCATT CAGAGTTCTC AGGGAGAGAA
15501 CCGATTTAAT CAAATAAAAT GGGCTTTGCA CATTTCGGCA AGTTCAAGAC
15551 ACTAAGAAAA GCCCTTGGGG AAGTAACTTT TATAAAACTG AATCCAAGAG
15601 AACTGGTTTT TCTTTTCTTT TTTTTTTTTT TTTTTAAAAT AGAGTCTTGC
15651 TCTGACACCC AGGCTAGGGT GTAGTGGCGT TATCGTAGCT CACTGTAGCC
15701 TTGAACTCCT GGGTTCAAGC GATTACCACT TGGGCTACA AACACATGCC
15751 ACTATGGTTG GCTAATTTGT ATGTTAATTT TTTGTAGAGA GAGGAGTCTC
15801 GCTGTGTTGC CCAGGCTGAT CTTGAACTCG TGGGCTCCAG TGATCCTCTC
15851 TCCTCAGCCT CCCAAAGTGT TGGGATTACA GGTGTGAGCC ACTGCACCCA
15901 GCCTGGCTAT CCTTTAAAAA GTAATTTTAA AGCTACACTA TACATTTAAA
15951 ACACAGAACA CTAAAATACC TCCTTTGAGC GTTGAAGTAT ATTAGTACCT
16001 TGAGTAAAGT GAGAAAAGCA CAAAAAAAGT GAAATCTGGC CAAATTGTTG
16051 GAGTATCAGG GAAAAAGTTG TGTCAGGGTC AGAAAATATA AGCAAGAAGG
16101 AAGTTTTTAG GGGAGGTACA AGAAGGAAGA CAGTTCCATT CTTATAATGA
16151 TATAATGTAT TCTTAGTGTG TACTTTATAA TTGTAACAAC CTCCTTTATA
```

FIGURE 3F

```
16201 GGTGTGCTAG CTGTAAAAAT CATTTTACAA AGATATTTCA ACAGTTTAAG
16251 GTGATTCAGC TGTCACAGTG TTCTGTTACC TAAGAGAGCA AGTAAACCTT
16301 GTCTTTGTTA TCAGAATTGG AGTCCATTTT AATTGTGAGA AGAAAATTCC
16351 TGAAGTTGAG AAGTTTTAAC TTGCCCAAAT ATTCAGGGCA AAGACCAAGA
16401 GAAAAGTCAT TTGTCTCCTC GGGAGACAGA GATGATTGGA AAAGCAGGGC
16451 TTCTTATTTT TCATGTCATT CCATCTCACT GGTGAGTTTA CCAATGCAGG
16501 AACAGTTTGT GATGACAGAG ATGACAGAAT GCTAAGTTGA AGAAGAAAGT
16551 GAGTTGGTTG AAAAATACTG TTGGAATTGA TTTATGCAAA TTTTCTGGGT
16601 TGTTTCAGAG CAAGTTTTCC CCAAACTTAT GGAGAGCAGA TGGAAAAAGG
16651 AAAATAGTTT ATCTTTCAAC AAGAGAAATG ATGGCCCTGC TAAATTTAGA
16701 CTCTGGCTTT AACTTGTGAC ATCTGGGAAA ATACTCAAAT CTGTTAATCA
16751 TTTAGTTTGT ATAACCACCT AGAAGAGCCC AATGTCCAGG ATAGACCTCT
16801 AACATGGGCT TACAAATGGC AGATATTACC AGGCTGATTT AATTTCCTTT
16851 AATAAAAGAT AAAAAGTCTT GTCAAGGAGA GGAAAGCAAC ATGCATTGGC
16901 TTTCTGGATG TCAACAAGGT TTTCCTTCAT TCATTGTGAA GAGCTTGCTA
16951 ACAAGCTAGG AAGATTTGGA CTGGACTGCA CTGCTCCTCA GGGGAATGTC
17001 CAGATAGGCT GCAGGATGTA TGTGCCTAAA ACAGGTCAGT GCAGTGGCTC
17051 AGCACCAAGT CAGGGGGACA CCACAAATGG AGCCTCCCAG CAAGAAGTTT
17101 TGTCACTGCT GTGTGAAGGA GCCTGGCTTG TGAAAATTCA TAACGTACAA
17151 GGATTCTTTT TACTGTTTGG AAAGATTCAT TGCCAGTCCC TTTAAATAGC
17201 TACCACCCTA GAGAATATTA ATCATTCAAC TATTTTTTTT TATTTATAAA
17251 TAGTCAATTC ACATACAGTT TGTAAGGGTT ACTTTTCTTG TGGAAAGTTA
17301 GGTACAGCTG CCCTAAATAT CTTTATCGGT TACCTTGGCT GGGGAAATTA
17351 ACAGCATGTT TATTAAACTT GTACATTATA CTGTGTTATA ACATTATACC
17401 ATTTTCCAAA TATTAGTAAG GTCGCTAACA TTTTGGAAAA GGATTACAAG
17451 TGACCTTTAG AGATAGAACA GGAGTTTTTC AGAAAGGGCC TCTAACACCA
17501 CTCCCACATC CCCTTCGAGG ACAGTTGATC TGCTTTTATC TCTTTTACTT
17551 GTTCTTAGTT CCTGGCAAGA TTTCAATGGA GGAAAAGGCT TCTCTATTTA
17601 AAAAAAATAA AAATCAATGA AAATTAATGA ATCGGAGAAA TGGCCTGGCT
17651 AAAATGGGAT GAAGTTCAGT ATTAGGATAC TGAGGGATAC TGAAGTTTAG
17701 GGGAGCCACT AAATAACACT CCTTCATTTC CCTCCTCCAC TTGAAATCTA
17751 TTGAGAGGTA AGACACAGAA GCCAGCCAGA GTTCCAAATT ACAGCTTTAT
17801 TCCTGATCAA AGCTGGAGGA AAGGATGTAG CCTACATGTG TGTTCTGAAA
17851 AGCTTCCAAG TAGTTCACAT ATTGACAGAC CTACCCTATG GGTCTGTTGT
17901 AGGGGTGGAA CCTACCCCTT TAGCACCACA TGTCAGAGAA CATACCAGAA
17951 TATTCAAAAG AGCTTCAGCA ACAGGCCTGC AGAGAGCATG CCAGTTTCCT
18001 GTTTGCAAAC CAACCAGTCA GATGAGAAGG TGGAAATGTG GGTGCAGAGG
18051 GTAATAGAAA ATATTGCTTT TAGGCTTTGC CCTTCTGAGG AGAAAAGTGC
18101 AAATTCTCTC CTTCCTGTGG TGATGTAAGT GGAGAATAAA TAGCTAGTGG
18151 CTAGTCAGAT CAAGCTGGGA CAAGAACCCA GGTCACTGAT AGAAAGGCCC
18201 ATGTTTTTCT GTTGGTATGA AAAGACATTT TTAGTTGACT ATGGAAACTT
18251 AAACCCGATC TGAATTAACA TATTGAATTA ACATTTATTG AGACAGGAGG
18301 TGTTCTCTTT CTGTAAGTCA GATTTACATG AAGGATTGTT ACAGGGTGTA
18351 GAATTATAAG ATACATAAGT CTGATTTATA TTAAAGGAAC GTATAGAATT
18401 ATAGGATATA AAAACTGCAA GGGACCTTAG AGTTGGTTTT TCAGCCCTTT
18451 CATTCCTTGG GTGAGGAAAC AGCCACAGTG GGATTAAGTG ACTTACTCTA
18501 GACCACTTGC CAAGCGAGTT AGTGACAGCT AGGAATAGAC TAGGCCCTTC
18551 TAATTCTTAA TTCACTGTTC CCCACACCTA ATTGTTCTGT ACTTAGATGT
18601 CAGGGAAAGT AGGCTTAAAT TAAAATGAAA TTTGAAAAAT TTATTAAACT
18651 TATAAACTAA TCTAACAAGA CATATTTGTG AAGTGAATAT AGGCTTACCA
18701 TGAAGATAGT GCAGGTTCAA TTCCCAGACC ACCACAATGA AGTGAGTCAC
18751 AAGAATTTTT TGCTTTCCCA ATTCATGGAA AAATTATGTT TACACTATAC
18801 TGTAGTCTAT TAAGTGTGCA ATAGCATTAT GTCTAAAAAA CAATGTATAC
18851 ACCTTAATTT AAAATACTTT GTTGCTAAAA AAATGTTAGT GATCAACTGA
```

FIGURE 3G

```
18901 GCTTTCAGCC AGTCATAATC TTTTTGCTGG TGGACAGTCT TGCCTTGATG
18951 TTGATGGCTG CTGAGTGATC AGGGCAGTTG TTGCTGAAGG ATGGGGGTGG
19001 CTGTGGNNNN NNNNNNNNNN NNNNNNNNNN NNNNNNNNNN NNNNNNNNNN
19051 NNNNNNNNNN NNNNNNNNNN NNNNNNNNNN NNNNNNNNNN NNNNNNNNNN
19101 NNNNNNNNNN NNNNNNNNNN NNNNNNNNNN NNNNNNNNNN NNNNNNNNNN
19151 NNNNNNNNNN NNNNNNNNNN NNNNNNNNNN NNNNNNNNNN NNNNNNNNNN
19201 NNNNNNNNNN NNNNNNNNNN NNNNNNNNNN NNNNNNNNNN NNNNNNNNNN
19251 NNNNNNNNNN NNNNNNNNNN NNNNNNNNNN NNNNNNNNNN NNNNNNNNNN
19301 NNNNNNNNNN NNNNTCATAA GAAACAACTC ATTCATTAAA GTTTTATTAT
19351 GAGATTGAAG CAATTCAGTC ACATCCTTAG CTTCACTTCT AAATCTAGTT
19401 CTCATGCTCT TTCTACCACT TATGCAGTTA CTTCCTCCAC TGGAGTTTTG
19451 AACCCCTTAA AGTCATCCAT GAAGGTTGGA ATCACCTTCT TCCAAACTCC
19501 TGCTAATGTT GATATTTTGA CCTCCTCCCA TGAATCACGA ATGTTCTTAA
19551 TGTCGTCTAG AATGTTGAAT CATTCCCAGA AGGTTTTCAA CTTTTCCCAG
19601 ACGCATCACA GGAATCACTA TCTATGGCAG CTATAGCCCT ACAAAATGTA
19651 CTTCTTAATA GCCTTACAAA ATGTATTTTT TAAATAATAA GACTTGAAAG
19701 TCAAAATGAC TCCTTCACCC ACGGGCTGCA GAATGGATGT TGTGTTAGCA
19751 GGCATGACAA CAACATTGAT CTCCTTGTAC ATCTACATCA GGGCTCTTGG
19801 GTGGCCAGGT GCATTGTCGA TGATCAATAG TATTTTGAAA TGAATCTTTT
19851 TTCCTGAGCA TTAGGTCTCA AAAGAGGGGC TTAAAATATT CGGTAAACCA
19901 TGCTGTAAAC AGATGTGCTG TCATCCAGGT TTTGTTGTTC CATTGCTAAA
19951 GCACAGGCAG AGTAGATGTA GCATAATTCT TAAGGGCCCT TGGATTTTCA
20001 GGATGGCAAA TGAATGTTGG CTTCAGCTTA AAGTCGCCAG CTGCATTAGC
20051 CTCTAACAAA AAGTCAGCCT GTCCTTTGAG GCTTTGAAGT CAGGCATTGA
20101 CTTCTCCTTT CAAATTATGA AAGTCCTAGA TTGCATCTTC TTCCTATAGA
20151 AGTCCGCTTC ATCTACATTG AAAATCTGTT GTTTAGTGTA GCCAATCTCA
20201 TCAGTGATCT TAGCTAGATC TTCTGGATAA CTTGCTACAG CTTCTATATC
20251 AGCACCTGCT GCTTCACCTT GCACTTTTAT GACATGGAAG TGGCTGCTTC
20301 TTCTAGCTTC AAAGTTTTCT TCTGCAGCTT CCTCACCTCT CTCAGCCTTC
20351 ATAGAGTTGA AGATTCATTC CATCAACTCT AGGAAGAGTT AGGGCCTTGC
20401 TCTGGATTAG GCTTTGGTTT AAGGGAATGT TGTAGCTGAT TTGATCTTCT
20451 ATCCAGACCA CTAAGTCTTT CTCCATCTCG GCAATGTGGC TGTTTTTCTT
20501 CTTACTCCTG TGTTTTCCTG AAGTAGCATT TTAAATTTTC TTCAAGAGCT
20551 TTCCTTTGTA TTCACAACGT GGCTAACTGG TGCAAGAGGC CTAGCTATCT
20601 CAGCTTTCGA CATGCCTTCC TCACTAAGTT TAATCATTTC TAGCTTTTGA
20651 TTTAAAGCGA GAGAAGTGCA ACTGTTCCTT TCACTTGAAC GCTTAAGAGT
20701 CCATTGTAGG GTCACTAATT GGCCTGATTT CAATATTGTT GTGTCTCAAG
20751 GAATAGGGAG GCCTGAGGAG AGGGAGAGAG ATAGGGAACA GCTGGTCGAT
20801 GGAGCAGTTA GGACACATAC AACATTTATC GATTAAGTTC ACTGCCCTCT
20851 TATGTGGGTA TGGTTCATGG TGCCCCAAAA TAATTACAAT AGTAACATCA
20901 AAGCTCACTG ATCATAGATC ACCATAAAAG ATATAATAAT AATGAAAAAG
20951 TTAGAAATAT TGCAAAAATT ACCAAAATGT AACAGAGAAA CACAAAGTGA
21001 GCACATGCTG TTGGAAAAAT GGCACTGATA ATACAGGGCT GCCACAAACA
21051 TTCAATTTGT AAAAAATGCA ATATCTGTGT GGTGCAATAA AGCAAAGCAC
21101 CATAAAATGA GGAATGCCAA TATACATAAT GTGTGGAAGA GTGGTTTAAA
21151 TTGGTGGGCT CTGAAGTTAG GCTATCTGGA TTCAAATCTT GGCTGTGCCA
21201 TTTCCTAGTT GTCTGGCCTG GACAAGTTAC CTCGCTTTCC CAAGCCTCAG
21251 TATCCTCATG TATAAAGTGA AGATAGTAAC AGCACCTACC CAGAGGGTGG
21301 TTGTGAGGTT CATGTAAGAA GGATGTATAT TACATGCTAT GCTTAGTATA
21351 AGTGAGTTCC TAACATATAA GCACTGATAA ATATTAGCTA TCATTAGTCA
21401 TCATCATGAT TATTTTACCT TGGAGAGACT TAAAATTTGA CCTGTGAAGA
21451 TAATAAACCC TTAGCTTAGG ATTCTACCCA TCCTAAGTTA CTCCTTTGTC
21501 CTAAACCTCC ATTCTTTAGG CCTCTTGTAA TATCTTTTAC TGTCTATCCT
21551 TTGGCCTCAT GCTCTATCAC CAAGTCTGTC CTATTTGTTT CACATGTTTC
```

FIGURE 3H

```
21601 TCATTTAACT CTTTCATCTG CATTTCCATC CTAATTCAGG TCTTGATTCC
21651 CCAGGTGTGG CTTACTATTC AAGCCTCCTA GCTGCTCCTC CTCCTCCTCC
21701 TCCTCCTCCT CTTCCTCCCC CTCCTCCTCC CACCCCCTTT TTTTTGAGAC
21751 AGGGCCTGGT TCTGTCACCC AGGCTGGAGT GCAGTGGCAT GATGGAGTGC
21801 AGTGGCATGA TCATGGCACA CTGCGGCCTC CACCTCCTGG GCTCAAGTGA
21851 TCTTCCCGCC TCAGCCTTCT GAGTAGCTGG GACCACAGGT GCACATCACC
21901 ATACCCGGCT ATTTTTGTGT GTGTGTATTT TTGGTAGAGA CAGGGTCTTG
21951 CCATGTTGCC TAGGCTGGTC TCGAACTCCT GAGCTCAAGC AATGTGCCGG
22001 CCTTGGCCTC CCAAAGTGTT GGGATTACAG GTGTGAGCCA TCGCGCCTGG
22051 CCTCAAACCT CCTAGCTTCT TCTGACTACA GCTTCACTTT CCTGCAGGCT
22101 GTCCTGTATG TCACTATCAG ACTGATTTTC CTGTTTACCC CTGCCTTGGA
22151 TTCTGTAGTG TGTCTACTGT CTGCTGCTTT AAGGCCAGGC TCTCATACCT
22201 GACCTTCAGG TCTTTTAGGA ACGTCAGTGT CCAATAGAAA TATAATGTCA
22251 GTCATACACA TAATTTAAAA ATTTCTACTA GCCACATTAA AAAGTAAAAA
22301 CAGGTAAAAT TAATTTTACT AAAATATTTT ATGTAACCAA AAATATCCAA
22351 GACATTATCA TTTCAACATG TAATCAATAC AAAAATAATG AGATTTTGGC
22401 ATTTTTTGTT CTGCATCCTC AAAATGCCAA ATGCATTCTA TACTTACATC
22451 ACATCTCGAT CCAAACTAGC CACACATCAA GTGTTAAATA ACCACATGTA
22501 GATAAAAGCC ACTGTATCAG ATAGTGCAGC TGTAGAATGT GACTTGCCAC
22551 CACATAAACA AGACATAACT ATGTTTCACT TCTTCCTTGT TTGTTAAAAT
22601 AGGGATGTTA ATGCCATGCC TATTTTATAG GGTTGTCCTA AGCCAATGTG
22651 AAGTGTGAAA GTGCTTTGTA AGCAGTAAAG TTCTGTAAGA ATGTATGGAA
22701 GTTATTATCA GGAGTGAAGG TTTTTACTAA CATAAGAATA CAATATCTTT
22751 GGAGTAAAGT AATTTAAAAG AAAAACCCAT ATTAAGGAGG CAAATTAGCT
22801 GTCCTGAATT CATTTGTGAA AAAAATTAAC TCTAAGCAAT GAATGGAGAG
22851 TGTAAATGTA TACTCACTAT CTCTTTATAA TTATCTTTTT GGTAGAAATT
22901 TATCACATTA ATAAGATTCT CTAAATACTT CAATAAATCT GTGGGCCTTT
22951 TTTCCTTCAG CATGTTGAGC AATGGACATA GGGACATTTG GTTCTTCTCT
23001 TGATATAGGG AGCTGGACCC CTACCAAAGA GTTCATTGCT CTTGGTAGTA
23051 AATGTAGCCT ACATACTTTG TAGTACTGAG GTAGGAGTGG CATTAAAATT
23101 TCCCATATCA TCCAATTCAT TGCAAAGAAT AGGAATTAAC CTACAAACAA
23151 TGTCAGAGAT TTAGATACAG AAACTATTAA TATTTGGGCC GGGCGCAGTG
23201 GCTCACACCT GTAATCACAG CACTTTAGGA GGCCAAGGCA GGCAGATCAC
23251 CTGAGCTCAG GAGTTCAAGA CTGCCCTGGG CAACATGGTG AAACCCTGAA
23301 TATACTAAAA TATAAAAAAT TAGCCAGGCA TGGTGGCACA CGCCTGTAGT
23351 CCCAGCTACT CAGGAGGCTG AGGCACAAGA ATCGCTTGAA CCTGGGAGGT
23401 GGAGGTTGCA GTGAGCCGAG ATCGTGCCAC TGCACCCCAG CTTGGGCTAC
23451 AGAGTGAGAC TCCATCTCAA AAAAAAGGAA AGAAAAAGAA AAAGAGAGAG
23501 AGAGAAGGAG AGAAGGGAGG GAGGGGAAGG AAGGAAGGAA GGAAGGAAAC
23551 TATTAATATT TGTAAAATGC TTTCATTTCA TATTCTGTAT TCTGACAGAT
23601 TGGTGAATAG CACCACTAAC GATAAGGACA CATTATTTTA AATAAAGATG
23651 AGTCATAAAG TGGTACCCAA ATCTTATCCT AGCCCTTTAC CAAACCAAAT
23701 AGTCCACTAA TTTTTAAAAA TTATACCTTG AACTACCACA TGGCCCTTCA
23751 GGTGTTCAAA TTTAATATAT AACCTTTGTT ACCAGTGTGG AAATAAGATT
23801 GCTAAACGAA GTGACTCCAA AAACAAGAAT CAATTTTATA TAATGGCTTC
23851 AGGGTAAAGG ACCCCGCCC ACCATTTACA AGTTTGCCAA AGCCAGAAAC
23901 TTCAACATAA TGCATGACCT TTTCTTTCTC ACCTGTCCCT CTAATTAGCT
23951 ACTAAATCCT TAGGACTCCT CCTCTGAAAT ACTTCCTTAA TCTGCAACCT
24001 CCTCTCCATC CCCACTGCCC TAACTCAGCC TTTCATCACT TTTCTCGTAA
24051 GCTCTTTCAG CAGTCTCCAA ACCAGTTTCC CTGCCTCAAG CTTCAGCCTC
24101 CCCTCCACCC CACAATTTAT TCTCCAACTA CCAGCAGAGA TCTTAGTAAA
24151 ATAAAGATCT GATCATACCA CTCCCCGGAT TTAAAACCTT GAGTTCTTCC
24201 CAGGGCCAGC AGATAAAATC CAAACTGCTG AGCATGGTGT ACAAAGCACT
24251 TTATAGTCAG AGCCCAAATT ATCTTAATCA GCCTTGCCTC CTGCCATGTG
```

FIGURE 31

```
24301 CCCAGAGCAA TGATAATCAG ATTACTGGTG GTTCTCAAGT AAGTCCTATC
24351 CTTTTATCTG TTCTCTTCCC TTGCACAGTC CCCTCCACCC CTCACATCAG
24401 TGAGTCTCAT GATCTTCACT CCATCCCATC AGTATTTCTC AAATGTCCCA
24451 CTTTTCAGTG AGAAGCCTTC CCTCACTCTC TGGTCACTTG TTCTTTCAGT
24501 CTCCATAAGT GCATCTCTTA TTCCTTTGTG GCAGGAACCC CTCAAGAGCT
24551 AATTCCTCTC TATATCCCCA GCACGTAGCA TTCTGCCAAG TATAGCATAG
24601 TTTGTCAGTA AAAAATCTGT TGAATAAATA CATGAAAAAA TTGATCCTCT
24651 CCACCCAAAT GTACACCTTT CTCTTCTACC CCAAAGAAGA AATCTAATTT
24701 CCTAATTCAG TGTGATTTAT AATCAACTAC TGATAGTTCC AGGTATTTGA
24751 AAAGATACTT TAAATCATAA TGCTTCCTTT TCACTAAAGT TCAGTTTATC
24801 TAGTCCAATA AGATTTTCCT TGGGCCATAA AGAGTTATTC TCATTCCCTA
24851 TATTTCCAGT ACTAAAAGTC ATATATACAA TTTGGCCAAA GGAGCACCTG
24901 GAAAGTTTTA ACCTTTAAAT GCTTCGACCT ATAGGATATG TTAGGAACAT
24951 TAAAATAAAA GACAACAAAC TAAGCACATC TTTAATTTCA CAAGAATTGC
25001 CAGCTATTGG ACCTGGAGTG AATCTTAACC AAGATCACCT TCACCTTGAA
25051 GGGTTATGCA GGTTGTGTTC TGTTTAACCC TAGGGGGCGC CACTCTCACA
25101 GATTATGATG TGAATGACTG CAAGGTGGTA TCATTCTCAG CCTTATACAG
25151 TGTCCCTGCT TATCAGATCA TCCTCCTTTT CAGCTTAGGT CCTAAGAAGC
25201 CAACTGGTTT GCTCAAGGTC ACACAGGTAT TTCATAACAG GGTTCATAGC
25251 CAATAACCTG CCCCCTTTCT TACTTCCCAG TCATTCTACT AATCCAAATT
25301 GCTCTGGAAG ACCATGAAAC CAGAAAAGAG TGTTTGATGT AGTTGCATGG
25351 ATAATGGACT ATATGCCTTC AGCTAAATGT GAAATTCAAA TGGTTTGGTT
25401 TATCTCGGTA TCATTTGCTC TTGTTTTCCA CCTCTAGCTG TACTGGCCTG
25451 GTTGGCATAA CTTCAGCATT TAGCATATCA CACTGCTGCT CTCAGGCTCA
25501 CCGAGACTCA AGTGGCTGTT CCACTCTGTT GCCACGCTGT GCTGTCTTCT
25551 CTCTTTCTTG CTGGCCCATT CCTCTGTGAC TTCCTGTTAG CTGCCACCTT
25601 CTTCTTTTAG CTTCTCTTCT CAGCACTTTT TGCTGCTTTG TTTTTATACC
25651 CATCTCAGAC CAGTCAGCAC GATCCTTTCC TTCCTTCTAT TCTACAAACC
25701 AATCAATCAC AGCATGTTGG CTGTTGACCT TGGATCTTTG GTTGTTTGCT
25751 GCTGTTCATA GCTGCTGGGC GTGGCTAGGG GATGCTGCTT CTTTGCCAAA
25801 ACTTTTTGTT TCTTTTTCTT TCTCCCTTTA TTCTAGATCT TGGGCTTTCT
25851 GAATGCTTGA AGATACCAGA AGGGTTATAT CCAAATAAGT GTGGCTCTAT
25901 TCCTATTACT CCCTCTTTAC TCTTGCTTAA AAGTGAAAAT ATTGCTTCGG
25951 TGGAAGAATC TTGGTTAGAA GAATTAATGT AGCTCAGACA GTCAATATAG
26001 CTAATTGTCT TTACCAAGGA CAATGCATTT AAAAAATAAC TACTCCTTCC
26051 TCTGCCCCTT ACTCCCATGC TCACCATCAA TGTGAAGCTA GGGTAACAGG
26101 TGTGTTGGCA GGTTTGGTTG AGCCTGAACA GAAAACTGGA CCTCTTGAGC
26151 CACAGTCCTT CAGCCATAAT GGACGAAGTA TTTTTTGCTT CAGTTCTTTG
26201 CGCTTGATCA TTAGAGCTAG CAGGTCTTTC CGAAACTGCT TGCTTTAGTT
26251 CTACCTGATC AGTGAAGATA TAGAATAGAA TTAGGTTAAA GAGTGGTTAA
26301 TTTTCTTAGAG TTTTGATACT TGCTGTTTAG TGATTGTACT TTATATATTG
26351 TTCATTGTAT AATCAAGAAA TTCTTTGTAA ATGTTTGGTT TGCAGGCTGG
26401 TTGGAAGGAA AATCATGCAA CATTCATGAG CGAACTAAAA AATCTTCAGG
26451 CTTCTGGACT GACTACTCTC GGTCAGGCTC TAAGATCCTC ATTTGATTTG
26501 TTAAATCTCA ATAGATTAAT ATCTGGAATA GACAATTATG GACAGGTAAA
26551 AATAATTTGA GTGAGTACAG CTAATTTATT TTGGTGGCTT GGGGTAAGAA
26601 TTTAAAATTG GGCATGATTA CTAAGTTTTC TGCTACTTTT CATAACCTCC
26651 AAAAATGAGA TTCTTATTAC CTTTTAAATA TATACTTTTT AAAAATCCCT
26701 CTTCTTTTGG TTCTTGTATA TGGCTTGATA ATAGAATAGC TAAAATTGTC
26751 TACCATGAGA TAATCAGATG TTTGAGAATG ATGTGAATAA ACGGCTGAGA
26801 AATATCGGAA CAAGACAATT GGAAAGAAAC TTTCAGTGTC CTTAACTCCT
26851 CTGCCCCTCC CAATTTGATG AAAAAGCTCT AGGATAAGAA GGCAGAGTAG
26901 CATTTGCTGT TGCTCCCATT GTCCTTTCCT CCTCTAAAGT CTGTGCTCAC
26951 AGTAACCAGA GTCACTCTCC AGGTTGCAGC ACGCAAGTCA CTAGTGTCCT
```

FIGURE 3J

```
27001 ATCTGTGCCA GGATTTTGAC TTAAGTGAAT GGATTCATGA GAGTGGATGA
27051 TAATGCCAGT AATCTTGTAA TATTATTTTG TGATTACTTG GAAAGCAGAG
27101 TGAGAGAGGT ATTTGAATGT TAATGGTTTG GGGAGTTCCT GAATTATAAG
27151 AATTCCTCAG TTTATACTGA ATGTTACCTC TTCAGGGGTT GTTATTTTTA
27201 TTCCTACCCA TTTCGTTCCC TGGTCATTTC TTCCTTATTT ATCCAGACAA
27251 ATTTTATCAT ATTCTTGAGA GATCATTGGC AAGGCAAATA TAAAAATTTA
27301 AATATACTTT TATTACTTTA CATGGCTCTA ATGCTTTTTA AATGTATTTT
27351 AGGGGAGAAA TCCATTTTTT TTAGAACCAT CTATTTTAAT TACCATCACA
27401 GATGGAAACA AGTTAACAAG TACTGCTGGT GTTCAAGAAG AGGTGAGATT
27451 TTATTTTTTT TTTAATTTTG TTTAAATGGC AGGGAACATG CAGCTATTTC
27501 TGTGGGAGGC ATTTCCAGTT AACAGTAAGT TTGGTCAAAT CATCCATCTT
27551 GGTAATCCTT GAAAGACTGC TTAATTTTAT TGAGTTACAT GAAAGAAAAA
27601 GTCAACCCTT TAATTCTTTC TTCATTTTTA TATGGTTTGT TATGATGAAC
27651 CTTTTCACAT TTTTGCCTTA TCAGCTCCAT CTTCCTTTGA ATTCCCCTCT
27701 GCCTGGAAGT GAACTAACCA AGAACCTTT TCGTTGGGAT CAAAGGTTAT
27751 TTGCCCTGGT GTTGCGTTTG CCTGGAGTGG CTTCTACCCG AACCAGAGCA
27801 ACTAGGGAGC GTACCAACTG ATGAATCTGC CATCACACAG AATGTGTGAA
27851 GTCACAGGAG GTATTGGCAA TATTTAATGT TTCTGAAGGA AAAATTCAGA
27901 GCATAGAGTA TATTTTTCAT TAAATGCCAT ATCCAGTCTT TACTTGTTTT
27951 CCTTCAAAGC CTTTTAACTC TGTTGCTTAA GGTCATCATT GGTATATTTG
28001 CTGCCAATGT AGTTATGATT ATTTCAAGTT ATATTTTAGG ATTTTAAAAT
28051 GCTTATATTA TGAAATTATA TTTGATCAAA CTTGTGCTAT TTATTTTTCC
28101 TTCTGGGATA GGTCGCTCCT ACTGTGTGAG AACACAAAGA ATGTTGAATC
28151 AATGTTTAGA ATCTCTAGTT CAAAAAGTTC AGAGTGGTGT AGTTATTAAT
28201 TTTGAAAAAA CAGGACCAGA TCCACTTCCT ATTGGAGAAG GTATAGTAGA
28251 TAACTTTTTT AACCCTAAAG TGTTATATAG GAGAATGAGA AGACATTAAA
28301 TAAATTACTA TAGACACAGT CTTCACTATC CACGTGCATT TGAGTGGTTA
28351 CAAACATACA TCCAAACAAC TACCACACAT TCACTGCCTA TGTATATGTA
28401 TCAGGTGGCC AAATTCTAAC AACTTTAATT TCATGTTGAA TGTTCCTAAG
28451 AACGTGTTTC CTTTTCCTGG TGCATTTTAT ATTCCCTGGT CCCAGTCTTT
28501 GGATGGCACT GACTCATTCA CCTCTCTATT CACAAAATGT CTGGAGATTC
28551 ACTATGGTGT ACACTTAAAT AATAATCTTG TTTTGGTTTT GTGAGTGCCA
28601 AATATGCTAA GCCATCTTTA CGAAATATGT GTTAGTTTCT GCACCTCAGC
28651 AAGAAATTAT GAATGTTTAT CCAGGAACTG CTCATCTTCT CTAAGATCCT
28701 ACACTAGTAT TTTCCCGGTC ACTTTTTCAC TCTGAAGTTA AGAGTTGAGC
28751 AACCTTTTCT CCAAATGAGA TTTCACAGAA AGTTCGACAT CCAAAACTTG
28801 ATGAAAGTAG GGTGACTTTT GCATAGGGGA AGTTAAATCG TAGTGAATCT
28851 CTAGATGGTT TGTGAATGGA TGTTTGTAAT CACTTGAATG CAAATGAATT
28901 TCAAAGGGAT CAGGGAACTA AACAAGCACC ATGGCAACGC ATTGCAAGAC
28951 TTCCATGGTA ATGCACTGCA AGAACAGAGC TCCTAGAAAG TCTATGTGTA
29001 TATGTATGTA AATTTGTAAG TGTATATATA TATATATATA CACACACACA
29051 CTCCATTATT ATTACCACAG TGATTGTCTA GCCTGATTTA TATGTTTTAA
29101 TTGCCTTGAC GAAGAACAAA GGGGTCAAAT GCATAAGGGC AGAAAGCTAC
29151 ACATTTCTGT CTGAAGCAGT GGATCCTGTG GCTCCTGATC TTTTGTTGTT
29201 GTTGTTATTG TTGTTGTTTT GCTCTTTAGT TCCCCATCCT TTTGAGAAGC
29251 TGTTGGAAAA AATATAGACC CCTTTTCCCT ATAAATACAG ACATAAGTGA
29301 CACATTTCAC AATTTTGTAT ATAATCTCAG GGGTTTTTTG GGCCTCCAAG
29351 TTAAGAACAT CTTGCCATAA AAGACTGAGG GCCCACAGC CTATTTTAAA
29401 TTAACTGTGT AGGAAGGCCA TGTTATACTG CTAGCAATCC AAAATTTCGT
29451 GCTCACTATC TTAGCATAAA CTGGGAACTT ACATATTGAA ATTCTAGTAG
29501 GATTTGGTGT CATGTAAATG GCACAGATTT TTTTTCTAGC TCCAGTTCTC
29551 CTTTGTCCAG AGTTCTTAAC CTTTCAGGTT CTGATGAAAG TTAAGAACCC
29601 TTTTCCTCAG AAAAATGCAC ATTGTCAGAA TTGTGAGCTC AACTTTGGGG
29651 GGATCCTCCA AAGCCATTAC ACTTTTTTTC CCTACTGCAC AGTGGACCCA
```

FIGURE 3K

```
29701 TTAAATCTCC TAGTCTAAAG AAATTACTTG TTTAAAGTAA TGCTTAAATA
29751 AGTTATTCAA ATGACTGATA ATTTAAGAAA AATGAGACTC AAATCATTAA
29801 AGCATATCTT TTACAAATAT TATCATTAAA AGTTTATATA ACTCTGCCTT
29851 GCCCTGATTT GAGGCGGGGG GAGAAGGAGG AAGGAAATGA AATATGCTAG
29901 TTTAAATCAT TAAAATGCAT TCAGGATACA TTATTCAGCA TTATACAACA
29951 CCCATTGTCC ATGGAATTTT GATGGTGGAT GGAGAAACCA TAGTGAATTA
30001 GTCCACGATA AACTTGATGT GTTTGCTTTG TGCTCCCCTC AACTATATAC
30051 ACATTGTCTG CATTTCTTCT ATCTTTAAGT GAATTTGGCT AGTTTTTATT
30101 TTGCCTTTGT GGTCATTGGG TCTAATTGTT TGGCAAAGAA CACTTTTTTC
30151 TTGTATTTGG AAATAGAAAG AATATATAAA TGGAATTTAT GATCTATTTT
30201 TGTCAGACTC CAGAAATGTA AAAACTATAC CAGGGAGTGA ACAATTTCAT
30251 TTGCCTAATT TAGTAATTGA ATTCTTGAAA AATAACTGTA GTGTTTTGAT
30301 GTTTTTAATT TATGTGTACG AGTCTCAGAA AATTTAAAAC TAGTTTTACC
30351 ATAGTTTTCT GCATAACTGC ATATTCTCTT ACTAGGTTAA GAATGGTGGG
30401 GTGGGTGTTG GGTTAGAAGA GATGGATTAG ACGAAAAGAG TTGCTAGAGA
30451 GAACATTTAG AAATCCTAGT AGAGTCACTT TTTTTTCTTC TTCCATTTTT
30501 CATGAATCAT TGTTCTTGTT TTATTTTGGA CTTTGCTTTC AGCTGGAAAA
30551 TTTGTACAAG AAGATCAGCA GCTGTAAAAA GAAACTCACG CCTTAGTTTG
30601 TCTTTTGTTT AACTTTTAGA TGGACTTATG GATTCATCCA GGCCAAGCAA
30651 TTCATTTGCT GCTCAGCCAT GGCATAGTTG TCATAAACTC ATTTATGTAC
30701 GACCTAACTC TAAAACTGGT GTTCCTGTTG GACATTGGCC AATTCCAGAA
30751 TCTTTTTGGC CAGATCAGAA TTTACCTTCA CTAGTAAGTG TCATAAAATA
30801 AAAAGGTAAA CATCATTCTG GATTTTCAAT TTTCTGATTA CAGTGAACCT
30851 TTTAAAATAG CTTTGAGGCC TTTATGCCAT GCCACAGGCA AGTAAGTCTT
30901 CCCTCCTTTG CCTTCTGTCT CTTACCTGGG AAGTCTAGCT TTGTGCCTAA
30951 AAGCAAAGGG AGGACTTCCT TTATTTTCTG ATACTTGTCA TTCTTCAGTT
31001 GCCTTCGCCA CTTGAGCTGC CCTTTTTGGA TGTTAAAACA TTGCTGTTTT
31051 TGATGCTGTT ATAATCTGTT ACTTGGTTTT CATTTCAGAG CAGCTGACTT
31101 GATTTACGTG GCAAACACAA CGTCTAAAAT GTACTGGCCT TGGTTTTCAT
31151 GCACAGCCTC AGGAAGTTTG AACATAGTTT ACACCTTGGA TAGGTTCTGG
31201 GAACATATTA AAATCATATT CAAAATTCTA CTTCTTCCTA CTTTTCATCT
31251 TTTTGTAATC AATGGACTTT TGTAGCAATA TACCTTTCAA TGATGGGTAA
31301 TTAAGCAATA TTTAAAAAAT AATCTCTAAG CAAGGACTTG TCTTTTTGGT
31351 CACTGCATTT GTAGGAGAG GCTTTGCTAT TACAGTTGCT CCCAGTGCCA
31401 GATCAATTGG CTTTTTTTTT TTTTTTTTGG AGGGAGGGCA GTGTCTAGTA
31451 ATAAAGGAGA CGGTATGAAA CCCACTCTCT TTTGTCTTCT TTCCCCTTCC
31501 CCAAATTGTA AGAGGGCCTG AGTAATCTCC CTTGTGTGGG CTCAGGAGGG
31551 GACACAAACA AATCACTACT TCTTCTATTT AACATCTTCC TAGTTCAGTT
31601 CATCTATATT CTGTCTCAGT TTTAGAAATT TCTGACAGTG AATTGCATTT
31651 TCTCCTGGAT TACTGCTTTT AGGCTTCTGC CCTTTTTTCA GAAGTGGCCA
31701 TGAAAGACCT GAATGTAAGA CTGAAGAGCC CTTTTGGCCC CTGCTGTGGG
31751 TGAGGGTAAA CGTCCCACTC CTCTCCTCAG GGCTTCAAGG TGTTACACCT
31801 GTGAAACCTC AGCCCTTCCA AACTCGAGTA CAGGCTTTAT GGCAAATTTA
31851 CTTCATTTTT GCTAGCAACA AGTCTTCATT CATGTCTTTA TGACATTTTT
31901 ACCTGTTCAA ATCTAAGGAG TCAGAAACCT TTCACAAGTT AATTAAAACT
31951 AAGTTGGGAA AAAACAAAAT AGAATAAGAC ATTCCAAGTA ATTCACACAT
32001 AGCTCATGTT ACCATTCCTC CATCTTTAAA AGTTCATTTA AGAGCTATTT
32051 TTCTCAACCC CCAAACATCT TATAATTGTA AACTATAAAG GCAAGTGAAT
32101 ATGTTTTCAT TTTTTATAAA GGAAGCAGTG ATATTTTATC ATATTCATAT
32151 TAGCTTTACA GGTTTCGCAA CAAGAATAGG CTGACCCACT TCTTACTTTG
32201 TCTTCTGGGA CTTGTCCTGT GTCCCTCTCT CTCCATATTG CCCTTGCTGT
32251 TCGCCTTTCT CTCTCTGGTG CTCTCCAATC ACACAAGCTA AACCTGTTAC
32301 TTAAATGGCT TCTCCATTAA TCTGCTCCAG CACCCCAGGT ACACAGGCCT
32351 TCGAAGCCCA GCGCAAAGNN NNNNNNNNNN NNNNNNNNNN NNNNNNNNNN
```

FIGURE 3L

```
32401 NNNNNNNNNN NNNNNNNNNN NNNNNNNNNN NNNNNNNNNN NNNNNNNNNN
32451 NNNNNNNNNN NNNNNNNNNN NNNNNNNNNN NNNNNNNNNN TCAACATTCA
32501 TCCTACAATC ATAAGCACTT CTTAAACATA TTCAAAACAG TTTTTTTTCA
32551 ATTCACTGAA ATTTTAGTTA TGAGTGTTGA AATTTACCTT TCCTCTTCCT
32601 AATGTCAAGT AGATAGTAAA GAATCTGAGC CCTCTCTCCC ATGGAAGCCA
32651 TTGGTGGTTC CTAGAGATCT AGTAATCTTC TTTCTCAAAA TGCTAGTCTG
32701 TATTTCAGTG AAAATGTAAC AAAATATAAA ACGACTTGCA GAATTGTCAG
32751 AAATATAAGC TTGCTTTGAG ACCTAACCAT TTTTTCTGCT TTTTTTAAAA
32801 AATTTTTTTT AGCCTCCACG AACATCTCAT CCTGTTGTGA GGTTCTCCTG
32851 TGTAGATTGT GAGCCAATGG TAATAGACAA ACTTCCTTTT GACAAATATG
32901 AACTTGAACC TTCGCCCTTA ACTCAGTATA TCTTGGAACG AAAGTCTCCC
32951 CATACCTGCT GGCAGGTACT TATCCTTACC TATTAGCTAA ATGTCTGTAA
33001 CCACTCTAGG ATCTGGGAAT TGTTTTAAGA AGCTTCAAAG GTTATTCTCA
33051 AAATAATTGG ACTGACTGTG CTAATGATGT TTCTCATGAA TGCTGTCAAA
33101 TAAGCAACAG GGCCAGGCAA ATAATTTCAG ACTAATATGA ATCATTAGTC
33151 TACTGTACAT TGCCATTTAA AGCAATAGAG TCTGATGAAA CCTATATATT
33201 TGAAGATTTG GGGGACCCCT TGAAGTCTAC CCATGCACCC CAGCTTAAGA
33251 ATCCCTAATC TAAAGGTTGT ACTTCACTTC AGGTATGGCG TCTGCAGCTG
33301 AAACAAGGTG TTTAGCCCTT ACTTTGAACT TGACAGATTG GAAGTACAGG
33351 ATAGTTTAGG CAGAGAACCA TAAGTCCTGA AACTAATTTC TGTATTAGTG
33401 TAATATAATA AAACTCTTCG TCCTGTGGTA CAAATCACAC TAAAAAATGT
33451 GTGTAATGTG GATTTTGCAA CTTGGATGAG ACAAATGCAT AGAGATATCT
33501 ATCATACACT GGCTCTTCCA AGTGTTACAC TTAAGCCAGA AGGATTTGCT
33551 GATTGGTTAA TAGAGTCACC TATGGAATTT AATTTGTAAA AATTCAGAGA
33601 TGGCAGTCAC AGCCTTTTTA TGTGGATACA ACAAAAATGT CCTACACTGT
33651 AAAGATGTAT GTTCTATTTC TAAACTGTAG AGATGTATGT TCTACTTCTA
33701 TTAATATATA GGACTCTATA GCAATCAGTA ACTGTTAGGC TCTATTTATG
33751 CAAGGAACAC TTTCAGACTG CCATCTGTTT TATCTTAAAA TGTGAGATTA
33801 TTGCTACAAG TTGTCTGTAA GCTACTTAAA TTCTCCCAAG ATGCTACAAC
33851 TAGTTAGAAA AAAAGGAGCA GGATTAAAGC AAGAATGTAA AAGCACAAGA
33901 AACAGAATAA TCTCACAAAC ATAATACTGA GCAAAGAAGC TAGACAGAAA
33951 AGATTACATA TTGTGTGATT CTATGTTATA TACTTTCAGA GAGAGATAAA
34001 ACTAACTTAC TCTGTTAGAA GTCGGGATAG TGGTTTCTCT TGGGGGGATG
34051 CAAGGTAGTG GACAGAAGAG GACACAAGGA GATGTCTGGT TTTGTTCTCT
34101 TTCTTTCTTT CATTCTTTTT GTTTTGTTTT GTTTTGAGAC AGCGTCCAGC
34151 CTGTTGCCCA GGGTGGAGTG CAGTAACACA ATCTCAGCTC ACTGTAGCCT
34201 CGACCTCCTT GGCTCAAGCA AAGCGATCCT CCCACCTCAG CCCCCCACAG
34251 AGGAGCTAGG ACTACAGGCA CACACCACAA TTCCTGGCTA ATTTTTTAAA
34301 TCTTTTTTTT TTTTTTTTTT TTTTAGAGAG ACGGAGTCTC ACCGTGTTGC
34351 CCAGGCTGGT CTCAAACTCC TGGGCTCAAG CAATCCTCCC ACCTCGGCTT
34401 CCCAGAGTGC CGGGATGATG GCATCAACCA TTGTGCCTGG CCATATTCTG
34451 TTTTTTGACT CGTGTGCTGT TTACACATGT ACATTCACTT TGTGAGCATT
34501 CATTGAGCTC TATACTTATA GTTTACCCCA AAAGTGCTAG AAATGTAGAG
34551 ATATGGATAA TAGATTGCTA ATTTAAAATA AAGATATGAC CTTTGAATTT
34601 ATGGGTTGAA AAACATTTTT ATAATGAAAG CAAATAAAAT TACAAATTAT
34651 AGCTTTTCCC TAAAATAACC CCTCTTTTCT ATATAGCACA TTTCTTGGAA
34701 ACCTTCTTCA GAGAAACTTA AGAAATGCTG TCCTTGCTCC TGCACTACCC
34751 CTTAAATATG TCATATGCCT CTTTCCTGTA CTTTATGTTA CTTTTTTTAG
34801 AGTATTCTTA ATGTGATGAA TTAGTGTTAG TGAAAAAGAA TAAAATGAAC
34851 CAGTAGCCAG GAAATTTGGC AAAACCACAA TGGAGACCGG AGCCTAACCC
34901 TAGCTCTGTC ACCAACTATG TGGCCTTGCA CGAGGGACTT ACATTGTCTG
34951 AACTAGCTCT AAAGATCCTT TGGAACCCTA AAAATCTATG AATCTGTGGC
35001 TGATAAGGAA TTTGGAAAAA CTCAAGGGGC CAAGGAAGGT AGGAAAGAGA
35051 AAGAGAGAAA GAAACAAAAT TCAGTGCTTT TCCTTTCATG GGAATCATAG
```

FIGURE 3M

```
35101 ATCTGACCCT TGACTGCCTT GTGCATGTGA TTTTTTTTAT CTTTCTTTGA
35151 TGAATTTTTC CTCTCTTCTA ATATACACAC TTAGGAAATA AAATCCAGCA
35201 TGGTTTATTG CAGTTATCTG TTTCTATTAT CATTCAAATT ATGACACAAA
35251 ATCTAGTAGA CTCATGTTTT AGTACAACTC ATGTTCTGTG GGGTCATAAA
35301 TTACATAAAT TACATTACAT AATTATACCA ACTTATTCTT AGTGATAATA
35351 TTATAAGAAG GTAGTGAATT GGTAGGTGAT ATTGGTAGTA CTGAGAACTA
35401 GCAAGGTAAA TGGATTCTGT TAAATGTCAA GGTTCGACTT TGTTGTAAAT
35451 GATTCTGCCA AAGGACTTTG GAAAAGTAAA GGACCAGGTC TCTAAAAGTA
35501 TATATTGGTG GTTTGGACCA AAGACTCTGA ACATGGAACA GAGAAAACAT
35551 GGCAGCTAGG GGACCCCAGT ACAACATATC AACTGTAAGG GGGCTGATGA
35601 TACAGGAATC ACATCAGGAA ATCAATAAGG AGTAAGAAAA TAGTCATATG
35651 GAATTAAGAT CAATGTTTTA ATCTTCACTG AATGTTTACT CTACCAGCAT
35701 AACTTTTTTT TTTTTTTTTT TTTTTTTTTT TGAGACAGAG TCCTGCTCTG
35751 TTGCCCAGGC TGGAGTGCAG TGGCACAATC TCAGCTCACT GCAACCTCCA
35801 CCTCCTGGGT TCAAGTGATT CTGCTGCCCA GCCTCTTGAG TAGCTGGGAT
35851 TACAGGCGCA CCACTATGCC TGGCTAATTT TTGTATTTTT TAGTAGAGAT
35901 GGGGTTTCAC CATGTTGGCC AGGCTGGTCT GGAACTCCTG ACCTCAGGTG
35951 ATCCGCCCGC CTCGGCCTCC CGAAGTGCTA GGATTATAGG CGTGAGCCAC
36001 CGCACTCAGC CACTACCAGC ATAATTTATA AGAGAAATGC CTTCCAGGTT
36051 GACCCAAAGT ATCTCCTTGC TGCCTCAAAA TAATTAGCAC CAGTGCCTGG
36101 CTTATTATAA CAGGTTACTC AGTAAATATT TATTGAAAAA AAAATGGATA
36151 AATGGGTAGG GGAAGGAGGC AGCAAAGATG CATGGAGCAA AGACTTAATA
36201 ATAGTACAAT GAAGATGGTT TACATAATCC TTTAAGTAGG CTTTGTTTTT
36251 GTAATTTCAT GCTTCAGGCA TGGGACTGTG TTCTATTTTC TTCACAGTCT
36301 GCACTCTGAT TACCACTTGT TCTTTTGAGA AGTTAATTTG TTTTAGTGGC
36351 TGGTTTCCTC TTAGCAGTAT TTCAGCTTTA TTTTTCATTT TGCTAAGTAA
36401 GTAAATATTT GGGTACTGTT GATGTGGCCT GTGGTCTCTG AATGGTTGTT
36451 GCATAGTATA GTTTCATTTC TTAATATAAT TTATAGGAGA ATTGCGATCT
36501 GAACATTCAT ATTTAGTAGG ATTTTTTTTG AGACAGGGTC TCGCTCTGTC
36551 ACCCAGGGTG GAGCGCAGTG GCACAGTCAT GACTCACTGC AGCCTCAAGC
36601 TCCCTGGCTC AAGCCATCCT CCTGCTCAGC CTCCCAAGGG ATCTGGGGAC
36651 CATAGGGCAC GTGCCACCAC ACTTGGCTAA TTTTTTAAAT TTGTTGTAGA
36701 GAATGAGTAT CTCCCTTTGT CTCCCAGGCT GGTCTCAAAC TCCTGGCCTC
36751 AAGCAATCCT TCCACCTCAG TCTCCCAAAG TGTCAGGATT ATAAGTGTGA
36801 GCCACCTGTA ATCCTAGTAC ATGAGCCTGG CCTAGTATAA TATATTTTGA
36851 CATAACCATA GGCTAAAAAC ACTATTGCTA TTTTAAAATT ACAATCAAAT
36901 TGCGCCATAG ATGCTGCTAT GGAATGTTAC AATGGGTTTG GTTTGACATA
36951 AAATCCTTAT TGTCATCACT GTGCATTACT TCATGTTATT CTCAGGTATT
37001 TGTTACTAGC AGTGGAAAGT ACAATGAACT TGGATATCCA TTTGGTTATT
37051 TAAAAGCCAG TACAACTTTA ACTTGTGTAA ACCTCTTTGT GATGCCTTAC
37101 AACTACCCAG TTTTACTTCC TCTTTTAGGT AAGTAAAACA TGTGCCACTG
37151 AATCATCTTT AAAATACAAC AGAAATGAAA AATCGATAAT AGACTAAGCA
37201 TTTTAAATGT AGATGACGGT AACAAATTGA TTTGAAAGGA TAGAATTTGC
37251 ATACTGTTTT CTGTTTTGTT TGTTTTCTTT TTGTTGTTTT TACATCAAAC
37301 AGAAGAGAAG CTTGACTTTC AGTGTGTGAT TCTTATGCTT GTTCTTCAGG
37351 TTGCAACTTC CAATGCACAC CCCACCCCCA ATCCCCAGTT TGAAGTGCAC
37401 TTGGCTTTTT TGTATAGTTT GGGCCAAAAA ATACCAAAAC AGAGCTACCA
37451 TGGGGTGGGA GTAATGGCTT GTGCTTGTTT CCCCTCAGAA GATAAATGCT
37501 CTTGAGGCAT CTGTTTTAGG CAGAGTAGTG AGTTAAGAAA ATAGGTACCA
37551 GAGTAAATTC TGCAATGACT GTGGTTGTAG AAGCTGTGAT TTCCATAGCA
37601 AGGTTCTAAA AGGAACAACT CAAGAAGCTG TTACTCAGAT ACTAATGAAA
37651 ATGTGTGTGG AGATATTTTC CCCTTATTGG AAGAGCCACA TCTGTTTAGA
37701 GTAATGTAGT ACTTACTGCA CAGTATCCTA GTTGTAAAGT TGTAAATGTT
37751 TTTATTTCGT GGAGTTTCTT AATTTTTGCA AAAAGGGTCG AATCTTTACT
```

FIGURE 3N

```
37801 AAGTTTTCAT ACGATCATTA AAACTATGAG ACTTTTAGTG CTATAAATAC
37851 AACATACATT GAATATACTG AAATTGCAAT ACTTTTACAT GTCGATTTAA
37901 GAAGTTTAAG AATGAGTCAT CGTAAATGTA TTAGCATGAT TATTTTAAAT
37951 AACCTATCTA CTTTATTTCT TAGTGCAACC TAAGAGGGAT GTTCTCTTTC
38001 TAAGAGCTGA TTATCATTAA CATAAGATAT AGGTTATATC TTTCAGATTA
38051 ATAAGACAGC CAGTAAAAAA GTGTCTGTAT TTTGCAGATT TATTTATCCC
38101 TTTTCTTAAA TAAGTCTTTA TGACTTCAGT TTCCACAACT ATAAAGTGAA
38151 GAGATTAGAC TATGTAATCT TCACTACCAC TGTTAATGAT ATTATTTTTC
38201 TATTTTTAAG TGCACTTTTT TTGATCTACT TTATTGAGTT ATGCTTGACG
38251 TACAAAAAGC TGTACATATT TAATGTATAC AACTTGATGA GTTTGGAGAT
38301 AAGTATATAC GCATTAAACC ATCACCTCAT TCTATGCCAT AAACCTATCA
38351 GTCACCTCCA GAAGTTTCCT CCTGCCCTGG TAAGATCTAC CCTCTTACTG
38401 ACCTTTTAAG TACACAATAC AGTATTGTTA ACTGTAGGTA CTATGCTAGA
38451 AAACATTATG CTGAGTGAAA TAAGGCAGAC ACAGAAGAAC AGATACCACA
38501 TGATACCACT TACACACTTT TTATTTTGAG ATAATTGCAG ATTCACATGT
38551 AGTTGTAAGA AATAATATAG AAAGAGATGA CCTCAAAAGC ACAGGCTGCA
38601 AAGACAAAAC TAGACACATG GGACTATATC AACCTTAAAA GCTTGTGCAT
38651 CAAGGGAGAC GATTAACAGA GTGAAAAGGC AACCTATGGA ATAGGAGAAA
38701 ACATTTGCAA ATCATATATC TTATAAGGGC TTAATTTCCA AAAAATATAA
38751 GGAAGTCTTA CATTTCAATA GCAAAACAAA AACAAAACCC TAAATAGCCT
38801 GCTTAAAAAA TGGGCAAAGG ACTTGAATAG ATATTTCTCC AAGGAAGAGG
38851 TACAAATGGT TAACAAGCAT ATCAAGAGAT GCTCAACATC ACTAATCATT
38901 ACAGAAATGC AAATCAAAAC TACAGTAAGG CATTACATTA CACCCCTCAG
38951 GATGGTCACT ATCACAAAAA CAGAAAATGA GAAGTGTTGG TAAAGATGTG
39001 GAGAAATCGG AATTCTTGTG CACTCTTAGG AATGTAAAAT GGTGTAACCA
39051 GTATGGAAAA CAGATAGAAG TACCTCAAAA AATTAAAAAT AAAATTAACC
39101 ATATGATCCA GCAATCCCAT TTCTGAGTAT ATATCCAAAA GAATCGAATC
39151 CAGAATCTTG AAGATATATT TGCACACCCA TGTTCACTGC AGCATTATTC
39201 ACAATAGCCA AAAAAAAATC CATTGATGGA TAAATGAATA AAGAAAATGT
39251 GGTAGATATA CATGCAATGG AATATTATTT AGCCTTAAGA AGGAAATTTT
39301 GTGACATGCT ACAATATGGA TGAACCTAGT GGACTTATGC TAAGTGAAAT
39351 AAGCCAAATG ACAAATATTG TATGATTCCA CTTACATGAG GTATTAAAAG
39401 TAGTCAAACT CATAGAAACA GGGGCTGTGT GAGGGGAAAA TGGGAACTTG
39451 TTACTTCAGT GGGTAATAGA GTTTCAGTTT TGTAAGGTGA AAAGNNNNNN
39501 NNNNNNNNNN NNNNNNNNNN NNNNNNNNNN NNNNNNNNNN NNNNNNNNNN
39551 NNNNNNNNNN NNNNNNNNNN NNNNNNNNNN NNNNNNNNNN NNNNNNNNNN
39601 NNNNNNNNNN NNNNNNNNNN NNNNNNNNNN NNNNNNNNNN NNNNNNNNNN
39651 NNNNNNNNNN NNNNNNNNNN NNNNNNNNNN NNNNNNNNNN NNNNNNNNNN
39701 NNNNNNNNNN NNNNNNNNNN NNNNNNNNNN NNNNNNNNNN NNNNNNNNNN
39751 NNNNNNNNNN NNNNNNNNNN NNNNNNNNNN NNNNNNNNNN NNNNNNNNNN
39801 NNNNNNNNNN NNNNNNNNNN NNNNNNNNNN NNNNNNNNNN NNNNNNNNNN
39851 NNNNNNNNNN NNNNNNNNNN NNNNNNNNNN NNNNNNNNNN NNNNNNNNNN
39901 NNNNNNNNNN NNNNNNNNNN NNNNNNNNNN NNNNNNNNNN NNNNNNNNNN
39951 NNNNNNNNNN NNNNNNNNNN NNNNNNNNNN NNNNNNNNNN NNNNNNNNNN
40001 NNNNNNNNNN NNNNNNNNNN NNNNNNNNNN NNNNNNNNNN NNNNNNNNNN
40051 NNNNNNNNNN NNNNNNNNNN NNNNNNNNNN NNNNNNNNNN NNNNNNNNNN
40101 NNNNNNNNNN NNNNNNNNNN NNNNNNNNNN NNNNNNNNNN NNNNNNNNNN
40151 NNNNNNNNNN NNNNNNNNNN NNNNNNNNNN NNNNNNNNNN NNNNNNNNNN
40201 NNNNNNNNNN NNNNNNNNNN NNNNNNNNNN NNNNNNNNNN NNNNNNNNNN
40251 NNNNNNNNNN NNNNNNNNNN NNNNNNNNNN NNNNNNNNNN NNNNNNNNNN
40301 NNNNNNNNNN NNNNNNNNNN NNNNNNNNNN NNNNNNNNNN NNNNNNNTAG
40351 TTATTTAAGA AAATAGCCTA AATGTTTCCC AGAGTAGCTA TACTATTTTA
40401 CATTCCCCAC TATTAAGTGT ATGAGTGAAT CAGTTTCTCT GCATCTTCAT
40451 CAGCCATTGG TGTTGTCAGT ATTTTTAAAA TTTTAGCCAT TTTGATAGGT
```

FIGURE 30

```
40501 GTATGGTGAT ATAGCACTGT GGTTTTAATT TGTATTTCCC TAATGGCTAA
40551 CAATATTGAT CATCCTTTCT ATGTGCTGAT GTGATGATGT GCCATTGTAT
40601 ATGTTCTTTG GTGAACTGAC TTTTCCCTAT ATTTTAATTA GATTGTTTGC
40651 TTTTGTTACT GTTGAGTTTT GAAAGTTCTT TATATATCAT AGATACTAGC
40701 CCTCTGACAG ATAGGTGACT TGCAAATACT TATTTAGATC TTTTTTGATC
40751 TTTCATTGGT GTTACGCAGT TTTCCACTTA CAAATACGGT GCATATTTTG
40801 TTATATTTAC ACTTACTTCA TTTTTTGAGT GATTGCAAAT GGTATTGTAT
40851 TTTTGATGTT GGTATCTACA TGTTCACTGC TAGTATATAC AAATACAGTT
40901 GATTTTTATG TTAATATTGT ATCCTGCAAC TTTACTGAGC TCACTTATTA
40951 GTTGTAGGAG AGTTTTGTAG ATTCCCTGGA ATTTTCAACA TAGACAATTA
41001 TGTCATCTGC AAATAGAGAC AGTTTTACCT TTCCTATTCT TATCTTTATG
41051 TTTTTTCTTT TCTTTTCTTG CCTTACTGTA CTGTAGAGAA CTTCCAGCAC
41101 TGTGTTTAAT GGCAGTGGTA AGATGTATGT TCCATCGGTG CTTGACAACT
41151 ATGCACTATT CATTCTTACA TTAAGCATAA TGCTTTTGTA GATTTTCTTC
41201 ATCAAGTTGA AGAGTTCTGG CTGGGTGCGG TGGCTCACGC CTGTAATCTC
41251 AGCAATTTGG GAAGCCAAGG CGGGTGGATC ACCTGAGGTC AGGAGTTTGA
41301 GACCAGCCTG ACCAACATGG CAAAACCCTG TCTCTACTAA AAAATACAAA
41351 AATTAGCTGG GCGTGGTGGC ACGCACCTGT AGTTCCCAGC TACTTGGGAG
41401 GCTGAGGCGG GAGAATCGCT CGAACCCGGG AGGTNNNNNN NNNNNNNNNN
41451 NNNNNNNNNN NNNNNNNNNN NNNNNNNNNN NNNCACTGC AACCTCCACC
41501 TCCTGGGTTC AAGCGATTCT CATGCCTCAG CCTCCCAAGT AGCTGGATTA
41551 CAGGCATGTA CCACCCTGCC TGGCTAATTT TCATATTTTT AGTTAGAGAC
41601 GGGGTTTCAC CATGTTGGGC AAGCTGATCT TGAACTCCTG ACCTCAGGTG
41651 ATCCATTCGC CTCGGCCTTC CAAAGTGCTG GGATTATAGG CACAAGCCAC
41701 TGGGCCAGGC CTCAAATGTT CTTTCTGCAT CATTTGATAT GACCATATGA
41751 TTTTTCTTCT TTAGTCTGTT AAGTATGATG GATTACACTG ACTAATTTTC
41801 AAATATTGAA CCAGCTTTCT ATCCCTGAAA TAAATCTCAC TTGGTCATGG
41851 CATATAATTC TTTTCATATA TATTACTGAG TTCTATGTGC TGATATTTTC
41901 TTGAGTAATT TTGTGTCTAT ATTCATGAAA GATATTGGCC TGTAGTTTTC
41951 TTTTTTGTTG TTGTCTTTGG TTTTAGTATC AAGGTAATAC AAGCTCTTCA
42001 TAAAATGAAT TGGGAAGTGC TTCTCCTATT CTGTTTTCTG GAAAAGATTG
42051 TGTATAATTG GTATTAATTA TTCTGTAAAC ATTTGATAGA ATTCCTGAGT
42101 GAAACTATCT GGTTCTAAAC ATTCCTGTTG GGAGTTTTCA AATTATTAAT
42151 TCAATTTCTT TCATAGTTAT AGGGTTATTC AAATTATGTA TTTCATTGAG
42201 TGAAATGTGG TTATATGTCC TTTTGAGGAA TCAGTCCATT TGTCCATTTT
42251 ATCTAAGTTG TGAAATGTAT GTGTGTAGAG TCATTCTTAG CAATCCCTTA
42301 TGGTCCTTTT GATGTGTACA GAGTCTTTAG TGATATCACC TATATTATTC
42351 CTGGTATTGA TAATACGGGT CTTATGTCTT CTTTGTCTTT GTCAGCCTTG
42401 CTAGATGTTT GTCACTTTTA TTAATCTCAT CAAAGAACCA GCTGTTTCAT
42451 TAATCTTATC AATTTTTTTT TTAAATTTCA TTGATTTATT TCCTTTCTTC
42501 TTACTTTAAG TTTGTTTTGC TTTTCTTTTT TGATTCTTGG TATGGGATCT
42551 TAGATTATTG GTTTGATACT TTTCCTCTTT TCTATTGTAA GTAGTACTCA
42601 GTGCCTTAAA TTTCTCTCAG CGCTAATTTA GCTGCTTTCC GCAAATTTTA
42651 CATGTTGTCC TTCATTTTCA TTCACTTTAC TTTGTCTTTT GATTTCTCCT
42701 GAGACTTATT TGACCCATAG ATTATTTAGA AGTGTATTGT TGATTTCCA
42751 AGTATTTTGA AATTTACCTA TTATCTTTTT GTTACTAGTT TCTAGATTGA
42801 ATTCCATCGT GGTCAGAGGA CACATCTGTA TTCGATATCT ACTCTTATAA
42851 ATATGTTGCC ATTTGCTTTA TGGCAAAGCA TATTTTCTAT CTTAATATAT
42901 ATTCCAGCAG TGCTTGAGAA TAATGTATGG TCTCATGTTG TTTGGTAGGA
42951 TATTCTACAA GTGTTAAATT GTTCCTGTTG GTTGATGGTG TTCTGCTATA
43001 TCCTTGTTGA TTTTCTGTCT ATTTGCTCTA TCAGTTTTTG AGAGAGGGTT
43051 GTTGAAGTCT CCAACTATAA TTGTGGATTT GTCTGTTTCT TTTTCAGTTC
43101 CATCAATTTT TGCTTCAACT ATTTTGCAGC TTTTACTTGG TTCATACACA
43151 TTTAGAATCA TGGTGTATTC TTCCTTGATT GATCATTATG TAATGTATCT
```

FIGURE 3P

```
43201 TTGCTAATTT TCTTTGCTTT TAAGTCTGCT TTATCAGATA CTAATGTATC
43251 CACTTCTGTT TTTCTTTGAT GTTTGCATGA TATATCTTTT CCCATCATTT
43301 TACTTTGAAC TTGCCTATAA CTGTTTTGTT TAAGTGAGTT TCTTATGGAC
43351 AGCACATTTT TGGGTCATGT TTTTTAATCC ACTCTGCCAA TCTTTGTTTT
43401 CTAATTGATG TATTTAGATA TCTGCATTTA ATGTGATTAT TGTTATGTTA
43451 GGGCTTAAGT ATGCCATCTT ATAGTATTGT TTTCTCTTTG TTCTATTTTT
43501 CTTTTCTCTG TTTTCATTTT ACTGGCATCT TTTGGGTTAT TTAAACGTTT
43551 TTTAGAATTC TATTTTCTTT TACTATAGTA CTTTCAAGTA TATCTGTTTG
43601 GATAGCTTTT TTAGTGATTG CTCCAGGTGT TATTATACAC AAATTACCAC
43651 AGTCTACTCG TTCTCATTAT TTTACTAATT TGAGTGGAAT ATAGAAACTT
43701 TATCTCTCAT TATATTCCCT TACCCTCCTC TATTTATAAT AAAATTATCT
43751 GAACTATTTT ATGTACAATT AGAAATACAT GAGGCAGTGT TATAACTTTC
43801 GCTTCAACTG TCAAACATAA TTTAGAAAAC TCAGGATGAA AGTCCATTGT
43851 TTTAAACCAT ATTTTGGCAT ATCCTGTTCT TTCTTCCTGA TAATTCAAGG
43901 TTTGTTCTTT TATGTTTAAT TTCTGTTTAA AGAACATCCT TTAGCTGTTT
43951 TTTAAGGGTA GGTCTGCTAG TGACAAATTC TCTTAGTTTC TCTTCATCTG
44001 AGAATATCTT GATTTCCCCT TCATTCCTGA AATATATATA TACATATATA
44051 TATATGTATA TACATATGTA TATATCCATA TGTGTGTGTG TGTGTGTGTA
44101 TATATATATA TATATAGCTA GGTATAGAAT TCTCGGTTGA CAGTACTTTT
44151 ATTTTAGCAC TAGAAAAATG CTGTGTAACT GCCTTCTGTT CTTTTGGTTT
44201 CTAATGAGAA ATCTACTTTA ATTCTAATTG TTCTTCCTCT GTAAGTGAGG
44251 TATTGTTTTT CTTTGCTTTC AAGATTTATT TCTGCCTGTA GTTTTCAGAA
44301 GTTTGATTAT GATGTGTCTT GGCATGCACT CCTCTGAGAT TATTCTGTTT
44351 GAGGTTCATT CAGCTTCTTG AATCTGTAGG TTTATTTCTC CTTCCAAATT
44401 TGGCCGGTTT TCAGCCATTA TTACCTTGAG TACTTTTTCA GCCCCACTTT
44451 CTTTCTCTTC TCCTTCCAGG ATTCTGTTGA CATGAATGTT AGATCTTTTC
44501 TTATAGTCTC TTAGGTTCCT TAGGCTCCGT TCATTTTTTT CATTCTATTT
44551 TCTCTGTTAT TCAGATTGGG TAATTTACAT TGTTCTATTT TCCAGTTCAT
44601 TGATTATTTC CTCTGTCCCC TGCATTCTGT TGTTGAGCCT ATCTACTGAG
44651 CTTTTTATTT TGGTTATTGT ATTTTTTTAA TTCTAAAATT TCCACTTAGT
44701 TATTCTTTAT ATCTTCTATT CTTATTCTCT GTTTCTTTGC ATGTGTTTTC
44751 ATTTGTTTCA AGCCTGCTCA TATTATTTTT TGAAACATGT TTTATGATGG
44801 CCGCTTTAAA TTGGATATTT TTAACATCTC TATTATCTTG GTGTTGGCAT
44851 CCCTTAATTG TCTTTTTAAA TTAATTTTGA GGCCAGGCAC GGTGGCTCAC
44901 ACCTTAATCA CAGCACTTTG GGAGGCCAAG GCAGGTGGAT CACTTGAGGT
44951 TAAGAGTTCC AGACCAGACT AGCCTGGCCA ACATGGTGAA ACCCCGTCTC
45001 TACTAAAAAT ACAAAAATTA GCCAGGCATG GTGGTGCACG CCTGTAATTC
45051 CCACTACTCG GGAGGCTGAG GCACGACACT TACTTGAACT TGGGAGACAA
45101 AGGTTGTAGT GAGCCCAGAT CACGCCACTG CACTCCAGCC TGGGTGTTGG
45151 AGTGATACAC TGTCTCAAAA AAAAAAAAA AATTAATTTT GAGATCTTTC
45201 CTGGTTCTTG GTATGATGAG TGATTTTTTT CCTGTACATT TTCAATATTT
45251 TGTTATGAGT CTCTGGATCT TACTTAAACC TTCTGTTTTA ACTTACTTCC
45301 TCTCACACCC CTCTTGGAGA AACTGGGAGG TGCTGCCTCA TTCATGCCAG
45351 GTAGAAGTCC AGGCTCGCCA CTTGGCCTTC ATTGACACCA AAAGGGAGGG
45401 ATCTCCCTTG TTATTGTTGT GTGTGAGTAG GAGTTCTGGA TCCTCCCTAG
45451 AATGATACCT TCCTGGCTGG AAGAGATAGG AATGCTTCAT TATCTTCCAC
45501 ACTTGACCTC CACTGACACC ATATGGGTAG AGGTGACCTC ATTACTACTG
45551 AGCAGTTGTG AAAGTCCTAT ACAACTATTA TGGGCTAAGC TCTAGGGTCC
45601 CATCTTTGGT CTAAATCCAG CCTGCCTTCC AAATTATTCC CTGAAAATTC
45651 CTTTAACTAG AGTAGCTGGT CTTCCAGTAG CTATCAGGAT GTAGAGCACT
45701 TTACAATAGC AAGACTCATC CTCTCATCTT TGCCTTTGCT CGTCTTTCAG
45751 GTAATGGAGG TCAGATGAAG GCATGACATA ATGGTAAGA GGAATGATTA
45801 TAGTGTGATC AAGCATTCAG TTCTCCCTTT GCCTAAAACC TTCTGTGCTT
45851 AAGTTGCCAT GTGGTGCCCT TCCCCAAACT CCTCAGCACT ATGCCAAGTC
```

FIGURE 3Q

```
45901 AAATCCTGAC ACTGTCTTCC TGGTCACCTT TTAGTTTGCA TCACTCTATT
45951 CCTCAAATGT CAAGTGTTTC TTCTGTTTGA AGTGTCTTCT GTCACCAGTA
46001 AGACATGTGT GGCATCTGTG CCTGGTCCTC CTTAGCCTAT AACACTAAGA
46051 CTCCAACCCT GCCTAGAGCA TGATGACCTA AATTATTTTG GTTGCCCAAC
46101 AGCCTTCTGG ATGTTTCAAG AGTGTCTTCA AGCCAAGCTG AACTCTTACC
46151 TTACCATGCT CTTCCTCCTC TCTTCACAGT TTAGTTAGTG GCATCACCAT
46201 GTCTATGCAA ACATCCCACA CCAGAAACTC TGGAGGCATC TTTGACTCTT
46251 CCCCTGTTCC CTAATCCCAT ACATTCAGCT AGGGTCCATG CCAATCTTGA
46301 CTCAGTTCCC ATTCTGCCCC CTGGCTTCAA ATATCCATCT CCAGGCCTTT
46351 CTGTAACCTG TGTTTTCTGA GGAGTATAGG GTTTTTAACA CCCTTTGAGG
46401 CTGGAGGTCC TTGAGCTCCT AAAGTCCAAA CTTGGGATTC CTTGTGAGTT
46451 TCTGAAATAA ACAGAAACTC AACATTTCCA TAATTACTTA ATTCTCTGGG
46501 GAGTTTGACA TTTATAGTGG TTAAGAGTTT GGGCTGGAGG GCATAGCTGC
46551 CCAGGTATGA ATCTGGCTCT GCTACTTGCT AGTTTCATGA CGTTGGGCAA
46601 GATACCTAAT CTGTCTATGC CTCAGTTTCC TCATTAGTGA AATGGGGATA
46651 ATGATAGTAC TTACCTCAAA GGGATTTAGT TGGAATTAAA TGAGTTAATA
46701 CAGTTAAATT GTTAGAACT TGCCTGGCAA ATAGTAAGTG CTCAATAAAT
46751 GCTGTTGTTA TTATTACTGT CATTATTAAT ACCTACATTA TCTTAGTAGC
46801 TCTCGAAGGC ACTGCTATAT TATACTAAGA AGGCTATTGT ATAATTTTGC
46851 AGTTTTAGTG GACAGGGACA GTTAGTAAAA GGGCAAGTTA AGTTACACAG
46901 ACTACATAAG TCCAGAAGCA TCACTATATT ACTGCATAGT ACAGTAATTG
46951 TTCATAACAG TGTCCCTTGT TTTCTTTTTA TTAATACCAG ATTTCAATCA
47001 AATTAAGGTC ATGAAAGTTT AATTACTTAT GCACTAAAAC TTACCAGAAA
47051 ATATAAAATA TCTCATTTTC TGGAATAGAT AAACGAAGCT TAATTGTATC
47101 AATGAGCTAC CAGAATCATT TCATTAAGGA GGTCACCAGA TTGTTGTAGT
47151 TAGCAAAGGA CTCTCTCCCA ATTAGGAAAT TAGTTTTTCT ATTGAGACCT
47201 AATAACTGCA GAAATTAGAG CATTTGTAAC AACTTTTTTT TTCGTTTTCT
47251 TAAATATATC ACATTCAATC CACCTGTTCT TTTAAATTAA GAACTGAGGA
47301 CTTGTGTAAA AAATAAACTT TAGTTCCATA TTAAAACCAG TTATGATCAG
47351 GAGGAAGAAA GGGAGAGGTA TGAGAATAGA GAATAGAAGC AGGATACTTT
47401 GATGTGTATC AGTCACTATG TATCTGGTGC TTAACAGCTT ACACTGGTTT
47451 GTTTGTTTTT CATTTTGTAC GGGGCTTTTA CACATACATT ATGTAGTTCC
47501 TTAGAATAGT CTTGTGGTAA GGCAATTATC ATCTAACCCA TTTTATAGAT
47551 GAAATGGAGG CTTACAAAAG GCAATTTCTC CAAACTCACT GAGCTAAGGA
47601 TGTGGCTGAG CTTAACTCA AACCCAGGTC TTCCCTCTCT TTGAAGAAAG
47651 AAATGGGGAG AAAGGAACTG GAAGAGAAAA TACCGGTCAT TTTTGAGGTG
47701 CTGGCAGTAT CATTTTACTT TCATTCTACA CTCTCATCAC ATCTTCTTTC
47751 AAATGTTGAT CAGCTAATTG TTTATGTGAC ACCTTTACTG TACCATCCTA
47801 GAGAGTCCAT GTGAATGGGT ATTTAATGCC ATGGGAAATA ATTTGCTGAG
47851 CTACAGAGGT AGTGACTAAG GCAGTGTCAC CCCAGGAGCT CTCTACTCTT
47901 AATCTAGACT GCAGAAGATT TTCTTTCTTC TCCTGACTCC CATTTTAAAA
47951 CTCTGGCAGA AAATAATTAG CCTAAATGAG CTCCTTGGTG GAATCATTGC
48001 ACTTGGCATT GTTAGAAATG CAAAGAGTAT TATTCACTTG ATTATCTAAT
48051 CTATTTATAT CTAAAAGTTT CTCCAGTATT TACGTTTGTC CGTTAGTTTC
48101 CAAAATCTGC CTAATTCCCA ACAGACTCCA CATAAAGACA TGGTATAACA
48151 GGATATATCC ATGGTCTCTC ATTCCTTTCT GTCAAGATAT GAATGGTCTT
48201 TAAAGGCCCC ACTTGCTGCA ATGAACCAGA AATATCTTCA AATCTTTAAC
48251 AAAAGACCTA CATTTTATGA CTTTGTAAAT TCATTTAAAT TTGTTTCAGC
48301 AGGAGTGAAT AATTTATTAT AGCTGTAAAA GGAAGGAAAT ATGTAGTCGC
48351 TTTTCTTAAC TAAAGTAATT CAGATTTTCA AAGAATAGCC CTATTTGTAA
48401 AGAAATTATG CATGTGGGAT AGGGATGGTT TTGTCTCTGT AAGTAAAGCA
48451 TTTTTTTTAA AAAAATCAAA ACTACTAAAA CCTTAAGACA CAAAATAAAG
48501 GATGAATTTA TAGTGTCTTT GGTACCTATA GTATGTGTGG CAGATTCATG
48551 TTGATGTCTG GGGATTCCAA TTTTTATATT TTTATTGTAT TAGAAAAATG
```

FIGURE 3R

```
48601 TTTTTTTCTT ACACTTGGAA GGAAATAATG AGATGTGAAG GAAATTTTCA
48651 TGCGTATATA AAATGTATTT AGATTATTAA AATAATTAAA TTTAAGTGTG
48701 AAAAGATAGG GGAATGTCTA CTTAGGTAAA TATTTTTAGT TCAAATATTT
48751 TTAGTACATG GTATTCAAGA AACATGTTTA GTTGTTCTAC AGAATTTTAA
48801 ACTTCAACCC TAACATCTGT ACTTACTTCT ACTAGTGCTT TTACTATCAC
48851 CCAATGACTT TTAGNNNNNN NNNNNNNNNN NNNNNNNNNN NNNNNNNNNN
48901 NNNNNNNNNN NNNNNNNNNN NNNNNNNNNN NNNNNNNNNN NNNNNNNNNN
48951 NNNNNNNNNN NNNNNNNNNN NNNNNNNNNN NNNNNNNNNN NNNNNNNNNN
49001 NNNNNNNNNN NNNNNNNNNN NNNNNNNNNN NNNNNNNNNN NNNNNNNNNN
49051 NNNNNNNNNN NNNNNNNNNN NNNNNNNNNN NNNNNNNNNN NNNNNNNNNN
49101 NNNNNNNNNN NNNNNNNNNN NNNNNNNNNN NNNNNNNNNN NNNNNNNNNN
49151 NNNNNNNNNN NNNNNNNNNN NNNNNNNNNN NNNNNNNNNN NNNNNNNNNN
49201 NNNNNNNNNN NNNNNNNNNN NNNNNNNNNN NNNNNNNNNN NNNNNNNNNN
49251 NNNNNNNNNN NNNNNNNNNN NNNNNNNNNN NNNNNNNNNN NNNNNNNNNN
49301 NNNNNNNNNN NNNNNNNNNN NNNNNNNNNN NNNNNNNNNN NNNNNNNNNN
49351 NNNNNNNNNN NNNNNNNNNN NNNNNNNNNN NNNNNNNNNN NNNNNNNNNN
49401 NNNNNNNNNN NNNNNNNNNN NNNNNNNNNN NNNNNNNNNN NNNNNNNNNN
49451 NNNNNNNNNN NNNNNNNNNN NNNNNNNNNN NNNNNAGGTT GGGAAAATAT
49501 TTCAAGTGGG ATCCAAAATC ATTGTTTTAA TATTGTATTT CATGTAGCAT
49551 TGCAGATGAA AGAGGAATAT GTAACTTAAG AATTTATTTC ATTTTTTAGA
49601 AAAAATACTA TATATAATTG TGGTAAATAG TACAACCACT AAAAAAGATA
49651 ATCAAATAAA CGCCAATGAA ATTTTCATCT ACATTAAAAG CTGAAGTTTC
49701 TAGATGTGGG TTGCTTGATT ATATCTTAGA GCTCAGGACT AGAATGATGT
49751 AATATTTTAT TTTTCTATTA CAGATGACTT GTTTAAAGTT CACAAGCTTA
49801 AGCCAAATCT GAAGTGGCGA CAGGCTTTTG ACAGCTACTT AAAAACTCTG
49851 CCTCCATACT ACCTATTAGT ATGTATTTGT GTGTATATAT GTATTAACTG
49901 TATCAATGAT AATTCTTGTC ACAAGAAATG TTAGTGATCA AAAGCTTTTA
49951 CTGTTGCAAT AAGAGAGATA TCTTTTTATT TTACAGATAT TTGTGTCGTC
50001 ACTGTCTTCT CAAATCATGT GTAAGAGTTT GGAGATGTCA TGGCGGCACA
50051 AAAGAGAGCT GTTTTCTCTA TTTTATTCCT TTAACTGCCA TGGTTATTTT
50101 TATAAAACAC ATCTATGTTT CTCTTATTAA AAGTAACCTT AATTTCATTG
50151 GGAATTTAAG AATAAATAGA TCTGGATTCA TATATTACAT CAACTTCCCT
50201 TTTTAACTCT AGAAATTCTC AGTATGGGGT TTCCCTCTGG AAAAAGAAAA
50251 TCTGAAGACA TTACAGTTGC CTATTGCCTC TTAAATGTGT CCTAGACACA
50301 GCATGAAGTT GGGGCACTGG TGGTGAGAGG CGGAATCCAA AAAAATTCAG
50351 AAATGACTTG GCCTCATTTT GGATTTCATA ATGTGAAGTA TTCATGATTT
50401 TGAACTGGTA ATATAATCTA AATCAAGATT ACCAAAATAA TTTCAGAGGT
50451 TGATGTGGTA ACCTTTAAGC GAAGTTTCTA GAGGTGAAAA GGCAGAATCT
50501 TAAATGGTAC CATTGGTGTC ACTGGGAGGA GAAATTGGGG TGTGTTACTG
50551 TTTACCATGG CAGTAATGGG GCAAACAATA AAATGCAATG TGAAATGATT
50601 TGATGATTTG GGAAATAAGA TTGAACGCAA TTTACTTGTT TGAATTTGCT
50651 GTTACTTGCT CTTCTTATCC CACTCTCTTC TGATTTTTTT TTACTTTCTG
50701 CTCCTTACTT CTCTGCTATT TTCATTGCCA CTTTTTAATG TTCCATGTTT
50751 GGTTTTATGT GCAGCACCTT GACTTCTAAG AAATGAATCA TGTCCCTTTG
50801 CCCCTTATAA CTGAACTTTG AGTATTTTAA GATTTATTCT ATTCTTACTG
50851 TTGTGTATTT TGTTTCCTTA TAGCCATTAA AGAAAGCACT AAGGATGATG
50901 GGAGCTCCAA ATCTGATATC AGATAATTTA GATTGTGGAC TTAGTTACAG
50951 TGTTATCTCT TACCTTAAAA AACTCAGCCA ACAGGTAGTA TTGGTAAAAA
51001 CAAACAAACA AAAATCCTTT GCCCTCAGAA GTGCATTTCC TTATTCTTTA
51051 GTGTAATTGT AATTTTTCAA ATTAAATGTG TATATATCTC TACACTTTAT
51101 GGATTAGTAA TAATGTGATT CTCTATGGCT TCTAGCTTCA CCATTAAGCT
51151 GCAGTTAAGG GTCTGTCAGT ATCATTTGAT GCTGTGCCAT TTCTCCTTTT
51201 GCCTGCCAGT TTGTCCTACC CGCAAGCTGG TTGATATGGG GCAGAGGTTT
51251 AATAGACTTC TCTCATGGGT CACATTTTGT CTATCTTCAA CCTAGTTCCT
```

FIGURE 3S

```
51301 CCTCAGATCA CTCTGGGCTA CAGCATCCCT CCTGTTTAGA TCAGCACACT
51351 GAGGCGTGGT GTGATTAAAT GACTTGTCTG AGATTAGTTT TCAGGCATGT
51401 GAAGGACTTA TACTCACATG CTAGCCCTTG GATAAAGAGC TATATGCTTT
51451 TCCCTGGAGA GTGGGGAGAT GAGACCAGTG TTCCTCACAC TGGAGGGTGA
51501 TAGACCCCAA GGGGAACTGA AGAGTGGAGC TCAGTTTCCT CTCTTCTCAC
51551 CCTCCACCTG TTCCTCATTT GCCATTATTC ACCTTGTCCC TTGCCTGCCC
51601 CTCTCTATTA GTACCTCATC CTCCACTCAC CGTTCCTTAT CATACTTCTC
51651 ACCTCTACTT AGCCCATTCT TGTAGGATGG AAATATTTGA GAACTACTGA
51701 GTTAGAACTT TACTATCATA TGAATGTGTT ATGTTATATG ACAAATTAAT
51751 GCAGCAGTTT TACTTACCTT ATGCACAAAG GTATTCCCAG GTAGGGGACA
51801 ATAGTAGCAT TCGCAGTGGT GATAATGCTT CAAGGTGGAT GTGTTTGGAA
51851 GTTTGGCCTT TAGGAAATGG AGAGTAGTGA GCAAAACATC AGATTTCACC
51901 AAAGAACCAA AGTGACTCCA CAATTGGGAT GCCGACACAC CTTGCTAGGA
51951 ACTGACAACA ACTTCAGTAT GGTCTGGAGC TTACCAGCTC CTACCAGTCC
52001 AGTGTGCTTA TAAGTGCAAA AGAAAGTAAA GGCAACCCCA GATTTCTAAT
52051 CTACCAAGTG TCCCCCTAAC CTCCTTTCCT CTCTGCTAAT AGATTTTTTG
52101 TGGTTGTTGT AAATGTTTTG GTTTGGTTAT TTATTTATTT ATCTATCTAT
52151 TGATCTATCG ATTTTTTTA ATTTGATGTT TACCTAAGCC TTTAAGGCTG
52201 TGTCACCAAG GTATGGCCAC AAGGAAGAAT AGTGTACAGA GATTTTAATT
52251 AATGCAAGTT CTGGGACCTT TTGGGGCACA TGTATCATTT TACAAATGAG
52301 CTTTCAAGAC CATTTAAGGA AACAGATGCT TCATTTGCTC TTATCTCATA
52351 TTTCATGACT TAAGAATTTT TTAGTGATAA TAAACATAGA CTTAATTCCA
52401 ATAATTAGGG AAAATTGATA AATATCTGTC ACCAAACCAC AAGAAATCCA
52451 AAATCATTTT AGGTTTACCA AACATTGGTG GAATTCCATC TTTCTGAGAA
52501 AAAGGGAAGA TCATAGCTAA TTTATAATAG CTCAAATTAC TAATTTAATA
52551 ACTGGGTCAC CAGTGTTTCT TGAGCCATTT CAGATGTATG TAAAACACAA
52601 AATATGCCAA ATATATATTG CTATAATACA CTCAAGCAGT ATTAATCAAT
52651 ATGGTATCAC AATGCCTATT AAGAGGCTTT TTACAAATTA CTTACTTAGT
52701 AATATCTGTT AAATTAAGCA TTATCTTCTA AGACCTTTTT TGGATAGTCA
52751 AATATAAGAG ATAAATAGTT TAATTTTTTC AGACCTTTTT TGGATAGTCC
52801 AATATTAGAG ATAAATAGTT TAATTTTTTC AGATATAATG CCAGTCGATG
52851 TGATCTGAAT TTTAGTACTA GTTTACACGT ATAAATACAG TCTTAAACCT
52901 TTATGTCTGA GTCTGAAATG AACCTGTTCA CTTAGACTAG ATTTTATAGT
52951 AACAAAATGT GCTTTTAAAT GTCTATGAAT GAAATTCTTA TTCATGGTTT
53001 TTATTCTCTC CATGATTTTA TTATAATTTT GACACTAGAC AAGAAAAAAA
53051 AATATTATTT GTCTTTCCTG CCCCCTATCT GTTTGCTGTG ATAGTGCAAA
53101 GAAGCACAGG AAAATGTTTA ATTATCCATT TTTCTGTGAT TTGTAATTGA
53151 AAATTGTTCT GTGGGGTTCT GAAAGTATTA TCTTTCTTAA GTAGTAAAAA
53201 TGACAGTGGT AATGTAGATG TTTTTATAAC ATACTATGTA CTTTCATTTT
53251 AGACCAAACT AGAGTCAGAA CNNNNNNNNN NNNNNNNNNN NNNNNNNNNN
53301 NNNNNNNNNN NNNNNNNNNN NNNNNNNNNN NNNNNNNNNN NNNNNNNNNN
53351 NNNNNNNNNN NNNNNNNNNN NNNNNNNNNN NNNNNNNNNN NNNNNNNNNN
53401 NNNNNNNNNN NNNNNNNNNN NNNNNNNNNN NNNNNNNNNN NNNNNNNNNN
53451 NNNNNNNNNN NNNNNNNNNN NNNNNNNNNN NNNNNNNNNN NNNNNNNNNN
53501 NNNNNNNNNN NNNNNNNNNN NNNNNNNNNN NNNNNNNNNN NNNNNNNNNN
53551 NNNNNNNNNN NNNNNNNNNN NNNNNNNNNN NNNNNNNNNN NNNNNNNNNN
53601 NNNNNNNNNN NNNNNNNNNN NNNNNNNNNN NNNNNNNNNN NNNNNNNNNN
53651 NNNNNNNNNN NNNNNNNNNN NNNNNNNNNN NNNNNNNNNN NNNNNNNNNN
53701 NNNNNNNNNN NNNNNNNNNN NNNNNNNNNN NNNNNNNNNN NNNNNNNNNN
53751 NNNNNNNNNN NNNNNNNNNN NNNNNNNNNN NNNNNNNNNN NNNNNNNNNN
53801 NNNNNNNNNN NNNNNNNNNN NNNNNNNNNN NNNNNNNNNN NNNNNNNNNN
53851 NNNNNNNNNN NNNNNNNNNN NNNNNNNNNN NNNNNNNNNN NNNNNNAGAA
53901 AGTCTTGGCC AGCACAGTGG GGACCTCTAG CACCAAGATT TCCTACAGAG
53951 GAGGGCCACA CTGGGCAGAG CTGGCCAGGC CCTAACACCC TGCCATTGTC
```

FIGURE 3T

```
54001 TGTTACTGGC TATGGGCAGC CTGGGAAGGG CATGGCCTCA GCTCAGTGCT
54051 GCAGCGGATC CCTATGGCAC CACAGCAGCG GGAGGCTCTC TGCTAACTGC
54101 ACTCCTTGCA GGATCAGCCA TTGCTTTCCT GAAGGGAGAT CCCAGCAGCT
54151 CACCTCCCCT CCATGGCTGC CAGAGGAATA CATCTAGAGT ACGAGCAGTG
54201 GTCCTGCAAG GCGGCCACAG GTATCAATCT CGGGATTTGG TGTTTTAAAT
54251 GACATATTTG AAAAGGGATA GTCCCAGTGG CTTTAATACC CTGTAGGTGT
54301 GTTACAATGC AGAACAAGGC TAGCAAGTGG AATTTTGCCA CTGGGAAAAT
54351 TCTACTGTAG TCAGTTGTAT TGATATAACA CTCTTCAATA ACATTTTAAG
54401 AGAGATAAGT ATGACATTTC TATATTAAAA GCCTTAGGAG TAACTGAAAT
54451 TATTTGTTTC ATTTCAAATA GGATTTGAAA CCTCAGACAT ACAGAAATGC
54501 TTATGATATT CCCCGTAGAG GTCTTTTAGA CCAGCTGACC AGAATGAGAT
54551 CCAATCTGCT GAAAACGCAC AAGTTTATTG TTGGACAAGA TGAAGGTAAA
54601 ATAACTGTGA AATACTTTTT TTTTTTTTTT GGAAAATGCC AGGCATGACT
54651 TACAGGAAGG TGTTTATTGC ATAATGAGTA GGCTATTTTA TAGTATTTTA
54701 ATGTTTAAAA TGCCTGTTTT CACTGAATCC CTATGTCTGT TTACCAGGCA
54751 CATTTTTTTT TTCAAGTTTA AGGTCAAGTG TGCATTAATC AGCACGTACA
54801 CTACACTTGC CATGCTTTAG CTATTGTAAG CTTCAAACAA CCCCAGGAAA
54851 TAGATACTGT TTTTATGTCC AATTCATGGA CATGGAAACT GAGAGTGAGG
54901 ATTTTTAGTA GTTTGCCCAA GTTTAGCCAG TTGGAAAGTG GCAGAACCTA
54951 GGTCTGTCAG ATTTCCCAAT TTGCACACCC AAACACTAAC ACTCAGCCTA
55001 CTGTGATAAA TTCAGTAGAG AATACCTCAT TTAAATGAAA GTAATCAACC
55051 TAATGGTATC CAGGATAATT GTGACTATTT ACAAATTCCA TTTACTCCAT
55101 TTTGTTAATT TTAAAAGGC TCACCTGTTC ACTAAAATGA GCAAATCTTA
55151 TTCTGGTCAA TTCCCTGAAA TTATACACAA AGTTTTGTGT GTAAGAGGGC
55201 TTTTCTAGGA AGAGAACCTA CAGATTTAAT CAAATTCTCA GGATTAAGAC
55251 CTACTAACCA AGATTCTCTG GATGATAAGT GAATGCCATA GAGACTAGAC
55301 TCTTTGAAAT GCAGAAGATA TGTGGTGATT TGAGTTGGGA TGGTGGTGTA
55351 GGGTCAGCCC ATTCTCAAAC CTGGTTTGAA GGCAAGGGAG TTGTTCTGAT
55401 CCTAGCGATG TGAGCCTGTA GGCAGTAGTA ACGGTAGACT AAGTTATGAT
55451 TGGGATGAAG AGAGATGATT CTAGATCCTA GAATGCTAGA TTCGAGACTT
55501 TAAATACTAT TTGATGCCAA GACACACACT GCTAAACCAA ACTATGATCA
55551 TGTCTTCTCG AAAGGACCAT ACGCTTCAGC TATAAGCATC AATTTCTTTT
55601 CCTGTGATTT TGCAGATTCC CTTCATAGTG TTCCAGTTGC ACAAATGGGT
55651 AACTATCAGG AATATCTGAA GACATTGGCT TCTCCACTGC GAGAGATTGA
55701 TCCAGACCAA CCCAAAAGAC TGCATACTTT TGGCAATCCG TTTAAACAAG
55751 ATAAGAAGGT AGGATACCTA TGCCTATGTC TGCCTAAATT GGGATATTCT
55801 TGCTATATAA TTATTTTCTT TTTGGCAAGA TAAATACAAA TCAGAGGTTC
55851 TTCATTTGTT TGTTTAAACA ATAAAATATG ACACTAAGGC TCTTAGTGGG
55901 AGCCTCCTGA TGCAAGAGTG TGTTGGTTGA ATAAAGTCAG AGCTGCCATG
55951 TATTGAGTAC TAGTAGGAGC TGGTGTTTTA AATGATCTCA CTTAATGCTC
56001 ACAACTGTTC TGTAAGACAA ATGTTACTGT TTGTCCTTTA AAAGGGAGAA
56051 ATCAAAGGCC ACAGTGGTCA AACGCCTTAC CTGTGACATA GCACATAAGA
56101 GCAAGGATTT GAATCCACGT CTTTCTCACT CCAGAATCTA TATTCATTCC
56151 ACCACACACT AATTTCTTTA ATATCAAAAT CACAGTTTAT TTCCTGTTTC
56201 CATGATTCAT ATCTGTAGTG CTTGATCTAG AAAACGATGA ATGTGTCCCT
56251 TGAAATATGA AGTACTAAGT GATGTTGTTT TACTTGAATG GTCCTACTAA
56301 AAATCTAAAT GTGGGGAGTG TGTGTGTGT TGTGTGTGTG TGTATGTGTG
56351 TGTGTGTGTG TTATACTGAC TTGCCCATTA AAGCATGAAA ACAAATGGGA
56401 TTATAGCTGC ACTCATGGAG GAGACCATTG GTGTTAATTA AGGCTCAGAC
56451 CACACAATAA TCTCTTTTGT GACAAGACTG ATTGAAAGGT ATTCCACGTC
56501 ACCTAAATCC TCAATTTATC TTTCTATGCT TCACTTTCCT CATTTTGTAG
56551 CACTGGGAAT AATAATTACA CCTAACTATG CTGGACGAGG TGGCTCACGC
56601 CTGTAATCCC AGCACATTGG GAGGCCGAGG CAGGCAAATC ACTTGAGGTT
56651 GGGAGTTTGA GACCAGCCTG GCCAACATGG CAAAACCCTG TCTCTACTAA
```

FIGURE 3U

```
56701 AAATACAAAA ATTAGCCAGG CGTGGTGGTG GGTGCCTGTA ATCCCAGCTA
56751 CTCTGGAAGT CTTAGGCAGG AGAATCACTT GAACCTGGGA GGCGGAGATT
56801 GCAGTGAACC AAGATCGTAC CACTGCGCTC CAGCCTGGGT GACAGAGTGA
56851 GACTCCATCT CAAAAAAAAA AAAAAAAAAA ATTACACCTA ATTAACTAAT
56901 AGAACTCTGC ATAATATTAA GTGAGTACAT GTACATTGTT TACAACATGA
56951 ACAGGCATGT AGTAAATTAT CTGAAAATGT TTTCCCCTTT CTGTATTGTT
57001 TATGAGTAAA AAATCTTTTG GAAAAGCCAT TTATTATTAT TTTATTCAAC
57051 TAATGAGGGC ACATATTCTT GGATTATTCC TGGACAAGAA CAGCTCTTGG
57101 CTAAATTTCT ATACTGCTGC CTCTCATCTT TTATCTATCC CCCCAAGAGT
57151 GAAAAGCCTC CTCACTGCCT GCCCAGCACC AAAGTGGGCA TATTTGAATC
57201 TCTGTGAGGC TGCAGATGGG GAAGTTACAT TTTCCACCTG CCTGCCTTTC
57251 AACACGTACA TGTAGCATAC TGTACAGTGA TAATCAATGT TGTTTAATGA
57301 TATGAGTTTG GAGCATAAAA AAGGAAATTA TTTCCCTTAT GAAGAGTTGA
57351 TGCAAAATAG TTCGTACTTC TCTCCTTTTG GTTGAATAAT GCTGCTTATT
57401 TGCAAACTTT CTGATTAATC ATTATTGTAG TATGTTTTGC TTGGGACAAC
57451 ATCCTGTATG TTAGTTTCCT CCTTGTTCCA TTTAAATTGG ATTAAAATTG
57501 AGTTGCATAT TTCTAAGAAC AAAGTTGGGG TGGGGTAAGA TAAATCTTCG
57551 GCCCATGATT AAGGTTTATA TTAGTTAATC TGGCATGGGA TTTAAAAAAA
57601 TGAAAGAAAA AAAGACATAT TCGTGATATA ATGCAAGATT GATTATGTAT
57651 GCATATTAAG AGTGCTTGCA GTTATATAAT AGTGGAATTT TGGTCTTTAA
57701 TGAAATACGT TCATTTATGT GTTTTTTAGG GAATGATGAT TGATGAAGCA
57751 GATGAGTTTG TAGCAGGGCC ACAAAACAAA GTGAAACGTC CAGGGGAACC
57801 CAACAGTCCT ATGTCATCTA AGAGAAGGCG GAGTATGTCC CTGCTGTTGA
57851 GGAAACCACA AACACCACCT ACTGTAACTA ACCATGTGGG CGGAAAGGGA
57901 CCACCCTCAG CCTCGTGGTT CCCATCTTAT CCAAACCTCA TAAAACCCAC
57951 CCTTGTACAT ACAGGTATAG AGTAGTGGTT GTGATTTCCT TATGGCTCCT
58001 AGAGGACTAA GACGCTAAAC AATTTTATTT CCCTTTTTGT GTTCCTTCCT
58051 TTGTGTTCAG TTTGTGTTCA TTAAGTAAGC CATTACTAAA TCATCTATTT
58101 GGTAGGTACA ATAAACCCCA CAGGGAGCAG AGACCCTGTT TCAAGGATCT
58151 CAATCTACAT GAGGTGAAAA AAATTATAAT TATATAGTAA TTAACACACA
58201 GTAATTAACA GTAATGAATA CATTGCTTAG CAAGTAAATG CCACAGTAAT
58251 TAATGGAGAA ATGGAAAGAG GTGAGCATGT CTGCTGCAAC CTTTTGGAGT
58301 GGCTGCAAGG GTGAGGAGGA TAAAGCAGGT TTCCCTGGCA GTAGGAGCAA
58351 GTGGACTCAG CAAGACTGGA TCTGCACTTG CTCTTTGTGT TATCACCACC
58401 TATGCATGCT CTAATCCGGT GCAGTCTGGT ATCTGCCTCC TCGACCCCAC
58451 TGAAACATTC TCATCAAGGT CACTAGTGTG TGCAGCACAT TGCCATTCCT
58501 TCTCCACAGC ATTTGACACA GTTGTTCACT CCCTCCTCCA TGTGTACGTT
58551 GGGTGCTCAG ACACCATAAG CTTATAGCTT TCTTTTCCCT CTAATAGCAA
58601 CTCCCTTTCA ACCTCTTTTT CTGGTTTTGC CTTTTCTTTC CACCTCTAAA
58651 TATCATAGGG CCTCAAAACT CAATCCTGGT ACCTCTCCTG TCCTTCACTG
58701 CGTTCTCTTC CTAGGTGACC CCATGCAGTC TTGGGGCTCT AAATTTGACC
58751 TCTAGAATAT AAATTGCTCC TCAATTTCAG ACTCAGACTT ACTTGTGGAC
58801 ATGCATCTCC ACTTAGGTGT CTAATAGACA AATAAAACTC AGTAGGTTTC
58851 ATGAGTTTCA ACTGAACTCT CGAACTTGCC CCTCTCCAAA ACAGCTCTAC
58901 TTGTAGCCTT CCACATTGCA GATAATGACA CCATCCAGAT ATGTGCCAGT
58951 AAAGCTTTAA CATCTGTCAG GGTTGAGGAG GGTAGAGAAG CTCTAGATTG
59001 TAGTGTTTGC AGATTTCCTT CATGTAAATA ATGCTAATAT TTATCAAAGT
59051 CAAGCTGTCA ACCTGAGGTC ATTGAACCAG AGTCGGGAAG AATGCTCTGG
59101 AGGGCAGTTG TGCCCTGGCT CCTGCCACAC TTCAGCACTA TTTACCCAGC
59151 GGCTCAGCTG ACAAACCATA GAGTCATCAT GATTTTTCTC TTATTCTTCC
59201 CTCGCTTTGA TACCTTTCAC AAGTTCAGGA AACTTGATGT TCAACATAAT
59251 CCCTAAATCC CACTATTTCT CTCTATCCCT CCAGTGCACA CTGCTGTGGC
59301 CTCTCACCAC ACTACTACAA TACCTTCTTA TCCAGCTTC ATGTTTCTAA
59351 TCTAGCCCCC ATCTATCACA TACTCTCTAA CCCTGTGGCC AGAAAATTAT
```

FIGURE 3V

```
59401 GTCTGCATGT ATATCACATC ATGCCATGTC GCTCCTGAAA ACCTGTCCTC
59451 AACTCTCCTG AGCACTCAGA AGGGACCCTG AACCAGCTTT AGTCTGCAAG
59501 ACTGCACGGC TGGCCTCTGT CACCTTCTCC TAACACGGGA GCCCCTGGGG
59551 CTCCCTCTGC TGCTGTCTCC CAAAGGCCTG TAGATGACTT CCCCAACACC
59601 AGCCCAATGC TGCTTGTTTC ATTTGCTCAT TGTGCATGTA CTGTCTGACT
59651 GCCCCATGAG GATGTGAGCT CCACAAGGGC AGGGAACGTT GCTCTGGCTG
59701 TTTACTGCTG ATCTCCAGCT CCCGACACAC TGCCTGCCAC AGACGATGAA
59751 TAAATGAAAG AGGTGTCAGA TCTGGAGTGA AAAGAAAGTA CTTTTCTGAC
59801 ACAGAAAAGA AGGATTAGGA AGATAATACA CTAAGAGGGA TTTTTGGTGA
59851 TGGAGTGTGT ATAGAACTTT CAGCACTAAT GGCCGCCTCT ATTTTCTCAG
59901 AATGTATTTG ATGTAAAGAG GAGGCAGGTT GTGGTGTATC CAAGTTGTCT
59951 GGCTTCCAGC TCAGTAAAGC ATGGCAGGTT GTATGTGAAT TTGAGAAATC
60001 ATGAAATAAA GTGAGACTTG CTGTTTTCAA CTTGAAAAGC ATAACAAGCT
60051 GACACTAACG CATGAGTACC AGGGATCTGT GAATGTGTGT TTAGAGTTGT
60101 ACTGTCTTAC TTGGTTTCCA TATGTATTCA TAGGGCCAGA AAATAAGAGG
60151 TGGTTTTATT GTATTATGTG TCCTGGCCTC AATTTGAGGG GTCTCAGATC
60201 GCCACCTGGT ATATCATCCT GCTTTATGAG ATAATTTCCT AGAAATTGAG
60251 CATCAGAGGG ATATACCTGT GGGGTTGACA TAATACCCTT ACCTCACAGC
60301 TCAACCTCTT CATTTGGTTT CCAGATGCTA CTATCATTCA CGATGGCCAT
60351 GAGGAGAAGA TGGAAAATGG TCAGATCACA CCTGATGGCT TCCTGTCAAA
60401 ATCTGCTCCA TCAGAGCTTA TAAATATGAC AGGAGATGCT TATGCCACCC
60451 AACCAAGTGG ATTCTCTATC CTGACGACTT CACAAGTACT CAGCAAAGAT
60501 GGGCTGATTC AAAAACCTGG TAGTAACGCA TTTGTAGGAG GAGCCAAAAA
60551 CTGCAGTCTC TCCGTAGATG ACCAAAAAGA CCCAGTAGCA TCTACTTTGG
60601 GAGCTATGCC AAATACATTA CAAATCACTC CTGCTATGGC ACAAGGAATC
60651 AATGCTGATA TAAAACATCA ATTAATGAAG GAAGTTCGAA AGTTTGGTCG
60701 AAGTAAGTAG TGAAAGAACA TCTATCAATA ATGCACCAGG AGGTTTCTCT
60751 CATTCTGTGA TTCACTATAG ATTCAAGCTA TCCCTTGAGG TACACTGGGG
60801 GCAATATTGG GCTTTCACAT AGTTTAAGGC AGTTCCTCTT GTTTTAACTA
60851 AAAAGGTACA GTCTATATTT TCCTGTTTTT TCCCCTTATT TCTTGTAATG
60901 TTTCCTTTTG CTGCCGTAAC AAGTTATCAA AAGATTCCTA GCTTAAAACA
60951 ATACAAATTA TTATATTAAG TTCTGGAAGT CAGAATTTTG AAATTATTTT
61001 TGCTGGGCCA AAATAGTGTT GGCAGACCAG CATTCCTTCT GCTAGCTCTA
61051 GAGAGAATTT CTTTCTTTGC CTTTTCGAGC TTCTAAGGGC CATCTGTATT
61101 CCTTGGCCCA TGGCCCCTTC CTCCATCTTC ATGAAAACAC CCTTAGCACT
61151 TTTTCTCCTC TCTGACCTCT GCTTCTGTCT TTACATGTTT TCTCTCTGAC
61201 CTTAACTCTA CTGTTTCATC TTATAAGGAC ACTTGTGCTT ACATTGGGCC
61251 CACATGCATA AACTTGGATA ATCTCCCCAT CTCAAGATCC TTAACTTAAT
61301 TACACCTGCA AAGTAAAGTC TTTTTTGCTA TATAAGGTAA TGTATTCACA
61351 GGTTCCAGGG ATTAATATGT AGACAATTTT AAGCAGCTGC TATTCAGCCT
61401 GCTACATTTG GTTAGTGTTA ACAAGAGTTG CCCTAGTAGA TGCATGCAGA
61451 TATTTTGATA AGAATGTTAA AATACAAACT ACATCTAACT TTCCACTCAC
61501 GAAGAACAAT TACTAAGGAT GTACAACAAT TAAATTTTAT TTCCCATTCA
61551 TCTTTATAAA AATACTGAAG TTTTTTTAAA TATCTTCAGA ATATGAAAGA
61601 ATTTTCATTT TGCTTGAAGA AGTGCAAGGA CCTCTGGAGA TGAAGAAACA
61651 GTTTGTTGAA TTTACCATCA AGGAAGCCGC AAGGTAGGTA TAAACAGGAA
61701 CTCTTCAATT TTTTGTTTTT GTTTTAGAG CAGTAGGGCC CAGTGCAGGA
61751 AAAAGAGAGG AATAGGCTCT GCCTTGCTTT TTTCTCAAAC CCTGGCCCTC
61801 ACTCATAGTT AAGGCTGTCT CCAGAAGTAT TTGGATTTAT GTTATCTGAA
61851 CTCAACTCAT TCATCCTTCT ACTTTTATCA TAGCCTCAGG TAGGCTTGGG
61901 CCCTCAATTG CCACTATTGG TACTTGCTCT AAGACATATC TTTCCATGAG
61951 GACAATCTTT ATATTCCTAT GTAGATTGTA AGCTTCGATT TGTATCCCAC
62001 ACAGTGCCTT GAACATCATG AGTACTTTAA GTATCTTTTG GTTCATAAAA
62051 TTTCTCTTTA TTTTCAGGTT TAAAAGACGA GTCCTAATTC AGTACCTTGA
```

FIGURE 3W

```
62101  GAAGGTACTA GAAAAAATAA ATTCCCACCA CCTTCACAAC AACATTAGTC
62151  ACATCAACAG CAGATCATCA TGTTAGTGCA AAGACCAGTG AGAAAAAAAT
62201  GACAAGTTTT CTGTGCTGTA GGATGGAACA GGATATTGTT GAAGCCTCCT
62251  GGAATGTTTG AGTCAAGGGA ATTGCTTTCC AGATGCTAAG AAGCAGCAGT
62301  GGGGCTTTTT GAATTTTATG ATTATCTGGC AGTGAAAGCT GGGCTTTTGC
62351  CTTAATAATT TTTTAAAGTA TGAATTGTTT TGTTTTGTTT TCCTCAATTG
62401  AGGAAGCTGA TGTTATTAAT TCACAGGCTA AATTCGGTAA ACACCACTGC
62451  CCCTACCACG GGTAATGAGA GGTCACTCAC TTGAACTTTG CCATTCCAGG
62501  CATTCTCAGA GTGGCGAGGG GCCACCTGCA AGTGGAGCAC AACTTGGTGC
62551  TCTTACTGTG TCCTTCAGAA AGAATAGGTG TACAGAAAGG AAATGGCAAT
62601  CTTATGTGTG CTGAACAAAG TTTTCAACAA TTCCTAGTTG TGCCTTTTAA
62651  ACCATGCAAT ATTCAGGATA GTTTGAATCA AAGAAGTAAG AAGCTGCTAT
62701  TTGGGTAACT TATTTCTCTG TGGGAAGGGG CAGGGAGAGT CACCAAACAA
62751  TCTACCTCCA ACTCTCTTCT CTTTTGTCTA GAGACATTAC AAAGTGCACT
62801  TGAGGCTGCC CCCAACCTCT GACATTTGTT CTTGCATGTG ATGATAGAAA
62851  GTCTTCAGAT GGACTTATAC ATTCTGTGCT TTGGAAGCAC AAGAAGAACA
62901  AAATATGTGT ATATTTCCTT TAATGTTTAT ACAAAAGTTT ATATGGAGCA
62951  GTATTGTTAT GTTTGTATGA ATTTGCAAAA ATTAAAGTGT ACAAAGAGAT
63001  TTTGATTTTG CATATATAAA ATAAATCATT TTATTGATTT TCACAAGTTC
63051  ATTAATGCTG GATAAATTTC TACTTATATG TTTCTTGTGA TTTGTTACTC
63101  CTTTCAGAAA AAGAGTGTAT GCTGTTAAAC AAGTTAAGAT GTTAACATAA
63151  GGATTTAAAC TTCAAAACAT CACTCACAGA ATTGAGTGAC GCTAGTGAAA
63201  AATCACAGAG TAGAGTACCC ACGGACTAGT CACTTTCAAG AAACTTGGAA
63251  AACACTGGGG GAAAAAAAAA CCTGTCAGAA TCAAGTTTTA TTGGAACTCT
63301  AGAATATAGT AAAAGGTTTA CAGCAACCAA GCCAATCCTG AATTAGGAGA
63351  GAAGTCATTG AAACATGGTA GGGGAGCTTT GTGGCATTTC AACTCACCCT
63401  TGGAATGGCT GAGTAAGAAA GAAATTTGAG GCCAGGTGCA GTGGCCCACA
63451  TCTGTAATCC CAGCACTTTG GGAGGCCAAG GTGGGAAGAC CACTTGAGCC
63501  CAGGAGTTCA AGAGCAGCTT GGGCAACATG GCGAGACCCC ATCTCTCCAA
63551  AATATATGTA TTTTTAATTA GCTGGACGTG GTTGCACACA ATTGTGGTCC
63601  CAGCTACTCA GGAGACTCAG GTGGGAGGAC TGCTGGAGCC CAGGAGGTGG
63651  AGGCTGCAGT GAACTGTGAT CACACCACTG AACTCCAGCC TGAGCAACAG
63701  AGCAAGACCC TGTCTCAAAT AATAATATAT ACAAGCTGAC TTCTGAAATG
63751  GCATGGCTGC TTACTTCCCA CCTTCCTACC CCTCTCAAAC AAAGAGGGAG
63801  TTTTTGCATT TTCTATTCCT GGTTGCAAAA CACAAAGGAA AATGGAAAAA
63851  TAGTTTGTGT GCATTCATGA TATGCTTGCT CCTTTGAGAC TCTCAAACAG
63901  CCAGCACCAT CCCTTCCCAT AGCCTGCTAG GAGCCAAGAT GGCTTCCCAG
63951  TGCCTGTTTC TCGACCATTT TAATTTAAAA GCATGGTGAG TAGTATTAGC
64001  TGTGCCTTCT CTGCCACAGG AGAGAAAGCC TGGTCAAGAG GTGTGGTTTT
64051  GGATGCAATA AGTCCACTGC TTCTTGGAGA CGTTCCTGGA CATTCAATCG
64101  TGTCTTTCCT GGGTCCTTGG AGTAGTTGGT CAGGATGGGC TTCCCACTCA
64151  GTCCACGGGC CTGGGGCTGA TTCATGGTGG TCCCAGAGAC CTCAGCCCTC
64201  TGTGTTTGGC TGGAAGCCCA GAATGGTGTA CAGTTCCTCA GGCATGAGCC
64251  CCAGCAAGTT CTGGACGTCA CACAAAAAGC AGCACATATA GCACTTTCCC
64301  GACATCTTAT GGATGATGTT CTTGTCATGA TAGTAGGTAA ACCCAGGCTC
64351  AGCTTCTTGT AGTTCATCTT GGGCTTATTT TTCCTGATTC CCCACTGGCA
64401  GGCAACATTG TCAGGGTTGG CAAGTTTAAA CTCCCACCTG TCCCTATTCC
64451  AGCTGATGAA ATGACTGGCA AGACTGTCTA AAATTCCAGG AAAAACTGCT
64501  GTGGGTGAAT AGGTCCACTT TCTGTGAAGC CAGACAGCAC AGCCACAGGT
64551  ATAACTGGTT TGCCTTGCTC CACCGGGTTG CTCCTCTCTT GGATGTAATC
64601  CTTGAAAGGC ATGGTCAACT TTTTGAGGCA GGGGGACTGA CTGCAGTTTT
64651  CTTTGAAGCT CTCGAAGAAA GGAACCTGCT GCACATCCAG TAAGGATGAC
64701  TGGTTGTTCC AGGTGCCTGA GCTCTCAAAG CTGTCTGCCT CATGATTTAA
64751  ATGTTAAAAA AGCAGACAGC TTTAAATGTC TGCACCATTC TCAGGGGATT
```

FIGURE 3X

```
64801 TGTGGTCTTT AGGCTTCCCA GAATTGTTGG TGAGCAAATT CAAGTTGCCT
64851 AGAAAGTCCT GACTGATGGA GCATAGTTGA GGCTGATAGA GCTGAGCTGA
64901 GACTTGGAGA ACATCTGAAA CTCCTGTTCA GAGCTGAGCA CGCTGGGTGC
64951 AGAAGCTGGA CACATGCTGT CCAGGAGGCT GCCTTTGGGG TAATTGTGTG
65001 TTTGCATACC ATAGGGTACC TGCTTTATGC CAAAACCTAA TG  (SEQ ID NO:3)
```

FEATURES:
Start:    2321
Exon:     2321-2431
Intron:   2432-2568
Exon:     2569-2633
Intron:   2634-3279
Exon:     3280-3282
Intron:   3283-21752
Exon:     21753-21758
Intron:   21759-25658
Exon:     25659-25662
Intron:   25663-26395
Exon:     26396-26545
Intron:   26546-27352
Exon:     27353-27442
Intron:   27443-27674
Exon:     27675-27860
Intron:   27861-28111
Exon:     28112-28240
Intron:   28241-30619
Exon:     30620-30783
Intron:   30784-32812
Exon:     32813-32965
Intron:   32966-36995
Exon:     36996-37128
Intron:   37129-49773
Exon:     49774-49872
Intron:   49873-50931
Exon:     50932-51030
Intron:   51031-51675
Exon:     51676-51790
Intron:   51791-54471
Exon:     54472-54595
Intron:   54596-55615
Exon:     55616-55758
Intron:   55759-57729
Exon:     57730-57964
Intron:   57965-60324
Exon:     60325-60702
Intron:   60703-61589
Exon:     61590-61683
Intron:   61684-62067
Exon:     62068-62173
Stop:     62174

CHROMSOME MAP POSITION:
Chromosome X

FIGURE 3Y

ISOLATED NUCLEIC ACID MOLECULES ENCODING HUMAN ENZYME PROTEINS, AND USES THEREOF

FIELD OF THE INVENTION

The present invention is in the field of enzyme proteins that are related to the helicase subfamily, recombinant DNA molecules, and protein production. The present invention specifically provides novel peptides and proteins that effect protein phosphorylation and nucleic acid molecules encoding such peptide and protein molecules, all of which are useful in the development of human therapeutics and diagnostic compositions and methods.

BACKGROUND OF THE INVENTION

Many human enzymes serve as targets for the action of pharmaceutically active compounds. Several classes of human enzymes that serve as such targets include helicase, steroid esterase and sulfatase, convertase, synthase, dehydrogenase, monoxygenase, transferase, kinase, glutanase, decarboxylase, isomerase and reductase. It is therefore important in developing new pharmaceutical compounds to identify target enzyme proteins that can be put into high-throughput screening formats. The present invention advances the state of the art by providing novel human drug target enzymes related to the helicase subfamily.

Helicases

The novel human enzyme, and encoding gene is similar to the RNA helicase HDB protein, also known as the DICE1 ("deleted in cancer 1") protein.

DICE1 is a candidate tumor suppressor gene, particularly in non-small cell lung carcinomas, and carcinomas of the head and neck, breast, ovary, prostate, as well as other carcinomas. DICE1 is expressed in a wide variety of adult and fetal tissues and is highly conserved in evolution, it's expression is down-regulated or abolished in carcinomas, and it is located in a chromosomal region associated with tumor suppression and loss of heterozygosity. DICE1 shares 92.9% amino acid sequence identity with the carboxyterminal half of mouse EGF repeat transmembrane protein DB-1, a protein that limits mitogenic response to insulin-like growth factor 1 and likely plays a role in anchorage-dependent growth (Wieland et al, *Oncogene* 18: 4530–4537, 1999).

Therefore, novel human helicase proteins/genes may be particularly useful in the diagnosis, prevention, and/or treatment of carcinomas.

Enzyme proteins, particularly members of the helicase subfamily, are a major target for drug action and development. Accordingly, it is valuable to the field of pharmaceutical development to identify and characterize previously unknown members of this subfamily of enzyme proteins. The present invention advances the state of the art by providing previously unidentified human enzyme proteins, and the polynucleotides encoding them, that have homology to members of the helicase subfamily. These novel compositions are useful in the diagnosis, prevention and treatment of biological processes associated with human diseases.

SUMMARY OF THE INVENTION

The present invention is based in part on the identification of amino acid sequences of human enzyme peptides and proteins that are related to the helicase subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate enzyme activity in cells and tissues that express the enzyme. Experimental data as provided in FIG. 1 indicates expression in humans in the fetal liver/spleen, breast, hypothalamus, ovarian tumors, lung fibroblasts, and brain.

DESCRIPTION OF THE FIGURE SHEETS

FIG. 1 provides the nucleotide sequence of a cDNA molecule that encodes the enzyme protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in humans in the fetal liver/spleen, breast, hypothalamus, ovarian tumors, lung fibroblasts, and brain.

FIG. 2 provides the predicted amino acid sequence of the enzyme of the present invention. (SEQ ID NO:2) In addition structure and functional information such as protein family, function, and modification sites is provided where available, allowing one to readily determine specific uses of inventions based on this molecular sequence.

FIG. 3 provides genomic sequences that span the gene encoding the enzyme protein of the present invention. (SEQ ID NO:3) In addition structure and functional information, such as intron/exon structure, promoter location, etc., is provided where available, allowing one to readily determine specific uses of inventions based on this molecular sequence.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a enzyme protein or part of a enzyme protein and are related to the helicase subfamily. Utilizing these sequences, additional genomic sequences were assembled and transcript and/or cDNA sequences were isolated and characterized. Based on this analysis, the present invention provides amino acid sequences of human enzyme peptides and proteins that are related to the helicase subfamily, nucleic acid sequences in the form of transcript sequences, cDNA sequences and/or genomic sequences that encode these enzyme peptides and proteins, nucleic acid variation (allelic information), tissue distribution of expression, and information about the closest art known protein/peptide/domain that has structural or sequence homology to the enzyme of the present invention.

In addition to being previously unknown, the peptides that are provided in the present invention are selected based on their ability to be used for the development of commercially important products and services. Specifically, the present peptides are selected based on homology and/or structural relatedness to known enzyme proteins of the helicase subfamily and the expression pattern observed. Experimental data as provided in FIG. 1 indicates expression in humans in the fetal liver/spleen, breast, hypothalamus, ovarian tumors, lung fibroblasts, and brain. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known helicase family or subfamily of enzyme proteins.

Specific Embodiments

Peptide Molecules

The present invention provides nucleic acid sequences that encode protein molecules that have been identified as being members of the enzyme family of proteins and are related to the helicase subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the enzyme peptides of the present invention, enzyme peptides, or peptides/proteins of the present invention.

The present invention provides isolated peptide and protein molecules that consist of, consist essentially of, or comprise the amino acid sequences of the enzyme peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the enzyme peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated enzyme peptide can be purified from cells that naturally express it, purified from cells that have been altered to express it (recombinant), or synthesized using known protein synthesis methods. Experimental data as provided in FIG. 1 indicates expression in humans in the fetal liver/spleen, breast, hypothalamus, ovarian tumors, lung fibroblasts, and brain. For example, a nucleic acid molecule encoding the enzyme peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the enzyme peptides of the present invention are the naturally occurring mature proteins. A brief description of how various types of these proteins can be made/isolated is provided below.

The enzyme peptides of the present invention can be attached to heterologous sequences to form chimeric or fusion proteins. Such chimeric and fusion proteins comprise a enzyme peptide operatively linked to a heterologous protein having an amino acid sequence not substantially homologous to the enzyme peptide. "Operatively linked" indicates that the enzyme peptide and the heterologous protein are fused in-frame. The heterologous protein can be fused to the N-terminus or C-terminus of the enzyme peptide.

In some uses, the fusion protein does not affect the activity of the enzyme peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant enzyme peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A enzyme peptide-encoding nucleic acid can be cloned into such an expression vector such that the fusion moiety is linked in-frame to the enzyme peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the enzyme peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part* 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the enzyme peptides of the present invention as well as being encoded by the same genetic locus as the enzyme peptide provided herein. The gene encoding the novel enzyme of the present invention is located on a genome component that has been mapped to human chromosome X (as indicated in FIG. 3), which is supported by multiple lines of evidence, such as STS and BAC map data.

Allelic variants of a enzyme peptide can readily be identified as being a human protein having a high degree (significant) of sequence homology/identity to at least a portion of the enzyme peptide as well as being encoded by the same genetic locus as the enzyme peptide provided herein. Genetic locus can readily be determined based on the genomic information provided in FIG. 3, such as the genomic sequence mapped to the reference human. The gene encoding the novel enzyme of the present invention is located on a genome component that has been mapped to human chromosome X (as indicated in FIG. 3), which is supported by multiple lines of evidence, such as STS and BAC map data. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a enzyme peptide encoding nucleic acid molecule under stringent conditions as more fully described below.

Paralogs of a enzyme peptide can readily be identified as having some degree of significant sequence homology/identity to at least a portion of the enzyme peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a enzyme peptide encoding nucleic acid molecule under moderate to stringent conditions as more fully described below.

Orthologs of a enzyme peptide can readily be identified as having some degree of significant sequence homology/identity to at least a portion of the enzyme peptide as well as being encoded by a gene from another organism. Preferred orthologs will be isolated from mammals, preferably primates, for the development of human therapeutic targets and agents. Such orthologs will be encoded by a nucleic acid sequence that will hybridize to a enzyme peptide encoding nucleic acid molecule under moderate to stringent conditions, as more fully described below, depending on the degree of relatedness of the two organisms yielding the proteins.

Non-naturally occurring variants of the enzyme peptides of the present invention can readily be generated using recombinant techniques. Such variants include, but are not limited to deletions, additions and substitutions in the amino acid sequence of the enzyme peptide. For example, one class of substitutions are conserved amino acid substitution. Such substitutions are those that substitute a given amino acid in a enzyme peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant enzyme peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as enzyme activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the enzyme peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a enzyme peptide. Such fragments can be chosen based on the ability to retain one or more of the biological activities of the enzyme peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the enzyme peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in enzyme peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the enzyme peptides of the present invention also encompass derivatives or analogs in which a substituted amino acid residue is not one encoded by the genetic code, in which a substituent group is included, in which the mature enzyme peptide is fused with another compound, such as a compound to increase the half-life of the enzyme peptide (for example, polyethylene glycol), or in which the additional amino acids are fused to the mature enzyme peptide, such as a leader or secretory sequence or a sequence for purification of the mature enzyme peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a enzyme-effector protein interaction or enzyme-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, enzymes isolated from humans and their human/mammalian orthologs serve as targets for identifying agents for use in mammalian therapeutic applications, e.g. a human drug, particularly in modulating a biological or pathological response in a cell or tissue that expresses the enzyme. Experimental data as provided in FIG. 1 indicates that the enzymes of the present invention are expressed in humans in fetal liver/spleen, breast, hypothalamus, ovarian tumors, and lung fibroblasts, as indicated by virtual northern blot analysis. In addition, PCR-based tissue screening panels indicate expression in the human brain. A large percentage of pharmaceutical agents are being developed that modulate the activity of enzyme proteins, particularly members of the helicase subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in humans in the fetal liver/spleen, breast, hypothalamus, ovarian tumors, lung fibroblasts, and brain. Such uses can readily be determined using the information provided herein, that which is known in the art, and routine experimentation.

The proteins of the present invention (including variants and fragments that may have been disclosed prior to the present invention) are useful for biological assays related to enzymes that are related to members of the helicase subfamily. Such assays involve any of the known enzyme functions or activities or properties useful for diagnosis and treatment of enzyme-related conditions that are specific for the subfamily of enzymes that the one of the present invention belongs to, particularly in cells and tissues that express the enzyme. Experimental data as provided in FIG. 1 indicates that the enzymes of the present invention are expressed in humans in fetal liver/spleen, breast, hypothalamus, ovarian tumors, and lung fibroblasts, as indicated by virtual northern blot analysis. In addition, PCR-based tissue screening panels indicate expression in the human brain.

The proteins of the present invention are also useful in drug screening assays, in cell-based or cell-free systems. Cell-based systems can be native, i.e., cells that normally express the enzyme, as a biopsy or expanded in cell culture. Experimental data as provided in FIG. 1 indicates expression in humans in the fetal liver/spleen, breast, hypothalamus, ovarian tumors, lung fibroblasts, and brain. In an alternate embodiment, cell-based assays involve recombinant host cells expressing the enzyme protein.

The polypeptides can be used to identify compounds that modulate enzyme activity of the protein in its natural state or an altered form that causes a specific disease or pathology associated with the enzyme. Both the enzymes of the present invention and appropriate variants and fragments can be used in high-throughput screens to assay candidate compounds for the ability to bind to the enzyme. These compounds can be further screened against a functional enzyme to determine the effect of the compound on the enzyme activity. Further, these compounds can be tested in animal or invertebrate systems to determine activity/effectiveness. Compounds can be identified that activate (agonist) or inactivate (antagonist) the enzyme to a desired degree.

Further, the proteins of the present invention can be used to screen a compound for the ability to stimulate or inhibit interaction between the enzyme protein and a molecule that normally interacts with the enzyme protein, e.g. a substrate or a component of the signal pathway that the enzyme protein normally interacts (for example, another enzyme). Such assays typically include the steps of combining the enzyme protein with a candidate compound under conditions that allow the enzyme protein, or fragment, to interact with the target molecule, and to detect the formation of a complex between the protein and the target or to detect the biochemical consequence of the interaction with the enzyme protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant enzymes or appropriate fragments containing mutations that affect enzyme function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) enzyme activity. The assays typically involve an assay of events in the signal transduction pathway that indicate enzyme activity. Thus, the phosphorylation of a substrate, activation of a protein, a change in the expression of genes that are up- or down-regulated in response to the enzyme protein dependent signal cascade can be assayed.

Any of the biological or biochemical functions mediated by the enzyme can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the enzyme can be assayed. Experimental data as provided in FIG. 1 indicates that the enzymes of the present invention are expressed in humans in fetal liver/spleen, breast, hypothalamus, ovarian tumors, and lung fibroblasts, as indicated by virtual northern blot analysis. In addition, PCR-based tissue screening panels indicate expression in the human brain.

Binding and/or activating compounds can also be screened by using chimeric enzyme proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native enzyme. Accordingly, a different set of signal transduction components is available as an end-point assay for activation. This allows for assays to be performed in other than the specific host cell from which the enzyme is derived.

The proteins of the present invention are also useful in competition binding assays in methods designed to discover compounds that interact with the enzyme (e.g. binding partners and/or ligands). Thus, a compound is exposed to a enzyme polypeptide under conditions that allow the compound to bind or to otherwise interact with the polypeptide. Soluble enzyme polypeptide is also added to the mixture. If the test compound interacts with the soluble enzyme polypeptide, it decreases the amount of complex formed or activity from the enzyme target. This type of assay is particularly useful in cases in which compounds are sought that interact with specific regions of the enzyme. Thus, the soluble polypeptide that competes with the target enzyme region is designed to contain peptide sequences corresponding to the region of interest.

To perform cell free drug screening assays, it is sometimes desirable to immobilize either the enzyme protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of enzyme-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a enzyme-binding protein and a candidate compound are incubated in the enzyme protein-presenting wells and the amount of complex trapped in the well can be quantitated. Methods for detecting such complexes, in addition to those described above for the GST-immobilized complexes, include immunodetection of complexes using antibodies reactive with the enzyme protein target molecule, or which are reactive with enzyme protein and compete with the target molecule, as well as enzyme-linked assays which rely on detecting an enzymatic activity associated with the target molecule.

Agents that modulate one of the enzymes of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of enzyme protein activity identified according to these drug screening assays can be used to treat a subject with a disorder mediated by the enzyme pathway, by treating cells or tissues that express the enzyme. Experimental data as provided in FIG. 1 indicates expression in humans in the fetal liver/spleen, breast, hypothalamus, ovarian tumors, lung fibroblasts, and brain. These methods of treatment include the steps of administering a modulator of enzyme activity in a pharmaceutical composition to a subject in need of such treatment, the modulator being identified as described herein.

In yet another aspect of the invention, the enzyme proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the enzyme and are involved in enzyme activity. Such enzyme-binding proteins are also likely to be involved in the propagation of signals by the enzyme proteins or enzyme targets as, for example, downstream elements of a enzyme-mediated signaling pathway. Alternatively, such enzyme-binding proteins are likely to be enzyme inhibitors.

The two-hybrid system is based on the modular nature of most transcription factors, which consist of separable DNA-binding and activation domains. Briefly, the assay utilizes two different DNA constructs. In one construct, the gene that codes for a enzyme protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a enzyme-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the enzyme protein.

This invention further pertains to novel agents identified by the above-described screening assays. Accordingly, it is within the scope of this invention to further use an agent identified as described herein in an appropriate animal model. For example, an agent identified as described herein (e.g., a enzyme-modulating agent, an antisense enzyme nucleic acid molecule, a enzyme-specific antibody, or a enzyme-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The enzyme proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in humans in the fetal liver/spleen, breast, hypothalamus, ovarian tumors, lung fibroblasts, and brain. The method involves contacting a biological sample with a compound capable of interacting with the enzyme protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered enzyme activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (Clin. Exp. Pharmacol. Physiol. 23(10–11):983–985 (1996)), and Linder, M. W. (Clin. Chem. 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the enzyme protein in which one or more of the enzyme function in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and enzyme activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in humans in the fetal liver/spleen, breast, hypothalamus, ovarian tumors, lung fibroblasts, and brain. Accordingly, methods for treatment include the use of the enzyme protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the enzyme proteins. Antibodies can be prepared from any region of the peptide as described herein. However, preferred regions will include those involved in function/activity and/or enzyme/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^3$H.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that the enzymes of the present invention are expressed in humans in fetal liver/spleen, breast, hypothalamus, ovarian tumors, and lung fibroblasts, as indicated by virtual northern blot analysis. In addition, PCR-based tissue screening panels indicate expression in the human brain. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in humans in the fetal liver/spleen, breast, hypothalamus, ovarian tumors, lung fibroblasts, and brain. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in humans in the fetal liver/spleen, breast, hypothalamus, ovarian tumors, lung fibroblasts, and brain. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in humans in the fetal liver/spleen, breast, hypothalamus, ovarian tumors, lung fibroblasts, and brain. Thus, where a specific protein has been correlated with expression in a specific tissue, antibodies that are specific for this protein can be used to identify a tissue type.

The antibodies are also useful for inhibiting protein function, for example, blocking the binding of the enzyme peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a enzyme peptide or protein of the present invention (cDNA, transcript and genomic sequence). Such nucleic acid molecules will consist of, consist essentially of, or comprise a nucleotide sequence that encodes one of the enzyme peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the enzyme peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

The invention further provides nucleic acid molecules that encode fragments of the peptides of the present invention as well as nucleic acid molecules that encode obvious variants of the enzyme proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. The gene encoding the novel enzyme of the present invention is located on a genome component that has been mapped to human chromosome X (as indicated in FIG. 3), which is supported by multiple lines of evidence, such as STS and BAC map data.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6×sodium chloride/sodium citrate (SSC) at about 45C., followed by one or more washes in 0.2×SSC, 0.1% SDS at 50–65C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. The gene encoding the novel enzyme of the present invention is located on a genome component that has been mapped to human chromosome X (as indicated in FIG. 3), which is supported by multiple lines of evidence, such as STS and BAC map data.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that the enzymes of the present invention are expressed in humans in fetal liver/spleen, breast, hypothalamus, ovarian tumors, and lung fibroblasts, as indicated by virtual northern blot analysis. In addition, PCR-based tissue screening panels indicate expression in the human brain. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in enzyme protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a enzyme protein, such as by measuring a level of a enzyme-encoding nucleic acid in a sample of cells from a subject e.g., mRNA or genomic DNA, or determining if a enzyme gene has been mutated. Experimental data as provided in FIG. 1 indicates that the enzymes of the present invention are expressed in humans in fetal liver/spleen, breast, hypothalamus, ovarian tumors, and lung fibroblasts, as indicated by virtual northern blot analysis. In addition, PCR-based tissue screening panels indicate expression in the human brain.

Nucleic acid expression assays are useful for drug screening to identify compounds that modulate enzyme nucleic acid expression.

The invention thus provides a method for identifying a compound that can be used to treat a disorder associated with nucleic acid expression of the enzyme gene, particularly biological and pathological processes that are mediated by the enzyme in cells and tissues that express it. Experimental data as provided in FIG. 1 indicates expression in humans in the fetal liver/spleen, breast, hypothalamus, ovarian tumors, lung fibroblasts, and brain. The method typically includes assaying the ability of the compound to modulate the expression of the enzyme nucleic acid and thus identifying a compound that can be used to treat a disorder characterized by undesired enzyme nucleic acid expression. The assays can be performed in cell-based and cell-free systems. Cell-based assays include cells naturally expressing the enzyme nucleic acid or recombinant cells genetically engineered to express specific nucleic acid sequences.

The assay for enzyme nucleic acid expression can involve direct assay of nucleic acid levels, such as mRNA levels, or on collateral compounds involved in the signal pathway. Further, the expression of genes that are up- or down-regulated in response to the enzyme protein signal pathway can also be assayed. In this embodiment the regulatory regions of these genes can be operably linked to a reporter gene such as luciferase.

Thus, modulators of enzyme gene expression can be identified in a method wherein a cell is contacted with a candidate compound and the expression of mRNA determined. The level of expression of enzyme mRNA in the presence of the candidate compound is compared to the level of expression of enzyme mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate enzyme nucleic acid expression in cells and tissues that express the enzyme. Experimental data as provided in FIG. 1 indicates that the enzymes of the present invention are expressed in humans in fetal liver/spleen, breast, hypothalamus, ovarian tumors, and lung fibroblasts, as indicated by virtual northern blot analysis. In addition, PCR-based tissue screening panels indicate expression in the human brain. Modulation includes both up-regulation (i.e. activation or agonization) or down-regulation (suppression or antagonization) or nucleic acid expression.

Alternatively, a modulator for enzyme nucleic acid expression can be a small molecule or drug identified using the screening assays described herein as long as the drug or small molecule inhibits the enzyme nucleic acid expression in the cells and tissues that express the protein. Experimental data as provided in FIG. 1 indicates expression in humans in the fetal liver/spleen, breast, hypothalamus, ovarian tumors, lung fibroblasts, and brain.

The nucleic acid molecules are also useful for monitoring the effectiveness of modulating compounds on the expression or activity of the enzyme gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in enzyme nucleic acid expression, and particularly in qualitative changes that lead to pathology. The nucleic acid molecules can be used to detect mutations in enzyme genes and gene expression products such as mRNA. The nucleic acid molecules can be used as hybridization probes to detect naturally occurring genetic mutations in the enzyme gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the enzyme gene associated with a dys function provides a diagnostic tool for an active disease or susceptibility to disease when the disease results from overexpression, underexpression, or altered expression of a enzyme protein.

Individuals carrying mutations in the enzyme gene can be detected at the nucleic acid level by a variety of techniques. The gene encoding the novel enzyme of the present invention is located on a genome component that has been mapped to human chromosome X (as indicated in FIG. 3), which is supported by multiple lines of evidence, such as STS and BAC map data. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., Science 241:1077–1080 (1988); and Nakazawa et al., PNAS 91:360–364 (1994)), the latter of which can be particularly useful for detecting point mutations in the gene (see Abravaya et al., Nucleic Acids Res. 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a enzyme gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant enzyme gene and a wild-type gene can be determined by direct DNA sequencing. A variety of automated sequencing procedures can be utilized when performing the diagnostic assays (Naeve, C. W., (1995) Biotechniques 19:448), including sequencing by mass spectrometry (see, e.g., PCT International Publication No. WO 94/16101; Cohen et al., Adv. Chromatogr. 36:127–162 (1996); and Griffin et al., Appl. Biochem. Biotechnol. 38:147–159 (1993)).

Other methods for detecting mutations in the gene include methods in which protection from cleavage agents is used to detect mismatched bases in RNA/RNA or RNA/DNA duplexes (Myers et al., Science 230:1242 (1985)); Cotton et al., PNAS 85:4397 (1988); Saleeba et al., Meth. Enzymol. 217:286–295 (1992)), electrophoretic mobility of mutant and wild type nucleic acid is compared (Orita et al., PNAS 86:2766 (1989); Cotton et al., Mutat. Res. 285:125–144 (1993); and Hayashi et al., Genet. Anal. Tech. Appl. 9:73–79 (1992)), and movement of mutant or wild-type fragments in polyacrylamide gels containing a gradient of denaturant is assayed using denaturing gradient gel electrophoresis (Myers et al., Nature 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the enzyme gene in an individual in order to select an appropriate compound or dosage regimen for treatment.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control enzyme gene expression in cells, tissues, and organisms. A DNA antisense nucleic acid molecule is designed to be complementary to a region of the gene involved in transcription, preventing transcription and hence production of enzyme protein. An antisense RNA or DNA nucleic acid molecule would hybridize to the mRNA and thus block translation of mRNA into enzyme protein.

Alternatively, a class of antisense molecules can be used to inactivate mRNA in order to decrease expression of enzyme nucleic acid. Accordingly, these molecules can treat a disorder characterized by abnormal or undesired enzyme nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the enzyme protein, such as substrate binding.

The nucleic acid molecules also provide vectors for gene therapy in patients containing cells that are aberrant in enzyme gene expression. Thus, recombinant cells, which include the patient's cells that have been engineered ex vivo and returned to the patient, are introduced into an individual where the cells produce the desired enzyme protein to treat the individual.

The invention also encompasses kits for detecting the presence of a enzyme nucleic acid in a biological sample. Experimental data as provided in FIG. 1 indicates that the enzymes of the present invention are expressed in humans in fetal liver/spleen, breast, hypothalamus, ovarian tumors, and lung fibroblasts, as indicated by virtual northern blot analysis. In addition, PCR-based tissue screening panels indicate expression in the human brain. For example, the kit can comprise reagents such as a labeled or labelable nucleic acid or agent capable of detecting enzyme nucleic acid in a biological sample; means for determining the amount of enzyme nucleic acid in the sample; and means for comparing the amount of enzyme nucleic acid in the sample with a standard. The compound or agent can be packaged in a suitable container. The kit can further comprise instructions for using the kit to detect enzyme protein mRNA or DNA. Nucleic Acid Arrays The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. 5,837, 832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the enzyme proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the enzyme gene of the present invention.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified enzyme gene of the present invention can be routinely identified using the sequence information disclosed herein can be readily incorporated into one of the established kit formats which are well known in the art, particularly expression arrays.

Vectors/host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from $E.\ coli$, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual. 2nd. ed.*, Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual. 2nd. ed.*, Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, $E.\ coli$, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enteroenzyme. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., Gene 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990) 119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as enzymes, appropriate secretion signals are incorporated into the vector. The signal sequence can be endogenous to the peptides or heterologous to these peptides.

Where the peptide is not secreted into the medium, which is typically the case with enzymes, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a enzyme protein or peptide that can be further purified to produce desired amounts of enzyme protein or fragments. Thus, host cells containing expression vectors are useful for peptide production.

Host cells are also useful for conducting cell-based assays involving the enzyme protein or enzyme protein fragments, such as those described above as well as other formats known in the art. Thus, a recombinant host cell expressing a native enzyme protein is useful for assaying compounds that stimulate or inhibit enzyme protein function.

Host cells are also useful for identifying enzyme protein mutants in which these functions are affected. If the mutants naturally occur and give rise to a pathology, host cells containing the mutations are useful to assay compounds that have a desired effect on the mutant enzyme protein (for example, stimulating or inhibiting function) which may not be indicated by their effect on the native enzyme protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a enzyme protein and identifying and evaluating modulators of enzyme protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the enzyme protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the enzyme protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al, U.S. Pat. No. 4,873,191 by Wagner et al. and in Hogan, B., *Manipulating the Mouse Embryo* (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, enzyme protein activation, and signal transduction, may not be evident from in vitro cell-free or cell-based assays. Accordingly, it is useful to provide non-human transgenic animals to assay in vivo enzyme protein function, including substrate interaction, the effect of specific mutant enzyme proteins on enzyme protein function and substrate interaction, and the effect of chimeric enzyme proteins. It is also possible to assess the effect of null mutations, that is, mutations that substantially or completely eliminate one or more enzyme protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated nucleic acid molecule encoding a DEAD-box RNA helicase, wherein the nucleic acid molecule consists of a nucleotide sequence selected from the group consisting of:

(a) a nucleotide sequence that encodes a protein comprising the amino acid sequence of SEQ ID NO:2; and (b) a nucleotide sequence consisting of SEQ ID NO:1.

2. A nucleic acid vector comprising the nucleic acid molecule of claim 1.

3. A host cell containing the vector of claim 2.

4. A process for producing a polypeptide comprising SEQ ID NO:2, the process comprising culturing the host cell of claim 3 under conditions sufficient for the production of said polypeptide, and recovering said polypeptide from the host cell culture.

5. An isolated polynucleotide encoding a DEAD-box RNA helicase wherein the polynucleotide consists of the nucleotide sequence set forth in SEQ ID NO:1.

6. A vector according to claim 2, wherein said vector is selected from the group consisting of a plasmid, virus, and bacteriophage.

7. a vector according to claims 2, wherein said isolated nucleic acid molecule is inserted into said vector in proper orientation and correct reading frame such that the protein of SEQ ID NO:2 may be expressed by a cell transformed with said vector.

8. A vector according to claim 7, wherein said isolated nucleic acid molecule is operatively linked to a promoter sequence.

9. An isolated nucleic acid molecule consisting of a nucleotide sequence that is completely complementary to the nucleotide sequence of claim 7.

* * * * *

SEQUENCE LISTING

<160> NUMBER OF SEQ ID NOS: 5

<210> SEQ ID NO 1
<211> LENGTH: 3812
<212> TYPE: DNA
<213> ORGANISM: Human

<400> SEQUENCE: 1

| | | | | | | |
|---|---|---|---|---|---|---|
| cgctctagtg | agcgcggacg | gatgcttagg | cagtagtcct | ggcagcggca | gtagtggtgg | 60 |
| cagcagaaga | gaggaagggg | gagggccccg | agggctacac | acgctcacac | tttcaagttc | 120 |
| ccttggaggg | agaggaggtg | gggctgcaga | aagaggaggc | caggagcggt | cccatccgtc | 180 |
| ccgtcccgtc | ccgtctcccc | ctcttcctct | tgctccttgc | ccccggctc | tgcgagagtt | 240 |
| gagggttcag | gtggccgtac | gcggcagtga | gggcaagagg | gccgggagag | tggggagcgg | 300 |
| aggcaggagt | gcggggaag | atgcccatcc | tgctgttcct | catagacacg | tccgcctcta | 360 |
| tgaaccagcg | cactgacctg | ggcacctctt | atttggacat | tgccaaaggc | gctgtggagt | 420 |
| tattcttgaa | gctgcgcgcc | cgggacccgg | ccagccgtgg | agacaggtac | atgctggtca | 480 |
| cctacgacga | accccgtac | tgcatcaagg | ctggttggaa | ggaaaatcat | gcaacattca | 540 |
| tgagcgaact | aaaaaatctt | caggcttctg | gactgactac | tctcggtcag | gctctaagat | 600 |
| cctcatttga | tttgttaaat | ctcaatagat | taatatctgg | aatagacaat | tatggacagg | 660 |
| ggagaaatcc | attttttta | gaaccatcta | ttttaattac | catcacagat | ggaaacaagt | 720 |
| taacaagtac | tgctggtgtt | caagaagagc | tccatcttcc | tttgaattcc | cctctgcctg | 780 |
| gaagtgaact | aaccaaagaa | ccttttcgtt | gggatcaaag | gttatttgcc | ctggtgttgc | 840 |
| gtttgcctgg | agtggcttct | accgaaccag | agcaactagg | gagcgtacca | actgatgaat | 900 |
| ctgccatcac | acagatgtgt | gaagtcacag | gaggtcgctc | ctactgtgtg | agaacacaaa | 960 |
| gaatgttgaa | tcaatgttta | gaatctctag | ttcaaaaagt | tcagagtggt | gtagttatta | 1020 |
| attttgaaaa | aacaggacca | gatccacttc | ctattggaga | agatggactt | atggattcat | 1080 |
| ccaggccaag | caattcattt | gctgctcagc | catggcatag | ttgtcataaa | ctcatttatg | 1140 |
| tacgacctaa | ctctaaaact | ggtgttcctg | ttggacattg | gccaattcca | gaatcttttt | 1200 |
| ggccagatca | gaatttacct | tcactacctc | cacgaacatc | tcatcctgtt | gtgaggttct | 1260 |
| cctgtgtaga | ttgtgagcca | atggtaatag | acaaacttcc | ttttgacaaa | tatgaacttg | 1320 |
| aaccttcgcc | cttaactcag | tatatcttgg | aacgaaagtc | tccccatacc | tgctggcagg | 1380 |
| tatttgttac | tagcagtgga | aagtacaatg | aacttggata | tccattttggt | tatttaaaag | 1440 |
| ccagtacaac | tttaacttgt | gtaaacctct | ttgtgatgcc | ttacaactac | ccagttttac | 1500 |
| ttcctctttt | agatgacttg | tttaaagttc | acaagcttaa | gccaaatctg | aagtggcgac | 1560 |
| aggcttttga | cagctactta | aaaactctgc | ctccatacta | cctattaacc | aaactagagt | 1620 |
| cagaacgaat | actagcatca | gtggggaaga | aacctcccca | ggaaattgga | attaaagtga | 1680 |
| aaaatcattc | tggaggtggc | atgtccttga | ctcacaataa | aaatttaga | aaactattga | 1740 |
| aagaaatcac | agggaaact | gcacttagac | tgacagaatt | gaacaccaaa | gaatttgctg | 1800 |
| gcttccaaat | tgggctctta | aacaaggatt | tgaaacctca | gacatacaga | aatgcttatg | 1860 |
| atattccccg | tagaggtctt | ttagaccagc | tgaccagaat | gagatccaat | ctgctgaaaa | 1920 |
| cgcacaagtt | tattgttgga | caagatgaag | attcccttca | tagtgttcca | gttgcacaaa | 1980 |
| tgggtaacta | tcaggaatat | ctgaagacat | tggcttctcc | actgcgagag | attgatccag | 2040 |

-continued

```
accaacccaa aagactgcat acttttggca atccgtttaa acaagataag aagggaatga    2100
tgattgatga agcagatgag tttgtagcag ggccacaaaa caaagtgaaa cgtccagggg    2160
aacccaacag tcctatgtca tctaagagaa ggcggagtat gtccctgctg ttgaggaaac    2220
cacaaacacc acctactgta actaaccatg tgggcggaaa gggaccaccc tcagcctcgt    2280
ggttcccatc ttatccaaac ctcataaaac ccacccttgt acatacagat gctactatca    2340
ttcacgatgg ccatgaggag aagatggaaa atggtcagat cacacctgat ggcttcctgt    2400
caaaatctgc tccatcagag cttataaata tgacaggaga tcttatgcca cccaaccaag    2460
tggattctct gtctgacgac ttcacaagtc tcagcaaaga tgggctgatt caaaaacctg    2520
gtagtaacgc atttgtagga ggagccaaaa actgcagtct ctccgtagat gaccaaaaag    2580
acccagtagc atctactttg ggagctatgc caaatacatt acaaatcact cctgctatgg    2640
cacaaggaat caatgctgat ataaaacatc aattaatgaa ggaagttcga aagtttggtc    2700
gaaaatatga aagaattttc attttgcttg aagaagtgca aggacctctg gagatgaaga    2760
aacagtttgt tgaatttacc atcaaggaag ccgcaagggt taaagacga gtcctaattc    2820 agtaccttga aaggtacta gaaaaaataa attcccacca ccttcacaac aacattagtc    2880
acatcaacag cagatcatca tgttagtgca aagaccagtg agaaaaaaat gacaagtttt    2940
ctgtgctgta ggatggaaca ggatattgtt gaagcctcct ggaatgtttg agtcaaggga    3000
attgctttcc agatgctaag aagcagcagt ggggcttttg aattttatga ttatctggca    3060
gtgaaagctg gcttttgcc ttaataattt tttaaagtat gaattgtttt gttttgtttt    3120
cctcaattga ggaagctgat gttattaatt cacaggctaa attcggtaaa caccactgcc    3180
cctaccacgg gtaatgagag gtcactcact tgaactttgc cattccaggc attctcagag    3240
tggcgagggg ccacctgcaa gtggagcaca acttggtgct cttactgtgt ccttcagaaa    3300
gaataggtgt acagaaagga aatggcaatc ttatgtgtgc tgaacaaagt tttcaacaat    3360
tcctagttgt gccttttaaa ccatgcaata ttcaggatag tttgaatcaa gaagtaaga    3420 agctgctatt tgggtaactt atttctctgt gggaaggggc agggagagtc accaaacaat    3480
ctacctccaa ctctcttctc ttttgtctag agacattaca aagtgcactt gaggctgccc    3540
ccaacctctg acatttgttc ttgcatgtga tgatagaaag tcttcagatg gacttataca    3600
ttctgtgctt tggaagcaca agaagaacaa aatatgtgta tatttccttt aatgttata    3660 caaaagttta tatggagcag tattgttatg tttgtatgaa tttgcaaaaa ttaaagtgta    3720
caaagagatt ttgattttgc atatataaaa taaatcattt tattgatttt caaaaaaaaa    3780
aaaaaaaaaa aaaaaaaaa aaaaaaaaa aa                                   3812
```

<210> SEQ ID NO 2
<211> LENGTH: 861
<212> TYPE: PRT
<213> ORGANISM: Human

<400> SEQUENCE: 2

```
Met Pro Ile Leu Leu Phe Leu Ile Asp Thr Ser Ala Ser Met Asn Gln
 1               5                  10                  15

Arg Thr Asp Leu Gly Thr Ser Tyr Leu Asp Ile Ala Lys Gly Ala Val
            20                  25                  30

Glu Leu Phe Leu Lys Leu Arg Ala Arg Asp Pro Ala Ser Arg Gly Asp
        35                  40                  45

Arg Tyr Met Leu Val Thr Tyr Asp Glu Pro Pro Tyr Cys Ile Lys Ala
```

```
         50                  55                  60
Gly Trp Lys Glu Asn His Ala Thr Phe Met Ser Glu Leu Lys Asn Leu
 65                  70                  75                  80
Gln Ala Ser Gly Leu Thr Thr Leu Gly Gln Ala Leu Arg Ser Ser Phe
                 85                  90                  95
Asp Leu Leu Asn Leu Asn Arg Leu Ile Ser Gly Ile Asp Asn Tyr Gly
                100                 105                 110
Gln Gly Arg Asn Pro Phe Phe Leu Glu Pro Ser Ile Leu Ile Thr Ile
                115                 120                 125
Thr Asp Gly Asn Lys Leu Thr Ser Thr Ala Gly Val Gln Glu Glu Leu
130                 135                 140
His Leu Pro Leu Asn Ser Pro Leu Pro Gly Ser Glu Leu Thr Lys Glu
145                 150                 155                 160
Pro Phe Arg Trp Asp Gln Arg Leu Phe Ala Leu Val Leu Arg Leu Pro
                165                 170                 175
Gly Val Ala Ser Thr Glu Pro Glu Gln Leu Gly Ser Val Pro Thr Asp
                180                 185                 190
Glu Ser Ala Ile Thr Gln Met Cys Glu Val Thr Gly Gly Arg Ser Tyr
                195                 200                 205
Cys Val Arg Thr Gln Arg Met Leu Asn Gln Cys Leu Glu Ser Leu Val
                210                 215                 220
Gln Lys Val Gln Ser Gly Val Val Ile Asn Phe Glu Lys Thr Gly Pro
225                 230                 235                 240
Asp Pro Leu Pro Ile Gly Glu Asp Gly Leu Met Asp Ser Ser Arg Pro
                245                 250                 255
Ser Asn Ser Phe Ala Ala Gln Pro Trp His Ser Cys His Lys Leu Ile
                260                 265                 270
Tyr Val Arg Pro Asn Ser Lys Thr Gly Val Pro Val Gly His Trp Pro
                275                 280                 285
Ile Pro Glu Ser Phe Trp Pro Asp Gln Asn Leu Pro Ser Leu Pro Pro
                290                 295                 300
Arg Thr Ser His Pro Val Val Arg Phe Ser Cys Val Asp Cys Glu Pro
305                 310                 315                 320
Met Val Ile Asp Lys Leu Pro Phe Asp Lys Tyr Glu Leu Glu Pro Ser
                325                 330                 335
Pro Leu Thr Gln Tyr Ile Leu Glu Arg Lys Ser Pro His Thr Cys Trp
                340                 345                 350
Gln Val Phe Val Thr Ser Ser Gly Lys Tyr Asn Glu Leu Gly Tyr Pro
                355                 360                 365
Phe Gly Tyr Leu Lys Ala Ser Thr Thr Leu Thr Cys Val Asn Leu Phe
                370                 375                 380
Val Met Pro Tyr Asn Tyr Pro Val Leu Leu Pro Leu Leu Asp Asp Leu
385                 390                 395                 400
Phe Lys Val His Lys Leu Lys Pro Asn Leu Lys Trp Arg Gln Ala Phe
                405                 410                 415
Asp Ser Tyr Leu Lys Thr Leu Pro Pro Tyr Tyr Leu Leu Thr Lys Leu
                420                 425                 430
Glu Ser Glu Arg Ile Leu Ala Ser Val Gly Lys Lys Pro Pro Gln Glu
                435                 440                 445
Ile Gly Ile Lys Val Lys Asn His Ser Gly Gly Met Ser Leu Thr
                450                 455                 460
His Asn Lys Asn Phe Arg Lys Leu Leu Lys Glu Ile Thr Gly Glu Thr
465                 470                 475                 480
```

```
Ala Leu Arg Leu Thr Glu Leu Asn Thr Lys Glu Phe Ala Gly Phe Gln
            485                 490                 495

Ile Gly Leu Leu Asn Lys Asp Leu Lys Pro Gln Thr Tyr Arg Asn Ala
        500                 505                 510

Tyr Asp Ile Pro Arg Arg Gly Leu Leu Asp Gln Leu Thr Arg Met Arg
        515                 520                 525

Ser Asn Leu Leu Lys Thr His Lys Phe Ile Val Gly Gln Asp Glu Asp
        530                 535                 540

Ser Leu His Ser Val Pro Val Ala Gln Met Gly Asn Tyr Gln Glu Tyr
545                 550                 555                 560

Leu Lys Thr Leu Ala Ser Pro Leu Arg Glu Ile Asp Pro Asp Gln Pro
                565                 570                 575

Lys Arg Leu His Thr Phe Gly Asn Pro Phe Lys Gln Asp Lys Lys Gly
            580                 585                 590

Met Met Ile Asp Glu Ala Asp Glu Phe Val Ala Gly Pro Gln Asn Lys
            595                 600                 605

Val Lys Arg Pro Gly Glu Pro Asn Ser Pro Met Ser Ser Lys Arg Arg
        610                 615                 620

Arg Ser Met Ser Leu Leu Arg Lys Pro Gln Thr Pro Pro Thr Val
625                 630                 635                 640

Thr Asn His Val Gly Gly Lys Gly Pro Pro Ser Ala Ser Trp Phe Pro
                645                 650                 655

Ser Tyr Pro Asn Leu Ile Lys Pro Thr Leu Val His Thr Asp Ala Thr
                660                 665                 670

Ile Ile His Asp Gly His Glu Glu Lys Met Glu Asn Gly Gln Ile Thr
            675                 680                 685

Pro Asp Gly Phe Leu Ser Lys Ser Ala Pro Ser Glu Leu Ile Asn Met
        690                 695                 700

Thr Gly Asp Leu Met Pro Pro Asn Gln Val Asp Ser Leu Ser Asp Asp
705                 710                 715                 720

Phe Thr Ser Leu Ser Lys Asp Gly Leu Ile Gln Lys Pro Gly Ser Asn
                725                 730                 735

Ala Phe Val Gly Gly Ala Lys Asn Cys Ser Leu Ser Val Asp Asp Gln
            740                 745                 750

Lys Asp Pro Val Ala Ser Thr Leu Gly Ala Met Pro Asn Thr Leu Gln
        755                 760                 765

Ile Thr Pro Ala Met Ala Gln Gly Ile Asn Ala Asp Ile Lys His Gln
        770                 775                 780

Leu Met Lys Glu Val Arg Lys Phe Gly Arg Lys Tyr Glu Arg Ile Phe
785                 790                 795                 800

Ile Leu Leu Glu Glu Val Gln Gly Pro Leu Glu Met Lys Lys Gln Phe
                805                 810                 815

Val Glu Phe Thr Ile Lys Glu Ala Ala Arg Val Lys Arg Arg Val Leu
                820                 825                 830

Ile Gln Tyr Leu Glu Lys Val Leu Glu Lys Ile Asn Ser His His Leu
            835                 840                 845

His Asn Asn Ile Ser His Ile Asn Ser Arg Ser Ser Cys
    850                 855                 860

<210> SEQ ID NO 3
<211> LENGTH: 65042
<212> TYPE: DNA
<213> ORGANISM: Human
<220> FEATURE:
```

<221> NAME/KEY: misc_feature
<222> LOCATION: (1)...(65042)
<223> OTHER INFORMATION: n = A,T,C or G

<400> SEQUENCE: 3

| | | | | | |
|---|---|---|---|---|---|
| ccctagccca | tgtaggcatt | gcccttctac | actgacattt | gtatcggaat | ggaaatgggg | 60 |
| gcttctagta | tcttttttcat | ccttatttct | tcattaattc | cctactttcc | accagaatgg | 120 |
| cctgaaatgc | accatacata | gtactatctt | tggctgagtt | tttgttcata | tcattccttc | 180 |
| caacccagat | tccctctctt | ccctttttgt | gccttgttcg | tgaaatccta | tgaatttcta | 240 |
| gactggacca | ttgttttccat | agcactttt | aacttgcatc | cttgtttgtc | cctgattcat | 300 |
| atactgccat | atgacttctt | ttaaaatcgt | atttctctga | aatgttatt | gaatgtgcat | 360 |
| atataatata | tgaaacatat | acacagaaca | tacatatata | tatatatata | gagagagaga | 420 |
| gagagagaga | gtgtatataa | aatatataaa | atacttttt | gagatgttat | ctcattctgt | 480 |
| tgcccaggct | ggagtgcagt | ggtgtgatct | cagttcactg | caacctccgt | ctcctgggtt | 540 |
| gaagtgattc | tcctgcctca | gcctcccaag | tagctgggac | tacaggcgcc | tgctcccatg | 600 |
| cccggctaat | ttttgtattt | ttagtagaga | cgggggtttc | accatgttgg | ccaggctggt | 660 |
| ctcaaactcc | tgccctcaaa | tgatccaccc | aactcggcct | cccaaagtgc | tggaattaca | 720 |
| ggcatgagcc | actgcgcctg | gccaaaatat | ataaatatt | atgtatgtat | atgtcatcat | 780 |
| ctctcctcaa | tgaaactgca | aactcattga | agtcctggat | tccacattgt | caatagtaat | 840 |
| tgccaggaat | acacaagtcc | aatttttaaa | attgtgtcat | atgaagtagt | caatcaagtg | 900 |
| tggttggcca | cttactgagt | ctcttcacag | agccagacct | gagagtatcc | gtaattgtta | 960 |
| ccctaacctc | agggagctgc | attttcctct | actgaaaatt | gaatacaatg | ccatctgcca | 1020 |
| taattaattc | aaagattaaa | caaggctacc | gtgggtgcct | ggctcttcat | aggcactcaa | 1080 |
| taaatgtgag | ttgagagcct | gccctgtgg | tcccagctac | ttgagaggct | gagatgggag | 1140 |
| gatcgcttaa | gcccaggagc | tggacgctgc | aggcagctat | gatggggcca | ctgcactcca | 1200 |
| gcctgggcga | tcaagcgaga | tcctctttat | ttatttataa | aataaataa | ataaataaat | 1260 |
| atgtgagttg | aatcacaatc | taggtttgca | aacctccatg | tgtaaaggct | gcgcagaggg | 1320 |
| aacagtggtg | gaattatcac | aggcaggcca | atgtttcaaa | gagcttagtg | aaactgaaga | 1380 |
| agcttgtgca | tacaaaaggc | cagtttaggt | aactgtaact | gtgtttaagc | tttagtttcc | 1440 |
| tttctaagta | gatatatgtg | gaatgcaagg | ccagcaacca | actcacaaat | actgatcaag | 1500 |
| acggggagg | gatctaaagg | aatgtgagta | cgtcctgcca | ggaaagaagt | ttgctgcttc | 1560 |
| tgaaatattt | tcgtcttcgc | cactggcagg | attgatcgat | tgcagttagc | gaagaatttt | 1620 |
| ctgtgcaaac | tgtccaagca | tctgcttctg | tacttctgta | caactgttgc | tcaaattcac | 1680 |
| tcttcttttc | gaatcaccat | ctttgaagag | agacagaaaa | atccatttaa | accacccgaa | 1740 |
| ctaatcattc | gaactgcttc | caagtccttt | aaaggagaat | cctagcgagg | gtccgtaaca | 1800 |
| cttccccta | ccctctgcct | gggttcaaac | ttcaactccc | agggtcgcc | caagtccctc | 1860 |
| ccctagtcct | gtcatctaat | gaatatgcaa | ataccacata | attggcagcc | aatggcatgg | 1920 |
| gttctggtca | catggtgccg | atggtaggtg | agcagacaga | agttgtcagt | gaacagagac | 1980 |
| ggcgctcagt | ctgggcgag | cgctctagtg | agcgcggacg | gatgcttagg | cagtagtcct | 2040 |
| ggcagcggca | gtagtggtgg | cagcagaaga | gaggaagggg | gagggccccg | agggctacac | 2100 |
| acgctcacac | tttcaagttc | ccttggaggg | agaggaggtg | gggctgcaga | aagaggaggc | 2160 |
| caggagcggt | cccatccgtc | ccgtcccgtc | ccgtctcccc | ctcttcctct | tgctccttgc | 2220 |

-continued

```
cccccggctc tgcgagagtt gagggttcag gtggccgtac gcggcagtga gggcaagagg    2280
gccgggagag tggggagcgg aggcaggagt gcgggggaag atgcccatcc tgctgttcct    2340
catagacacg tccgcctcta tgaaccagcg cactgacctg ggcacctctt atttggacat    2400
tgccaaaggc gctgtggagt tattcttgaa ggtaaaggga ggggagggga gagatgggga    2460
gagctcccga gggatttcag ggtgtggatt gaggtgcttc tgtaacgttt gtatcgccct    2520 ccccctcct ttcctacgcg acccctccg tcatcccttg cccgcagct gcgcgcccgg      2580 gacccggcca gccgtggaga caggtacatg ctggtcacct acgacgaacc cccgtactgc    2640
atcaaggtaa aggggctacg ggtgggggga caggcgggaa gcgggagcaa gtcggcgggg    2700
gctgcttacc cccctgcccc cgcctaaggc ggtcctgcgt cgcccggcgg ggcgggcggc    2760 gaggggtgc gcagagggcg ggcggagtgg tgccgtcggc ggcttcggag tagctgtcgc     2820 gcctgggtc ggggagaggg gaccggggag gagcagcccc ggggagaaac cgcaggaggg     2880
ccgagctcgt ggcgcgacaa ccgcagccgc ctcggaacat ggcggacatt ttgcttttgt    2940
atgagcctgc gagagggaga ctgagggcgc tgctgagatg gaaggagggg agggaggga    3000 ggagcgggta aggagggccc gaaacccgga gggaggctgc gaggcgggcc cgccccttcg    3060
aggcgcaccg cgcgagggtg cggccgcggc cgggggggccg gacggagcct gcgactccgc   3120
cccgaggtcc tgccggccgg gcgcgcgggc tttcccggag cctgggctcc tcctctggcc    3180
cctccttcct ccccggtct tcctccccct ccttgggctc ttcgctgcat ctcctccttc     3240
tccccctctt cctcctggtc ccctcccctt cctgctgaga gcgtggcaga gccagccgcc   3300
ggccttcaaa gactagacaa ccgcctttgc actcgttggc ctctcaccac cccgcgcaa    3360 tcggaaatct gtccacgacg ccagtctccc cacccccaga cccggagaaa gtctttgcgt   3420
ttctgctccg gaattggcca ggttcagccc cgctctcagt taccttagct actgttactg    3480
tttcattgga aattccagcg aagcaacgac acggaggggg acgtgccaag tgcgaaccca    3540 cagggggcaga gcttttttagg gatccgctct acctatttac atcataaatt aggtttgtgc   3600
tagccacgta ggaattaatc cagggacaag aaagaaagga aggggaggac tcaaatgtga    3660
gcatttgtaa tagtcaagtt cgatgatttg attctgacct acaggagaaa gtagggagg    3720 acggtctctg tgggggaatt tatgttccta tggtgaggag ataaagaact gctgctttgc    3780
ctgcagtggc cagataaaat ggaatttaaa ctgttaaatc aacctgcata agagtcctgc    3840
ttgcatattg aaattttaaa aatactacca caatccttga cgtcttttgt taggctttt    3900 ctttttcct cagaataatc gtaatagtgc taggagacg cagtctggat gtgttgtgat     3960
ccgtttctgt agagtgaggt gttttaatga atggaaccta ccaagctgaa tagttggcca    4020
aagagtgttc cttcaagcat aaggaaacca aagagaaact aatttgtaa ctcgtagctt    4080 cggttaactg tttaattagt aggttcccct taaaactgtt cttttttcga taatttgttt   4140
tcagtttgtg attctatcca tttagaaaag tggaacaagt agacatcttt caaaatgccg    4200
taagcttttt aaaatgtca gttttcccaa aaggatgtga tcatttttttt ccacatagaa   4260 aaggagatgt ttatacatcc taggtctgaa tgtctacact cttcgactgc taatacagat    4320
aagaaccgac catttgtagt gtggccattt gaagacatgc tccttaattc gaagtagtaa   4380
aaaagataaa ccacaaagca gtgtgccttc ttttccttaa aggaacaact tattggccgg   4440
gtgcggtggc tcaggcctgt aatcctagca ctttgggagg tcgagatggg cggattgcct    4500
gagctcagga gtttgagacc agcctgggca acatggtgaa accccgtctt tactaaaata    4560
```

```
caaaaaaaca aaacaaaaaa aaaaacggcc ggatgtggtg gcgggcgcct gtaatcccag    4620
ctacgcggga gnnnnnnnnn nnnnnnnnnn nnnnnnnnnn nnnnnnnnnn nnnnnnnnnn    4680
nnnnnnnnnn nnnnnnnnnn nnnnnnnnnn nnnnnnnnnn nnnnnnnnnn nnnnnnnnnn    4740
nnnnnnnnnn nnnnnnnnnn nnnnnnnnnn nnnnnnnnnn nnnnnnnnnn nnnnnnnnnn    4800
nnnnnnnnnn nnnnnnnnnn nnnnnnnnnn nnnnnnnnnn nnnnnnnnnn nnnnnnnnnn    4860
nnnnnnnnnn nnnnnnnnnn nnnnnnnnnn nnnnnnnnnn nnnnnnnnnn nnnnnnnnnn    4920
nnnnnnnnnn nnnnnnnnnn nnnnnnnnnn nnnnnnnnnn nnnnnnnnnn nnnnnnnnnn    4980
nnnnnnnnnn nnnnnnnnnn nnnnnnnnnn nnnnnnnnnn nnnnnnnnnn nnnnnnnnnn    5040
nnnnnnnnnn nnnnnnnnnn nnnnnnnnnn nnnnnnnnnn nnnnnnnnnn nnnnnnnnnn    5100
nnnnnnnnnn nnnnnnnnnn nnnnnnnnnn nnnnnnnnnn nnnnnnnnnn nnnnnnnnnn    5160
nnnnnnnnnn nnnnnnnnnn nnnnnnnnnn nnnnnnnnnn nnnnnnnnnn nnnnnnnnnn    5220
nnnnnnnnnn nnnnnnnnnn nnnnnnnnnn nnnnnnnnnn nnnnnnnnnn nnnnnnnnnn    5280
nnnnnnnnnn nnnnnnnnnn nnnnnnnnnn nnnnnnnnnn nnnnnnnnnn nnnnnnnnnn    5340
nnnnnnnnnn nnnnnnnnnn nnnnnnnnnn nnnnnnnnnn nnnnnnnnnn nnnnnnnnnn    5400
nnnnnnnnnn nnnnnnnnnn nnnnnnnnnn nnnnnnnnnn nnnnnnnnnn nnnnnnnnnn    5460
nnnnnnnnnn nnnnnnnnnn nnnnnnnnnn nnnnnnnnnn nnnnnnnnnn nnnnnnnnnn    5520
nnnnnnnnnn nnnnnnnnnn nnnnnnnnnn nnnnnnnnnn nnnnnnnnnn nnnnnnnnnn    5580
nnnnnnnnnn nnnnnnnnnn nnnnnnnnnn nnnnnnnnnn nnnnnnnnnn nnnnnnnnnn    5640
nnnnnnnnnn nnnnnnnnnn nnnnnnnnnn nnnnnnnnnn nnnnnnnnnn nnnnnnnnnn    5700
nnnnnnnnnn nnnnnnnnnn nnnnnnnnnn nncttactat atagctgtgt gctcttttaa    5760
aattagtcat acctttact tgcagtcccg gtttgcatgg atagaattaa gtttgactta     5820
agtaccacat aaaaagcgta cgaaatgtaa gcatcatgtg ctacatctgt tatgttgctt    5880
tctagacaag ttttatgcat agtgttacaa gtgttgaccc cacctttata ccgtggtatc    5940
ttcagtgtac acagctagta tgaaccctg tttaacattt aaaaacgtct aatgtatcct     6000
tataaaacta gtatgtggtt tttaaaagtg ttaatgtttt gggattttt ggtataattg     6060 ttgtttttag tcttggctga ggttctgctg tcttgtatgt tttgttttgc tatgaatcat    6120
aatttccttt tatttagtga atagaagagg caggcttgtc actactatta ctttgaaaga    6180
aagtaagcca ttagagtagg gtatatatta acaaaggtat tcaaaatagt tttatgttgg    6240
aagctactta aaattatttc ttttttgttg aaggaaatta tcttttaaa cataaaatgg     6300 agttactttt ctagaaatag ttgaaacaca tgtataaaat actggccaga agattttat     6360 aaataggaaa tgataatgtt tcaaagaaat atcctaagtc tgtaatttga agacatacat    6420 ttgaaaagt aaaattttcc ctgagtgttg ccttttccca tcctgtagct agctttgctt     6480
actggtgtct gcatgccttt gacaacatgt atcagaaaat agcaaaattt tggcttacag    6540
atttaggaag taatttaagc ttttaaaatg atatgtgtta caggcatttt ttagaattt     6600 aactaagaca taacttttc atatgcccat gaatatattt tatagatctt atttgcaaaa    6660
ggagtgactt ttatgggagc ctttcattgt ggttaagaag ctatggaaga gcttatcagt    6720
gaaatagtag caacatggcc tgtgagagca atcttagaca atgaaagatg cttttaaaac    6780
tcaaaaagcc acacaggcag tgcattgact tttacaacga attgcctctc ccatgatctt    6840
gctttcttat ccaccttcct ttactggcca tttgtgcat gcagcaataa ttattttgaa     6900
ataagaaaag gagagagtca acagtagaag actagacctc tgggcaatac aatcttcaga    6960
```

```
ctaaggacca gctgtaagat gactagggaa gatgcctgac aaaactgtgg aggtctgtct    7020
gttctgtatc cccaacctct ctcgtatcca ttcattctta tttgctcctc gtttcaacct    7080
tcatcatttc tcacttgcaa gcagccactc agttgttctc cctacttcca gtcttgctct    7140
ccactgattc cttcccgtca ttgccctcag attgatcatt ctttaaataa aataaagtca    7200 ttccccctatg aaaaaaaaat ccttcagtgg cactccatta catttcccaa taaaagtaaa    7260
tttcttggcc tggcctccat ggccgttcat gatctggccc tatcttacca tgtctctgcg    7320
ccctctcttc tcttctcatg gacctcaggc ttcacccaca atgaaaaatt aggtcctcct    7380
ctccaaacac actatgccag ttgcttctgt gccattgtaa atgttattcc ctctgcctgg    7440
gacacattgg ttggccagac atacctcagt tctttattct atgttttcaa aagtcatttt    7500
gtccgtcggc ttttttccta ctccaagcag tataacaact tcctctgtga tcctttaaca    7560
tgttgtccac accttaacta tatagcattt agcatgttat atgggactta ttagtgttca    7620
tgttgacttc cctaatgtga gctcttgaag ggcaaatatt tgaacttcta ggtatttgta    7680
tccctagtac ctaaggggggt gtttagattt taatatgtac tcaacaaatg gaaaaaggtt    7740
tcaagcaata tgttaagtgt caaagctact catttccctc atgtcaaagc ttacctcatt    7800
cccggtactc ttccccatag agtaatcact attaacaatt tgatatattt aatgtttatt    7860
acagctagca ttttcatata ggttcaagtt tataatatgg tagaatctta ttgtattttt    7920
tacaagataa gtgtatatat ttctcttttt tcttttttat agaagtataa ttcatatata    7980
gaaaatacat gaatcctaat gacttgatgc attttttatat ttatacattc atgtaaccac    8040
catcccaggc caagatatat aacgttttcca tcaaccagga aaatgcctct tgcatctttc    8100
tgcaatccat ctctcccctg catgtaatta ccgttctgac ttttatcacc attgtagtga    8160
catgatcaaa atggtgtttc caaaagacaa gtgtaacagt gggttgacac tacggcagtc    8220
tcggcattca tttaccatat acttcttgaa catctcctct gcaccaggct ctgttatagg    8280
ggcctaaggt gaaaccagaa agatctggcc taagaaggga ccagaatagt aaaagacatg    8340
gtcctagtca ttaaaggtct tgaggatagt cactggaaaa agctgactag agaaggtggc    8400
ttaggatatg ggaaatgtaa agagcagtgg actcttaacc agagaattgg aggtgaggga    8460
ggaggatgca caggactctg agaatctggt gtgtctcaag actataacta gttaagactg    8520
gaccacagaa aggctttgaa acttgtaagc tagattttgt acatttcttc tgggatgcag    8580
agctcttagg tagaattgaa gagaaatagg acaaagcttg ttgtctatat gcttgtttgg    8640
ttataattac cttttaagtg agctaaaggg aggggagaat aaaaggctag ggagacccat    8700
aagttgtagt tgaaattgcc tagttttgtt gcttgctgct tgagagcttt tggccttatg    8760
gttgggattg gggtgggggt agggagatgg tgaagggcag ggcacaggta aggaaagggc    8820 agatatttt tcttttcagt ttgcctttgc tttgggaaga taattataat ttagaacaca    8880
gggttctcag tttcacagag tgaaaaaata tgatagtggt tccacatctc aggaagaaat    8940
gtgttttcta gagaagggta ggattgaagg accctcctta tgggagtgag aagggcagtg    9000
aagaaaggaa actacatgtt tcatttaagt tcttaaatga aaaagtcttt gtaaacatgg    9060
cctcctcccg gttgcctttt accgaaagag tgtaaatgag agaccaggc agtccctttg    9120 taactgtgta ttgggagctt ggaacacatt atctcctgga tacaatgttg gaagtggtga    9180
ttatgttccc agaccttccc tcccaggaac cttttttaacc cttcatgtca cttagccata    9240
gacctattgt gtttataatt gtttctaatg ggaaatgggt ttaagtttcc agcttgattt    9300
```

```
gttaaaaaca tattctttct ctcttcttcc tcacaactgg gtgtggactt tggttccatg   9360
agggtgggg acactgtaaa ggctccggca gagagggtga ggggctgagg tggcagtgga    9420
ggtaggcgtg gctcttcaca tatgccagtt actcctattc atagattggc tacatttaca   9480
cggttcagca tagcgtccac ttagccacgt atggttattg agcacttgaa aggtggctag   9540
tctgtcagtg ggtgcttcaa cagacagtgt aaaatataat attttggata tattaagtaa   9600
attattaatc taacttgttt cttttttactt tttcaatgtg gtgagttgaa aatttgaaat  9660
tccatatgtg aaatttgcac tatatttcta ttagcagtgt ttgtctatat tctttcttaa   9720
gatattttat gatgttcata tcctaggaat tgtttctgaa ggaggatcct ttctctggaa   9780
gttccgttta aaatgaacac cccccccccc ccgacccacc gcaataaaag actcatttgt   9840
gcatgaaagg ttatcataca gttcagagtt gatggcttga taaccccttgc ctgtggggca   9900
aaatatgaaa gcatcccatt cttatttgta ttgaaagcca gtttggttgc ttagtctttt   9960
ggatgcagtt ggtgatccaa ctggttgggt tagaagtctt ttcctgggct aagtataatg  10020
gaatatgtat gtgaatgaat gtaactgcag taattcagaa ttctgtttat aatatgtgct  10080
caccagtagt gctaaatgtt tcatactttc agtgttatta gaaatatgta acatgtccgt  10140
tgtttgattt acatagctac tttgcccaag aattctcagg agcagcattc tttaggaagt  10200
gtaggataaa ggagaaatac tctagttttgt catagtgtaa aacttaacaa aggggaattt  10260
gtatcactgc tgtttttgag agcttttcttg atgttcccca gcggagccct tgtcttatat  10320
catggcaagt catcagtggc gttaaaagga gggagaggcc acatgactgg agggctccta  10380
ggattcttac ttctgacagt cgttaacttt ctcaaaactt aatcctccta gtggaggtta  10440
caggagtgat taattgttat tttttggtaa ctataatggc tcccatttaa ggaataagca  10500
ccaatgtcta attctgaggc tgggtggatt tatagatatg ctgatgaata gcatctataa  10560
gaggtaggac cactttatag ccctaatttt ggatcctcct aaatcccatc ttatagtcga  10620
aggtgttatc tagcttgtat aactatccct gtatttcaga tatgatttga cttatatttg  10680
cttccttgta ataatgaaca atcacgaaat agccttcaaa aatagcagc tgacatttat   10740
tgagtaatgc ttaggtacag ggcaatgtgc taatgaatgt aaaatgttta tttagtttct  10800
cttcctagtc agtctgtgta ctggattact aggtactatt attatactct ttttatagat  10860
aagggaacca gggcccagag aggttaagta acccagccag tagtaaccta ggtctgtctc  10920
tattctagtc tattcagtga ttaaccactt cacttctcct atcaattgtg acagaaaatt  10980
cctttgata acttctcact ggtattttct cattatgatg catgtcctag agccatcatt  11040
ttttaaacat aattatcatg ctgttattta agctgctttt taatgtaata gtgcttggca  11100
ttgtagcaag cactcaatga atgaaaatta ttactgctag tgttattatt ctaatatttt  11160
ctctgactgt tgctgggtga gtattgtggt gcatatgttt gtaaaacact tttgcctttg  11220
atgtcccaca gttatgcccc tactggtgac agatatagag ttgttgagac tctcagttga  11280
tggagtatga aatagttgag gactggagga tgtgaactgg tggcctaggc tgaggaggcc  11340
ctataggaat agtggtaggt ttgtaaaagc agcagggtag tccttggcta tttattaata  11400
atagccacta aaaactgata tgccgtcttc actttaccaa tctcctgata aatgcttttc  11460
ttatgaggaa aagaaagata ttcagtgtac tccacagtag ccatttgttt tttctaatcc  11520
acagcctctg gaggagggtag acatggtttt taaaaacgtc tggaatacca tcatgccttt  11580
gcagagtttt gtgtatcagc ctgagcctta tctgctggtg tggtcttcat ttcaactact  11640
tctcccattt tcctcaagcc acacacctgt catagccaga tcattggttt tttcccctcc  11700
```

```
tgtgtagtta gatggcctgg ggtagaagag tggattttat agaagaagta gagatgtcag    11760
tcagtggggt cttaaccaga gaaacattgc atgaagactt ttgggtgatg tgccagatgt    11820
ttatagaaaa agtagaattc tatatcttaa accatttttcc cctggttata ctactcatta   11880
atgccagtcg ctcttttatt atctatatcc tgccctgtag ctcaaatagt tcagtgaact    11940
tagtaccagg agccaaacac aggatttgaa tgcaattgaa caaaagtctt gaaacatttt    12000
tgtttgtgca actgaaaaat agtactgtta agaaaactaa atatgattta ttaaggtctt    12060
aagatttact gtcgagctac ttgggcaaag ttactaatat tcatcctctt tgtccttgac    12120
tacatttgaa actaactact tcttccttcc agaaacttat cacttcctat attctgtttc    12180
tccactcctc tctctgataa ttctttctct atcttccaaa gtctttccct tggggagtgt    12240
atcctgcttc attcgtggtt ccaaatattc cgacacacac tgatgcttca ccatcttcag    12300
cttctcactc aggcatctca gctgagtgca ggacatctcc acacatctcc actgactgtc    12360
tgtcctgctg tcagctcaca gtcagacctc ttctgtcatt attcagcttt gttttttctt    12420
tttgccttcc atcttctctg gcttatctgc catcccttttg aaatttctct tacatgtgtt   12480
cctttgactc aatttctgtt gccatcactt taatctaggt cctcatgttt ttatgctttg    12540
accactgtac cagccttcta actggactcc caagtgcctc caaaattcct gtctccactt    12600
acatcaattg ctaactttcg aaaaagttg gttttatcat atcaccctcc ccaccagcct    12660
gccattctga gctctctagt atctgttcca cgtgtcggta aaacttatt tcccatcatt     12720 tcccacagaa gccctgcact gtctcttcta ccctctgagt gtatctcccc attcctgatg    12780 ccagcccctta gaacatcagt taaccaaagg aagaagagat acagagccag gagagctgaa   12840
ggcctggggg aggagaggaa gtaaactgaa atcattccat taagggtgtg acttgagggt    12900
gaggacatga cagaacatgc tttaaaatac tattataatg atgagaagtt gcagaaggaa    12960
ggagggtggg agctggagta tgacctttcg tgtttgatta gtctgaactc tagaccaaaa    13020
tggtttcatt taaattggcc tgaagttgcc tggaggcact gctgtttaat cagaagggcc    13080
agtccctctt tgaattttg tctctgccaa agacagccca cataactaga cagtggacaa     13140
taggattcca gggagaatat ctagccttta atatagccat ggcattggaa agtggagacc    13200
ccctcctgtt ttatttcttg aaggaggatg ttggcgatat gcagagcaaa gctctccact    13260
tttcttaata gcttacgtag gtgcgtaaac attgtaaact ccctttcata gtgatgcctt    13320
tgagttgtgt gttagaagta gattttaggct ataagctaggt actttttataa aatcagattt   13380 taaaaagtgg acatagtaca tccagtctag tagatcatac catctactgt catgtaaatat   13440 ggcaaactgt atcattgtca cttcagtagc tctgtcaaaa gtgctggact ggaaggcaag    13500
agatccatgt tcttaacctg agtctgttac taattacaca catgacccca ggcaagtcac    13560 ttaaccttttt atggtgtcag tttcctcatc tgttaaatga agggattaga ctagattatt   13620
tccaggactc cttccgaaaa agtacaggag agagttgtat aactgaaagg cagaaagtgg    13680
aataattgag gcttggaatt cagggtgact taaaaattac tttaggctgg acatggtggc    13740
tcacacctgt aatcccagca ctttgggagg ctgaggtggg aggaccactt gagcccagga    13800
gtttgagaca gcctaggaaa cacggcaaga ccttgtctct acaaaaaata attaaaaaaa    13860
aattagcctg gcatagtggc acatgcctgc agtcccagct tctcaggagg ctgaggtggg    13920
aagatcactt gagcccagga ttacaagact gaagttagct atgttcacac cactgcagtc    13980
cagcctgtgc cacaaagtga gatcctgtct caaaaacaaa aacaaaaaca aaaacaaaaa    14040
```

```
aacaactttt aaattttaga aaacaggtcc tggatgtgtt taatgtgcta tatcacacac    14100
ttagtggtta cattggtaaa tgccactcca tcttattgat gtcaattctg tttgctgtaa    14160
acaatttaat aacgttcatg acagagtcct atcaatactt tggaagagtg agagtgaggg    14220
tttggtgaac agacagacta actttgtatt ttgttgggat ttttaacaat gaatgcatgt    14280
tacttttacc acgtaaaaag tagctcataa caattttttt gaaattattt attttcatta    14340
acttttattt taagttctag tgtacatgtg caaaatgtgc aggtttgtta acatgtgcca    14400
tggtggtttg ctgcatagat catcccatta cctatgtgtt aagcccagca tccattagct    14460
attcttcctg atgctctccc ttcccccacc cccattcaca ggccccaccc agtgtgtgtg    14520
gttcccccca tgtgcccatg tgttctcatg aagaatttt  tcctaaaaga attagtcctg    14580
gggaaagagg tgctgtgtaa tcttcagaac gtaataaatg gccattctgc tatctcatat    14640
gttcaacact ttctgcaatg cttaggtggc ttagtctcac tcctgtccat gtatgttttt    14700
tccaaggcca aaaatttta ttattttgtg tatctgtcca taaatgagcc aaaatgtaac    14760
taactgaatg tgtgatatgc acaatagcag ttttttttcc tgataatagg tattagttga    14820
tagctgcagt tgaaatagtc tgagactggg aaggaaact  tttcacattt aagtatgacc    14880
aagtttagta agttctaaga tgtttctgct tcagtagcag tgcaattgac ttttggaggg    14940
aggagaaaag cttctaaaat tattggtttc tacgtgttac tgtccactgg tgaaggtcag    15000
atttctttgg atattatcat gttttccagt aaactttgag aagtgtgctg cttcacaatt    15060
ttatcctaat tccctggggt aataattgaa aacttcataa acatatttt  aaaatttct    15120 agatccttat gattgtttat atgcttaaaa aacttcatac tagatattaa tttaaagagg    15180
tcagtaaaac aaaatggtga actatgtgtc agtggaatca aactgtgaat catttctttg    15240
cccagtttcg ttaaaatatg tgatcatgtg agtctttaac tgtctgctga agatcagtgc    15300
agcaggccac agactgttaa atacatttct gcaatatatc gggggaggtc aatttcttaa    15360
tatctttgtt aaaagtaga agacgcaagt aaactagatt tcatacatgt agtcttggtt    15420
ggtagtatct cctgaagcat gtggaggaaa attggtagat cgaaacagaa tgatagcatt    15480
cagagttctc agggagagaa ccgatttaat caaataaaat gggctttgca catttcggca    15540
agttcaagac actaagaaaa gcccttgggg aagtaacttt tataaaactg aatccaagag    15600
aactggtttt tcttttcttt tttttttttt tttttaaaat agagtcttgc tctgacaccc    15660
aggctagggt gtagtggcgt tatcgtagct cactgtagcc ttgaactcct gggttcaagc    15720
gattaccact tgggctaca  aacacatgcc actatggttg gctaatttgt atgttaattt    15780
tttgtagaga gaggagtctc gctgtgttgc ccaggctgat cttgaactcg tgggctccag    15840
tgatcctctc tcctcagcct cccaaagtgt tgggattaca ggtgtgagcc actgcaccca    15900
gcctggctat cctttaaaaa gtaattttaa agctacacta tacatttaaa acacagaaca    15960
ctaaaatacc tcctttgagc gttgaagtat attagtacct tgagtaaagt gagaaaagca    16020
caaaaaaagt gaaatctggc caaattgttg gagtatcagg gaaaagttg  tgtcagggtc    16080 agaaaatata agcaagaagg aagttttag  gggaggtaca agaaggaaga cagttccatt    16140
cttataatga tataatgtat tcttagtgtg tactttataa ttgtaacaac ctcctttata    16200
ggtgtgctag ctgtaaaaat cattttacaa agatatttca acagtttaag gtgattcagc    16260
tgtcacagtg ttctgttacc taagagagca agtaaacctt gtctttgtta tcagaattgg    16320
agtccatttt aattgtgaga agaaaattcc tgaagttgag aagttttaac ttgcccaaat    16380
attcagggca aagaccaaga gaaagtcat  ttgtctcctc gggagacaga gatgattgga    16440
```

```
aaagcagggc ttcttatttt tcatgtcatt ccatctcact ggtgagttta ccaatgcagg    16500
aacagtttgt gatgacagag atgacagaat gctaagttga agaagaaagt gagttggttg    16560
aaaaatactg ttggaattga tttatgcaaa ttttctgggt tgtttcagag caagttttcc    16620
ccaaacttat ggagagcaga tggaaaaagg aaaatagttt atctttcaac aagagaaatg    16680
atggccctgc taaatttaga ctctggcttt aacttgtgac atctgggaaa atactcaaat    16740
ctgttaatca tttagtttgt ataaccacct agaagagccc aatgtccagg atagacctct    16800
aacatgggct tacaaatggc agatattacc aggctgattt aatttccttt aataaaagat    16860
aaaaagtctt gtcaaggaga ggaaagcaac atgcattggc tttctggatg tcaacaaggt    16920
tttccttcat tcattgtgaa gagcttgcta caaagctagg aagatttgga ctggactgca    16980
ctgctcctca ggggaatgtc cagataggct gcaggatgta tgtgcctaaa acaggtcagt    17040
gcagtggctc agcaccaagt caggggggaca ccacaaatgg agcctcccag caagaagttt    17100
tgtcactgct gtgtgaagga gcctggcttg tgaaaattca taacgtacaa ggattctttt    17160
tactgtttgg aaagattcat tgccagtccc tttaaatagc taccaccta gagaatatta     17220 atcattcaac tatttttttt tatttataaa tagtcaattc acatacagtt tgtaagggtt    17280
acttttcttg tggaaagtta ggtacagctg ccctaaatat ctttatcggt taccttggct    17340
ggggaaatta acagcatgtt tattaaactt gtacattata ctgtgttata acattatacc    17400
attttccaaa tattagtaag gtcgctaaca ttttggaaaa ggattacaag tgacctttag    17460
agatagaaca ggagtttttc agaaagggcc tctaacacca ctcccacatc cccttcgagg    17520
acagttgatc tgcttttatc tcttttactt gttcttagtt cctggcaaga tttcaatgga    17580
ggaaaaggct tctctattta aaaaaaataa aaatcaatga aaattaatga atcggagaaa    17640
tggcctggct aaaatgggat gaagttcagt attaggatac tgagggatac tgaagtttag    17700
gggagccact aaataacact ccttcatttc cctcctccac ttgaaatcta ttgagaggta    17760
agacacagaa gccagccaga gttccaaatt acagctttat tcctgatcaa agctggagga    17820
aaggatgtag cctacatgtg tgttctgaaa agcttccaag tagttcacat attgacagac    17880
ctaccctatg ggtctgttgt aggggtggaa cctaccccct tagcaccaca tgtcagagaa    17940
cataccagaa tattcaaaag agcttcagca acaggcctgc agagagcatg ccagtttcct    18000
gtttgcaaac caaccagtca gatgagaagg tggaaatgtg ggtgcagagg gtaatagaaa    18060
atattgcttt taggctttgc ccttctgagg agaaaagtgc aaattctctc cttcctgtgg    18120
tgatgtaagt ggagaataaa tagctagtgg ctagtcagat caagctggga caagaaccca    18180
ggtcactgat agaaaggccc atgttttttct gttggtatga aaagacattt ttagttgact    18240
atggaaactt aaacccgatc tgaattaaca tattgaatta acatttattg agacaggagg    18300
tgttctcttt ctgtaagtca gatttacatg aaggattgtt acagggtgta gaattataag    18360
atacataagt ctgatttata ttaaaggaac gtatagaatt ataggatata aaaactgcaa    18420
gggaccttag agttggtttt tcagcccttt cattccttgg gtgaggaaac agccacagtg    18480
ggattaagtg acttactcta gaccacttgc caagcgagtt agtgacagct aggaatagac    18540
taggcccttc taattcttaa ttcactgttc cccacaccta attgttctgt acttagatgt    18600
cagggaaagt aggcttaaat taaaatgaaa tttgaaaaat ttattaaact tataaactaa    18660
tctaacaaga catatttgtg aagtgaatat aggcttacca tgaagatagt gcaggttcaa    18720
ttcccagacc accacaatga agtgagtcac aagaattttt tgctttccca attcatggaa    18780
```

```
aaattatgtt tacactatac tgtagtctat taagtgtgca atagcattat gtctaaaaaa   18840
caatgtatac accttaattt aaaatacttt gttgctaaaa aaatgttagt gatcaactga   18900
gctttcagcc agtcataatc tttttgctgg tggacagtct tgccttgatg ttgatggctg   18960
ctgagtgatc aggcagttg ttgctgaagg atggggtgg ctgtggnnnn nnnnnnnnnn     19020
nnnnnnnnnn nnnnnnnnnn nnnnnnnnnn nnnnnnnnnn nnnnnnnnnn nnnnnnnnnn   19080
nnnnnnnnnn nnnnnnnnnn nnnnnnnnnn nnnnnnnnnn nnnnnnnnnn nnnnnnnnnn   19140
nnnnnnnnnn nnnnnnnnnn nnnnnnnnnn nnnnnnnnnn nnnnnnnnnn nnnnnnnnnn   19200
nnnnnnnnnn nnnnnnnnnn nnnnnnnnnn nnnnnnnnnn nnnnnnnnnn nnnnnnnnnn   19260
nnnnnnnnnn nnnnnnnnnn nnnnnnnnnn nnnnnnnnnn nnnnnnnnnn nnnntcataa   19320
gaaacaactc attcattaaa gttttattat gagattgaag caattcagtc acatccttag   19380
cttcacttct aaatctagtt ctcatgctct ttctaccact tatgcagtta cttcctccac   19440
tggagttttg aaccccttaa agtcatccat gaaggttgga atcaccttct tccaaactcc   19500
tgctaatgtt gatattttga cctcctccca tgaatcacga atgttcttaa tgtcgtctag   19560
aatgttgaat cattcccaga aggttttcaa cttttcccag acgcatcaca ggaatcacta   19620
tctatggcag ctatagccct acaaaatgta cttcttaata gccttacaaa atgtattttt   19680
taaataataa gacttgaaag tcaaaatgac tccttcaccc acgggctgca gaatggatgt   19740
tgtgttagca ggcatgacaa caacattgat ctccttgtac atctacatca gggctcttgg   19800
gtggccaggt gcattgtcga tgatcaatag tattttgaaa tgaatctttt ttcctgagca   19860
ttaggtctca aaagaggggc ttaaaatatt cggtaaacca tgctgtaaac agatgtgctg   19920
tcatccaggt tttgttgttc cattgctaaa gcacaggcag agtagatgta gcataattct   19980
taagggccct tggattttca ggatggcaaa tgaatgttgg cttcagctta aagtcgccag   20040
ctgcattagc ctctaacaaa aagtcagcct gtcctttgag gctttgaagt caggcattga   20100
cttctccttt caaattatga aagtcctaga ttgcatcttc ttcctataga agtccgcttc   20160
atctacattg aaaatctgtt gtttagtgta gccaatctca tcagtgatct tagctagatc   20220
ttctggataa cttgctacag cttctatatc agcacctgct gcttcacctt gcacttttat   20280
gacatggaag tggctgcttc ttctagcttc aaagttttct tctgcagctt cctcacctct   20340
ctcagccttc atagagttga agattcattc catcaactct aggaagagtt agggccttgc   20400
tctggattag gctttggttt aagggaatgt tgtagctgat ttgatcttct atccagacca   20460
ctaagtcttt ctccatctcg gcaatgtggc tgttttcctt cttactcctg tgttttcctg   20520
aagtagcatt ttaaatttc ttcaagagct ttccttgta ttcacaacgt ggctaactgg    20580
tgcaagaggc ctagctatct cagctttcga catgccttcc tcactaagtt taatcatttc   20640
tagcttttga tttaaagcga gagaagtgca actgttcctt tcacttgaac gcttaagagt   20700
ccattgtagg gtcactaatt ggcctgattt caatattgtt gtgtctcaag gaatagggag   20760
gcctgaggag agggagagag ataggaaca gctggtcgat ggagcagtta ggacacatac    20820
aacatttatc gattaagttc actgccctct tatgtgggta tggttcatgg tgccccaaaa   20880
taattacaat agtaacatca aagctcactg atcatagatc accataaaag atataataat   20940
aatgaaaaag ttagaaatat tgcaaaaatt accaaaatgt aacagagaaa cacaaagtga   21000
gcacatgctg ttgaaaaat ggcactgata atacagggct gccacaaaca ttcaatttgt    21060
aaaaaatgca atatctgtgt ggtgcaataa agcaaagcac cataaaatga ggaatgccaa   21120
tatacataat gtgtggaaga gtggtttaaa ttggtgggct ctgaagttag gctatctgga   21180
```

-continued

```
ttcaaatctt ggctgtgcca tttcctagtt gtctggcctg acaagttac  ctcgctttcc  21240
caagcctcag tatcctcatg tataaagtga agatagtaac agcacctacc cagagggtgg  21300
ttgtgaggtt catgtaagaa ggatgtatat tacatgctat gcttagtata agtgagttcc  21360
taacatataa gcactgataa atattagcta tcattagtca tcatcatgat tattttacct  21420
tggagagact taaaatttga cctgtgaaga taataaaccc ttagcttagg attctaccca  21480
tcctaagtta ctcctttgtc ctaaacctcc attcttagg  cctcttgtaa tatcttttac  21540
tgtctatcct ttggcctcat gctctatcac caagtctgtc ctatttgttt cacatgtttc  21600
tcatttaact ctttcatctg catttccatc ctaattcagg tcttgattcc ccaggtgtgg  21660
cttactattc aagcctccta gctgctcctc ctcctcctcc tcctcctcct cttcctcccc  21720
ctcctcctcc cacccccttt ttttttgagac agggcctggt tctgtcaccc aggctggagt  21780
gcagtggcat gatggagtgc agtggcatga tcatggcaca ctgcggcctc cacctcctgg  21840
gctcaagtga tcttcccgcc tcagccttct gagtagctgg gaccacaggt gcacatcacc  21900
atacccggct attttgtgt gtgtgtattt ttggtagaga cagggtcttg ccatgttgcc  21960
taggctggtc tcgaactcct gagctcaagc aatgtgccgg ccttggcctc ccaaagtgtt  22020
gggattacag gtgtgagcca tcgcgcctgg cctcaaacct cctagcttct tctgactaca  22080
gcttcacttt cctgcaggct gtcctgtatg tcactatcag actgattttc ctgtttaccc  22140
ctgccttgga ttctgtagtg tgtctactgt ctgctgcttt aaggccaggc tctcatacct  22200
gaccttcagg tcttttagga acgtcagtgt ccaatagaaa tataatgtca gtcatacaca  22260
taatttaaaa atttctacta gccacattaa aaagtaaaaa caggtaaaat taattttact  22320
aaaatatttt atgtaaccaa aaatatccaa gacattatca tttcaacatg taatcaatac  22380
aaaaataatg agatttttggc attttttgtt ctgcatcctc aaaatgccaa atgcattcta  22440
tacttacatc acatctcgat ccaaactagc cacacatcaa gtgttaaata accacatgta  22500
gataaaagcc actgtatcag atagtgcagc tgtagaatgt gacttgccac cacataaaca  22560
agacataact atgtttcact tcttccttgt ttgttaaaat agggatgtta atgccatgcc  22620
tatttatag ggttgtccta agccaatgtg aagtgtgaaa gtgctttgta agcagtaaag  22680
ttctgtaaga atgtatggaa gttattatca ggagtgaagg ttttactaa cataagaata  22740
caatatcttt ggagtaaagt aatttaaaag aaaaacccat attaaggagg caaattagct  22800
gtcctgaatt catttgtgaa aaaattaac  tctaagcaat gaatggagag tgtaaatgta  22860
tactcactat ctcttatata ttatcttttt ggtagaaatt tatcacatta ataagattct  22920
ctaaatactt caataaatct gtgggccttt tttccttcag catgttgagc aatggacata  22980
gggacatttg gttcttctct tgatataggg agctggaccc ctaccaaaga gttcattgct  23040
cttggtagta aatgtagcct acatactttg tagtactgag gtaggagtgg cattaaaatt  23100
tcccatatca tccaattcat tgcaagaaat aggaattaac ctacaaacaa tgtcagagat  23160
ttagatacag aaactattaa tatttgggcc gggcgcagtg gctcacacct gtaatcacag  23220
cactttagga ggccaaggca ggcagatcac ctgagctcag gagttcaaga ctgccctggg  23280
caacatggtg aaaccctgaa tatactaaaa tataaaaaat tagccaggca tggtggcaca  23340
cgcctgtagt cccagctact caggaggctg aggcacaaga atcgcttgaa cctgggaggt  23400
ggaggttgca gtgagccgag atcgtgccac tgcaccccag cttgggctac agagtgagac  23460
tccatctcaa aaaaaggaa agaaaagaa  aagagagag  agagaaggag agaagggagg  23520
```

-continued

```
gagggaagg aaggaaggaa ggaaggaaac tattaatatt tgtaaaatgc tttcatttca    23580
tattctgtat tctgacagat tggtgaatag caccactaac gataaggaca cattatttta    23640
aataaagatg agtcataaag tggtacccaa atcttatcct agcccttac caaaccaaat     23700 agtccactaa ttttaaaaa ttataccttg aactaccaca tggcccttca ggtgttcaaa     23760
tttaatatat aacctttgtt accagtgtgg aaataagatt gctaaacgaa gtgactccaa    23820
aaacaagaat caattttata taatggcttc agggtaaagg accccgccc accatttaca    23880 agtttgccaa agccagaaac ttcaacataa tgcatgacct tttctttctc acctgtccct    23940
ctaattagct actaaatcct taggactcct cctctgaaat acttccttaa tctgcaacct    24000
cctctccatc cccactgccc taactcagcc tttcatcact tttctcgtaa gctctttcag    24060
cagtctccaa accagtttcc ctgcctcaag cttcagcctc ccctccaccc cacaatttat    24120
tctccaacta ccagcagaga tcttagtaaa ataaagatct gatcatacca ctccccggat    24180
ttaaaacctt gagttcttcc cagggccagc agataaaatc caaactgctg agcatggtgt    24240
acaaagcact ttatagtcag agcccaaatt atcttaatca gccttgcctc ctgccatgtg    24300
cccagagcaa tgataatcag attactggtg gttctcaagt aagtcctatc cttttatctg    24360
ttctcttccc ttgcacagtc ccctccaccc ctcacatcag tgagtctcat gatcttcact    24420
ccatcccatc agtatttctc aaatgtccca cttttcagtg agaagccttc cctcactctc    24480
tggtcacttg ttctttcagt ctccataagt gcatctctta ttcctttgtg gcaggaaccc    24540
ctcaagagct aattcctctc tatatcccca gcacgtagca ttctgccaag tatagcatag    24600
tttgtcagta aaaatctgt tgaataaata catgaaaaaa ttgatcctct ccacccaaat     24660 gtacacctt ctcttctacc ccaaagaaga aatctaattt cctaattcag tgtgatttat      24720
aatcaactac tgatagttcc aggtatttga aaagatactt taaatcataa tgcttccttt     24780
tcactaaagt tcagtttatc tagtccaata agattttcct tgggccataa agagttattc     24840
tcattcccta tatttccagt actaaaagtc atatatacaa tttggccaaa ggagcacctg    24900
gaaagtttta acctttaaat gcttcgacct ataggatatg ttaggaacat taaaataaaa    24960
gacaacaaac taagcacatc tttaatttca caagaattgc cagctattgg acctggagtg    25020
aatcttaacc aagatcacct tcaccttgaa gggttatgca ggttgtgttc tgtttaaccc    25080
tagggggcgc cactctcaca gattatgatg tgaatgactg caaggtggta tcattctcag    25140
ccttatacag tgtccctgct tatcagatca tcctcctttt cagcttaggt cctaagaagc    25200
caactggttt gctcaaggtc acacaggtat ttcataacag ggttcatagc caataaccctg    25260 ccccttct tacttcccag tcattctact aatccaaatt gctctggaag accatgaaac      25320
cagaaaagag tgtttgatgt agttgcatgg ataatggact atatgccttc agctaaatgt    25380
gaaattcaaa tggtttggtt tatctcggta tcatttgctc ttgttttcca cctctagctg    25440
tactggcctg gttggcataa cttcagcatt tagcatatca cactgctgct tcaggctca    25500 ccgagactca agtggctgtt ccactctgtt gccacgctgt gctgtcttct ctctttcttg    25560
ctggcccatt cctctgtgac ttcctgttag ctgccacctt cttcttttag cttctcttct    25620
cagcactttt tgctgctttg tttttatacc catctcagac cagtcagcac gatcctttcc    25680
ttccttctat tctacaaacc aatcaatcac agcatgttgg ctgttgacct tggatctttg    25740
gttgtttgct gctgttcata gctgctgggc gtggctaggg gatgctgctt cttttgccaaa    25800 acttttgtt tcttttcttt tctccctta ttctagatct tgggctttct gaatgcttga       25860
agataccaga agggttatat ccaaataagt gtggctctat tcctattact ccctctttac    25920
```

-continued

```
tcttgcttaa aagtgaaaat attgcttcgg tggaagaatc ttggttagaa gaattaatgt   25980
agctcagaca gtcaatatag ctaattgtct ttaccaagga caatgcattt aaaaaataac   26040
tactccttcc tctgcccctt actcccatgc tcaccatcaa tgtgaagcta gggtaacagg   26100
tgtgttggca ggtttggttg agcctgaaca gaaaactgga cctcttgagc cacagtcctt   26160
cagccataat ggacgaagta ttttttgctt cagttctttg cgcttgatca ttagagctag   26220
caggtctttc cgaaactgct tgctttagtt ctacctgatc agtgaagata tagaatagaa   26280
ttaggttaaa gagtggttaa tttcttagag ttttgatact tgctgtttag tgattgtact   26340
ttatatattg ttcattgtat aatcaagaaa ttctttgtaa atgtttggtt gcaggctgg   26400 ttggaaggaa aatcatgcaa cattcatgag cgaactaaaa aatcttcagg cttctggact   26460
gactactctc ggtcaggctc taagatcctc atttgatttg ttaaatctca atagattaat   26520
atctggaata gacaattatg gacaggtaaa ataatttga gtgagtacag ctaatttatt   26580
ttggtggctt ggggtaagaa tttaaaattg ggcatgatta ctaagttttc tgctactttt   26640
cataacctcc aaaatgaga ttcttattac cttttaaata tatacttttt aaaaatccct   26700
cttcttttgg ttcttgtata tggcttgata atagaatagc taaaattgtc taccatgaga   26760
taatcagatg tttgagaatg atgtgaataa acggctgaga aatatcggaa caagacaatt   26820
ggaaagaaac tttcagtgtc cttaactcct ctgcccctcc caatttgatg aaaaagctct   26880
aggataagaa ggcagagtag catttgctgt tgctcccatt gtcctttcct cctctaaagt   26940
ctgtgctcac agtaaccaga gtcactctcc aggttgcagc acgcaagtca ctagtgtcct   27000
atctgtgcca ggattttgac ttaagtgaat ggattcatga gagtggatga taatgccagt   27060
aatcttgtaa tattattttg tgattacttg gaaagcagag tgagagaggt atttgaatgt   27120
taatggtttg gggagttcct gaattataag aattcctcag tttatactga atgttacctc   27180 ttcagggtt gttattttta ttcctaccca tttcgttccc tggtcatttc ttccttattt   27240
atccagacaa attttatcat attcttgaga gatcattggc aaggcaaata taaaaattta   27300
aatatacttt tattacttta catggctcta atgcttttta aatgtatttt aggggagaaa   27360 tccattttt ttagaaccat ctattttaat taccatcaca gatggaaaca agttaacaag   27420
tactgctggt gttcaagaag aggtgagatt ttattttttt tttaattttg tttaaatggc   27480
agggaacatg cagctatttc tgtgggaggc atttccagtt aacagtaagt ttggtcaaat   27540
catccatctt ggtaatcctt gaaagactgc ttaattttat tgagttacat gaaagaaaaa   27600 gtcaacccctt taattctttc ttcatttta tatggtttgt tatgatgaac cttttcacat   27660
ttttgcctta tcagctccat cttccttga attcccctct gcctggaagt gaactaacca   27720
aagaaccttt tcgttgggat caaggttat ttgccctggt gttgcgtttg cctggagtgg   27780
cttctacccg aaccagagca actagggagc gtaccaactg atgaatctgc catcacacag   27840
aatgtgtgaa gtcacaggag gtattggcaa tatttaatgt ttctgaagga aaaattcaga   27900
gcatagagta tattttttcat taaatgccat atccagtctt tacttgtttt ccttcaaagc   27960
cttttaactc tgttgcttaa ggtcatcatt ggtatatttg ctgccaatgt agttatgatt   28020
atttcaagtt atattttagg attttaaaat gcttatatta tgaaattata tttgatcaaa   28080
cttgtgctat ttattttcc ttctgggata ggtcgctcct actgtgtgag aacacaaaga   28140
atgttgaatc aatgtttaga atctctagtt caaaagttc agagtggtgt agttattaat   28200
tttgaaaaaa caggaccaga tccacttcct attggagaag gtatagtaga taacttttt   28260
```

```
aaccctaaag tgttatatag gagaatgaga agacattaaa taaattacta tagacacagt    28320
cttcactatc cacgtgcatt tgagtggtta caaacataca tccaaacaac taccacacat    28380
tcactgccta tgtatatgta tcaggtggcc aaattctaac aactttaatt tcatgttgaa    28440
tgttcctaag aacgtgtttc cttttcctgg tgcattttat attccctggt cccagtcttt    28500
ggatggcact gactcattca cctctctatt cacaaaatgt ctggagattc actatggtgt    28560
acacttaaat aataatcttg ttttggtttt gtgagtgcca aatatgctaa gccatcttta    28620
cgaaatatgt gttagtttct gcacctcagc aagaaattat gaatgtttat ccaggaactg    28680
ctcatcttct ctaagatcct acactagtat tttcccggtc acttttcac tctgaagtta     28740 agagttgagc aacctttttct ccaaatgaga tttcacagaa agttcgacat ccaaaacttg   28800
atgaaagtag ggtgacttttt gcataggga agttaaatcg tagtgaatct ctagatggtt    28860
tgtgaatgga tgtttgtaat cacttgaatg caaatgaatt tcaaagggat cagggaacta    28920
aacaagcacc atggcaacgc attgcaagac ttccatggta atgcactgca agaacagagc    28980
tcctagaaag tctatgtgta tatgtatgta aatttgtaag tgtatatata tatatatata    29040
cacacacaca ctccattatt attaccacag tgattgtcta gcctgattta tatgttttaa    29100
ttgccttgac gaagaacaaa ggggtcaaat gcataagggc agaaagctac acatttctgt    29160
ctgaagcagt ggatcctgtg gctcctgatc tttttgttgtt gttgttattg ttgttgtttt    29220
gctctttagt tccccatcct tttgagaagc tgttggaaaa aatatagacc cctttttccct   29280 ataaatacag acataagtga cacatttcac aattttgtat ataatctcag gggttttttg    29340
ggcctccaag ttaagaacat cttgccataa aagactgagg gccccacagc ctattttaaa    29400
ttaactgtgt aggaaggcca tgttatactg ctagcaatcc aaaatttcgt gctcactatc    29460
ttagcataaa ctgggaactt acatattgaa attctagtag gatttggtgt catgtaaatg    29520
gcacagattt ttttctagc tccagttctc ctttgtccag agttcttaac ctttcaggtt     29580
ctgatgaaag ttaagaaccc ttttcctcag aaaaatgcac attgtcagaa ttgtgagctc    29640
aactttgggg ggatcctcca aagccattac acttttttttc cctactgcac agtggaccca   29700
ttaaatctcc tagtctaaag aaattacttg tttaaagtaa tgcttaaata agttattcaa    29760
atgactgata atttaagaaa aatgagactc aaatcattaa agcatatctt ttacaaatat    29820
tatcattaaa agtttatata actctgcctt gccctgattt gaggcggggg gagaaggagg    29880
aaggaaatga aatatgctag tttaaatcat taaaatgcat tcaggataca ttattcagca    29940
ttatacaaca cccattgtcc atggaatttt gatggtggat ggagaaacca tagtgaatta    30000
gtccacgata aacttgatgt gtttgctttg tgctcccctc aactatatac acattgtctg    30060
catttcttct atctttaagt gaatttggct agttttttatt ttgcctttgt ggtcattggg    30120
tctaattgtt tggcaaagaa cacttttttc ttgtatttgg aaatagaaag aatatataaa    30180
tggaatttat gatctatttt tgtcagactc cagaaatgta aaaactatac cagggagtga    30240
acaatttcat ttgcctaatt tagtaattga attcttgaaa aataactgta gtgttttgat    30300
gtttttaatt tatgtgtacg agtctcagaa aatttaaaac tagttttacc atagttttct    30360
gcataactgc atattctctt actaggttaa gaatggtggg gtgggtgttg ggttagaaga    30420
gatggattag acgaaaagag ttgctagaga gaacatttag aaatcctagt agagtcactt    30480 tttttttcttc ttccattttt catgaatcat tgttcttgtt ttattttgga ctttgctttc   30540
agctggaaaa tttgtacaag aagatcagca gctgtaaaaa gaaactcacg ccttagtttg    30600
tcttttgttt aacttttaga tggacttatg gattcatcca ggccaagcaa ttcatttgct    30660
```

-continued

```
gctcagccat ggcatagttg tcataaactc atttatgtac gacctaactc taaaactggt    30720
gttcctgttg gacattggcc aattccagaa tcttttggc cagatcagaa tttaccttca     30780
ctagtaagtg tcataaaata aaaggtaaa catcattctg gattttcaat tttctgatta     30840
cagtgaacct tttaaaatag ctttgaggcc tttatgccat gccacaggca agtaagtctt    30900
ccctcctttg ccttctgtct cttacctggg aagtctagct ttgtgcctaa aagcaaaggg    30960
aggacttcct ttattttctg atacttgtca ttcttcagtt gccttcgcca cttgagctgc    31020
cctttttgga tgttaaaaca ttgctgtttt tgatgctgtt ataatctgtt acttggtttt    31080
catttcagag cagctgactt gatttacgtg gcaaacacaa cgtctaaaat gtactggcct    31140
tggttttcat gcacagcctc aggaagtttg aacatagttt acaccttgga taggttctgg    31200
gaacatatta aaatcatatt caaaattcta cttcttccta cttttcatct ttttgtaatc    31260
aatggacttt tgtagcaata tacctttcaa tgatgggtaa ttaagcaata tttaaaaaat    31320
aatctctaag caaggacttg tcttttggt cactgcattt ggtaggagag ctttgctat     31380 tacagttgct cccagtgcca gatcaattgg cttttttttt tttttttgg agggagggca    31440 gtgtctagta ataaggaga cggtatgaaa cccactctct tttgtcttct ttcccctcc     31500 ccaaattgta agagggcctg agtaatctcc cttgtgtggg ctcaggaggg gacacaaaca    31560
aatcactact tcttctattt aacatcttcc tagttcagtt catctatatt ctgtctcagt    31620
tttagaaatt tctgacagtg aattgcattt tctcctggat tactgctttt aggcttctgc    31680 cctttttca gaagtggcca tgaaagacct gaatgtaaga ctgaagagcc cttttggccc    31740
ctgctgtggg tgagggtaaa cgtcccactc ctctcctcag ggcttcaagg tgttacacct    31800
gtgaaacctc agcccttcca aactcgagta caggctttat ggcaaattta cttcattttt    31860
gctagcaaca agtcttcatt catgtcttta tgacatttt acctgttcaa atctaaggag    31920
tcagaaacct ttcacaagtt aattaaaact aagttgggaa aaacaaaat agaataagac    31980 attccaagta attcacacat agctcatgtt accattcctc catctttaaa agttcattta    32040
agagctattt ttctcaaccc ccaaacatct tataattgta aactataaag gcaagtgaat    32100
atgttttcat tttttataaa ggaagcagtg atattttatc atattcatat tagctttaca    32160
ggtttcgcaa caagaatagg ctgacccact tcttactttg tcttctggga cttgtcctgt    32220
gtccctctct ctccatattg cccttgctgt tcgcctttct ctctctgtg ctctccaatc    32280 acacaagcta aacctgttac ttaaatggct tctccattaa tctgctccag cacccccaggt   32340 acacaggcct tcgaagccca gcgcaaagnn nnnnnnnnn nnnnnnnnn nnnnnnnnn       32400 nnnnnnnnnn nnnnnnnnnn nnnnnnnnnn nnnnnnnnnn nnnnnnnnnn nnnnnnnnnn    32460
nnnnnnnnnn nnnnnnnnnn nnnnnnnnnn tcaacattca tcctacaatc ataagcactt    32520
cttaaacata ttcaaaacag ttttttttca attcactgaa attttagtta tgagtgttga    32580
aatttacctt tcctcttcct aatgtcaagt agatagtaaa gaatctgagc cctctctccc    32640
atggaagcca ttggtggttc ctagagatct agtaatcttc tttctcaaaa tgctagtctg    32700
tatttcagtg aaaatgtaac aaaatataaa acgacttgca gaattgtcag aaatataagc    32760
ttgctttgag acctaaccat ttttctgct ttttttaaaa aatttttttt agcctccacg    32820
aacatctcat cctgttgtga ggttctcctg tgtagattgt gagccaatgg taatagacaa    32880
acttcctttt gacaaatatg aacttgaacc ttcgcccta actcagtata tcttggaacg    32940
aaagtctccc cataccttgct ggcaggtact tatccttacc tattagctaa atgtctgtaa    33000
```

```
ccactctagg atctgggaat tgttttaaga agcttcaaag gttattctca aaataattgg  33060
actgactgtg ctaatgatgt ttctcatgaa tgctgtcaaa taagcaacag ggccaggcaa  33120
ataatttcag actaatatga atcattagtc tactgtacat tgccatttaa agcaatagag  33180
tctgatgaaa cctatatatt tgaagatttg ggggacccct tgaagtctac ccatgcaccc  33240
cagcttaaga atccctaatc taaaggttgt acttcacttc aggtatggcg tctgcagctg  33300
aaacaaggtg tttagcccct actttgaact tgacagattg gaagtacagg atagtttagg  33360
cagagaacca taagtcctga aactaatttc tgtattagtg taatataata aaactcttcg  33420
tcctgtggta caaatcacac taaaaaatgt gtgtaatgtg gattttgcaa cttggatgag  33480
acaaatgcat agagatatct atcatacact ggctcttcca agtgttacac ttaagccaga  33540
aggatttgct gattggttaa tagagtcacc tatggaattt aatttgtaaa aattcagaga  33600
tggcagtcac agccttttta tgtggataca acaaaaatgt cctacactgt aaagatgtat  33660
gttctatttc taaactgtag agatgtatgt tctacttcta ttaatatata ggactctata  33720
gcaatcagta actgttaggc tctatttatg caaggaacac tttcagactg ccatctgttt  33780
tatcttaaaa tgtgagatta ttgctacaag ttgtctgtaa gctacttaaa ttctcccaag  33840
atgctacaac tagttagaaa aaaggagca ggattaaagc aagaatgtaa agcacaaga  33900 aacagaataa tctcacaaac ataatactga gcaaagaagc tagacagaaa agattacata  33960
ttgtgtgatt ctatgttata tactttcaga gagagataaa actaacttac tctgttagaa  34020
gtcgggatag tggtttctct tggggggatg caaggtagtg gacagaagag gacacaagga  34080
gatgtctggt tttgttctct ttctttcttt cattcttttt gttttgtttt gttttgagac  34140
agcgtccagc ctgttgccca gggtggagtg cagtaacaca atctcagctc actgtagcct  34200
cgacctcctt ggctcaagca aagcgatcct cccacctcag ccccccacag aggagctagg  34260
actacaggca cacaccacaa ttcctggcta attttttaaa tctttttttt tttttttttt  34320
ttttagagag acggagtctc accgtgttgc ccaggctggt ctcaaactcc tgggctcaag  34380
caatcctccc acctcggctt cccagagtgc cgggatgatg gcatcaacca ttgtgcctgg  34440
ccatattctg ttttttgact cgtgtgctgt ttacacatgt acattcactt tgtgagcatt  34500
cattgagctc tatacttata gtttacccca aaagtgctag aaatgtagag atatggataa  34560
tagattgcta atttaaaata aagatatgac ctttgaattt atgggttgaa aaacattttt  34620
ataatgaaag caaataaaat tacaaattat agcttttccc taaaataacc cctcttttct  34680
atatagcaca tttcttggaa accttcttca gagaaactta agaaatgctg tccttgctcc  34740
tgcactaccc cttaaatatg tcatatgcct ctttcctgta ctttatgtta ctttttttag  34800
agtattctta atgtgatgaa ttagtgttag tgaaaaagaa taaaatgaac cagtagccag  34860
gaaatttggc aaaaccacaa tggagaccgg agcctaaccc tagctctgtc accaactatg  34920
tggccttgca cgagggactt acattgtctg aactagctct aaagatcctt tggaacccta  34980
aaaatctatg aatctgtggc tgataaggaa tttggaaaaa ctcaagggc caaggaaggt  35040 aggaaagaga aagagagaaa gaaacaaaat tcagtgcttt tcctttcatg ggaatcatag  35100
atctgaccct tgactgcctt gtgcatgtga ttttttttat ctttctttga tgaatttttc  35160
ctctcttcta atatacacac ttaggaaata aaatccagca tggtttattg cagttatctg  35220
tttctattat cattcaaatt atgacacaaa atctagtaga ctcatgtttt agtacaactc  35280
atgttctgtg gggtcataaa ttacataaat tacattcat aattataccca acttattctt  35340 agtgataata ttataagaag gtagtgaatt ggtaggtgat attggtagta ctgagaacta  35400
```

```
gcaaggtaaa tggattctgt taaatgtcaa ggttcgactt tgttgtaaat gattctgcca   35460
aaggactttg gaaaagtaaa ggaccaggtc tctaaaagta tatattggtg gtttggacca   35520
aagactctga acatggaaca gagaaaacat ggcagctagg gaccccagt acaacatatc   35580 aactgtaagg gggctgatga tacaggaatc acatcaggaa atcaataagg agtaagaaaa   35640
tagtcatatg gaattaagat caatgtttta atcttcactg aatgtttact ctaccagcat   35700 aactttttt tttttttttt tttttttttt tgagacagag tcctgctctg ttgcccaggc   35760
tggagtgcag tggcacaatc tcagctcact gcaacctcca cctcctgggt tcaagtgatt   35820
ctgctgccca gcctcttgag tagctgggat tacaggcgca ccactatgcc tggctaattt   35880
ttgtattttt tagtagagat ggggtttcac catgttggcc aggctggtct ggaactcctg   35940
acctcaggtg atccgcccgc ctcggcctcc cgaagtgcta ggattatagg cgtgagccac   36000
cgcactcagc cactaccagc ataatttata agagaaatgc cttccaggtt gacccaaagt   36060
atctccttgc tgcctcaaaa taattagcac cagtgcctgg cttattataa caggttactc   36120
agtaaatatt tattgaaaaa aaaatggata aatgggtagg ggaaggaggc agcaaagatg   36180
catggagcaa agacttaata atagtacaat gaagatggtt tacataatcc tttaagtagg   36240
ctttgttttt gtaatttcat gcttcaggca tgggactgtg ttctattttc ttcacagtct   36300
gcactctgat taccacttgt tcttttgaga agttaatttg ttttagtggc tggtttcctc   36360
ttagcagtat ttcagcttta tttttcattt tgctaagtaa gtaaatattt gggtactgtt   36420
gatgtggcct gtggtctctg aatggttgtt gcatagtata gtttcatttc ttaatataat   36480
ttataggaga attgcgatct gaacattcat atttagtagg attttttttg agacagggtc   36540
tcgctctgtc acccagggtg gagcgcagtg gcacagtcat gactcactgc agcctcaagc   36600
tccctggctc aagccatcct cctgctcagc ctcccaaggg atctggggac catagggcac   36660
gtgccaccac acttggctaa tttttaaat ttgttgtaga gaatgagtat ctccctttgt   36720
ctcccaggct ggtctcaaac tcctggcctc aagcaatcct tccacctcag tctcccaaag   36780
tgtcaggatt ataagtgtga gccacctgta atcctagtac atgagcctgg cctagtataa   36840
tatattttga cataaccata ggctaaaaac actattgcta ttttaaaatt acaatcaaat   36900
tgcgccatag atgctgctat ggaatgttac aatgggtttg gtttgacata aaatccttat   36960
tgtcatcact gtgcattact tcatgttatt ctcaggtatt tgttactagc agtggaaagt   37020
acaatgaact tggatatcca tttggttatt taaaagccag tacaacttta acttgtgtaa   37080
acctctttgt gatgccttac aactacccag ttttacttcc tcttttaggt aagtaaaaca   37140
tgtgccactg aatcatcttt aaaatacaac agaaatgaaa aatcgataat agactaagca   37200
ttttaaatgt agatgacggt aacaaattga tttgaaagga tagaatttgc atactgtttt   37260
ctgttttgtt tgttttcttt tgttgttttt tacatcaaac agaagagaag cttgactttc   37320
agtgtgtgat tcttatgctt gttcttcagg ttgcaacttc caatgcacac cccaccccca   37380
atccccagtt tgaagtgcac ttggcttttt tgtatagttt gggccaaaaa ataccaaaac   37440
agagctacca tggggtggga gtaatggctt gtgcttgttt cccctcagaa gataaatgct   37500
cttgaggcat ctgttttagg cagagtagtg agttaagaaa ataggtacca gagtaaattc   37560
tgcaatgact gtggttgtag aagctgtgat ttccatagca aggttctaaa aggaacaact   37620
caagaagctg ttactcagat actaatgaaa atgtgtgtgg agatatttc cccttattgg   37680 aagagccaca tctgtttaga gtaatgtagt acttactgca cagtatccta gttgtaaagt   37740
```

```
tgtaaatgtt tttatttcgt ggagtttctt aatttttgca aaaagggtcg aatctttact   37800 aagtttcat acgatcatta aaactatgag acttttagtg ctataaatac aacatacatt   37860
gaatatactg aaattgcaat acttttacat gtcgatttaa aagtttaag aatgagtcat   37920 cgtaaatgta ttagcatgat tatttaaat aacctatcta ctttatttct tagtgcaacc   37980
taagagggat gttctctttc taagagctga ttatcattaa cataagatat aggttatatc   38040
tttcagatta ataagacagc cagtaaaaaa gtgtctgtat tttgcagatt tatttatccc   38100
ttttcttaaa taagtcttta tgacttcagt ttccacaact ataaagtgaa gagattagac   38160
tatgtaatct tcactaccac tgttaatgat attattttc tattttaag tgcactttt   38220 ttgatctact ttattgagtt atgcttgacg tacaaaaagc tgtacatatt taatgtatac   38280
aacttgatga gtttggagat aagtatatac gcattaaacc atcacctcat tctatgccat   38340
aaacctatca gtcacctcca gaagtttcct cctgccctgg taagatctac cctcttactg   38400
accttttaag tacacaatac agtattgtta actgtaggta ctatgctaga aaacattatg   38460
ctgagtgaaa taaggcagac acagaagaac agataccaca tgataccact tacacacttt   38520
ttattttgag ataattgcag attcacatgt agttgtaaga aataatatag aaagagatga   38580
cctcaaaagc acaggctgca aagacaaaac tagacacatg ggactatatc aaccttaaaa   38640
gcttgtgcat caagggagac gattaacaga gtgaaaaggc aacctatgga ataggagaaa   38700
acatttgcaa atcatatatc ttataagggc ttaatttcca aaaaatataa ggaagtctta   38760
catttcaata gcaaaacaaa aacaaaaccc taaatagcct gcttaaaaaa tgggcaaagg   38820
acttgaatag atatttctcc aaggaagagg tacaaatggt taacaagcat atcaagagat   38880
gctcaacatc actaatcatt acagaaatgc aaatcaaaac tacagtaagg cattacatta   38940 caccctcag gatggtcact atcacaaaaa cagaaatga gaagtgttgg taaagatgtg   39000
gagaaatcgg aattcttgtg cactcttagg aatgtaaaat ggtgtaacca gtatggaaaa   39060
cagatagaag tacctcaaaa aattaaaaat aaaattaacc atatgatcca gcaatcccat   39120
ttctgagtat atatccaaaa gaatcgaatc cagaatcttg aagatatatt tgcacaccca   39180
tgttcactgc agcattattc acaatagcca aaaaaaatc cattgatgga taaatgaata   39240
aagaaaatgg ggtagatata catgcaatgg aatattattt agccttaaga aggaaatttt   39300
gtgacatgct acaatatgga tgaacctagt ggacttatgc taagtgaaat aagccaaatg   39360
acaaatattg tatgattcca cttacatgag gtattaaaag tagtcaaact catagaaaca   39420
ggggctgtgt gaggggaaaa tgggaacttg ttacttcagt gggtaataga gtttcagttt   39480
tgtaaggtga aaagnnnnn nnnnnnnnnn nnnnnnnnnn nnnnnnnnnn nnnnnnnnnn   39540
nnnnnnnnnn nnnnnnnnnn nnnnnnnnnn nnnnnnnnnn nnnnnnnnnn nnnnnnnnnn   39600
nnnnnnnnnn nnnnnnnnnn nnnnnnnnnn nnnnnnnnnn nnnnnnnnnn nnnnnnnnnn   39660
nnnnnnnnnn nnnnnnnnnn nnnnnnnnnn nnnnnnnnnn nnnnnnnnnn nnnnnnnnnn   39720
nnnnnnnnnn nnnnnnnnnn nnnnnnnnnn nnnnnnnnnn nnnnnnnnnn nnnnnnnnnn   39780
nnnnnnnnnn nnnnnnnnnn nnnnnnnnnn nnnnnnnnnn nnnnnnnnnn nnnnnnnnnn   39840
nnnnnnnnnn nnnnnnnnnn nnnnnnnnnn nnnnnnnnnn nnnnnnnnnn nnnnnnnnnn   39900
nnnnnnnnnn nnnnnnnnnn nnnnnnnnnn nnnnnnnnnn nnnnnnnnnn nnnnnnnnnn   39960
nnnnnnnnnn nnnnnnnnnn nnnnnnnnnn nnnnnnnnnn nnnnnnnnnn nnnnnnnnnn   40020
nnnnnnnnnn nnnnnnnnnn nnnnnnnnnn nnnnnnnnnn nnnnnnnnnn nnnnnnnnnn   40080
nnnnnnnnnn nnnnnnnnnn nnnnnnnnnn nnnnnnnnnn nnnnnnnnnn nnnnnnnnnn   40140
```

```
nnnnnnnnnn nnnnnnnnnn nnnnnnnnnn nnnnnnnnnn nnnnnnnnnn nnnnnnnnnn    40200
nnnnnnnnnn nnnnnnnnnn nnnnnnnnnn nnnnnnnnnn nnnnnnnnnn nnnnnnnnnn    40260
nnnnnnnnnn nnnnnnnnnn nnnnnnnnnn nnnnnnnnnn nnnnnnnnnn nnnnnnnnnn    40320
nnnnnnnnnn nnnnnnnnnn nnnnnnntag ttatttaaga aaatagccta aatgtttccc    40380
agagtagcta tactatttta cattccccac tattaagtgt atgagtgaat cagtttctct    40440
gcatcttcat cagccattgg tgttgtcagt atttttaaaa ttttagccat tttgataggt    40500
gtatggtgat atagcactgt ggttttaatt tgtatttccc taatggctaa caatattgat    40560
catcctttct atgtgctgat gtgatgatgt gccattgtat atgttctttg gtgaactgac    40620
tttccctat atttttaatta gattgtttgc ttttgttact gttgagtttt gaaagttctt    40680
tatatatcat agatactagc cctctgacag ataggtgact tgcaaatact tatttagatc    40740
ttttttgatc tttcattggt gttacgcagt tttccactta caaatacggt gcatattttg    40800
ttatatttac acttacttca ttttttgagt gattgcaaat ggtattgtat ttttgatgtt    40860
ggtatctaca tgttcactgc tagtatatac aaatacagtt gattttatg ttaatattgt     40920
atcctgcaac tttactgagc tcacttatta gttgtaggag agttttgtag attccctgga    40980
atttcaaca tagacaatta tgtcatctgc aaatagagac agttttacct ttcctattct     41040
tatctttatg ttttttcttt tcttttcttg ccttactgta ctgtagagaa cttccagcac    41100
tgtgtttaat ggcagtggta agatgtatgt tccatcggtg cttgacaact atgcactatt    41160
cattcttaca ttaagcataa tgcttttgta gattttcttc atcaagttga agagttctgg    41220
ctgggtgcgg tggctcacgc ctgtaatctc agcaatttgg gaagccaagg cgggtggatc    41280
acctgaggtc aggagtttga gaccagcctg accaacatgg caaaccctg tctctactaa     41340
aaaatacaaa aattagctgg gcgtggtggc acgcacctgt agtcccagc tacttgggag     41400
gctgaggcgg gagaatcgct cgaacccggg aggtnnnnnn nnnnnnnnnn nnnnnnnnnn    41460
nnnnnnnnnn nnnnnnnnnn nnncactgc aacctccacc tcctgggttc aagcgattct     41520
catgcctcag cctcccaagt agctggatta caggcatgta ccaccctgcc tggctaattt    41580
tcatattttt agttagagac ggggtttcac catgttgggc aagctgatct tgaactcctg    41640
acctcaggtg atccattcgc ctcggccttc caaagtgctg ggattatagg cacaagccac    41700
tgggccaggc ctcaaatgtt ctttctgcat catttgatat gaccatatga ttttcttct     41760
ttagtctgtt aagtatgatg gattacactg actaattttc aaatattgaa ccagctttct    41820
atccctgaaa taaatctcac ttggtcatgg catataattc ttttcatata tattactgag    41880
ttctatgtgc tgatattttc ttgagtaatt ttgtgtctat attcatgaaa gatattggcc    41940
tgtagttttc ttttttgttg ttgtctttgg ttttagtatc aaggtaatac aagctcttca    42000
taaaatgaat tgggaagtgc ttctcctatt ctgttttctg gaaagattg tgtataattg     42060
gtattaatta ttctgtaaac atttgataga attcctgagt gaaactatct ggttctaaac    42120
attcctgttg ggagttttca aattattaat tcaatttctt tcatagttat agggttattc    42180
aaattatgta tttcattgag tgaaatgtgg ttatatgtcc ttttgaggaa tcagtccatt    42240
tgtccatttt atctaagttg tgaaatgtat gtgtgtagag tcattcttag caatcccta     42300
tggtcctttt gatgtgtaca gagtctttag tgatatcacc tatattattc ctggtattga    42360
taatacgggt cttatgtctt ctttgtcttt gtcagccttg ctagatgttt gtcacttta     42420
ttaatctcat caaagaacca gctgtttcat taatcttatc aattttttt ttaaatttca     42480
```

```
ttgatttatt tcctttcttc ttactttaag tttgttttgc ttttcttttt tgattcttgg   42540
tatgggatct tagattattg gtttgatact tttcctcttt tctattgtaa gtagtactca   42600
gtgccttaaa tttctctcag cgctaattta gctgctttcc gcaaatttta catgttgtcc   42660
ttcattttca ttcactttac tttgtctttt gatttctcct gagacttatt tgacccatag   42720
attatttaga agtgtattgt ttgatttcca agtatttga aatttaccta ttatctttt    42780 gttactagtt tctagattga attccatcgt ggtcagagga cacatctgta ttcgatatct   42840
actcttataa atatgttgcc atttgcttta tggcaaagca tattttctat cttaatatat   42900
attccagcag tgcttgagaa taatgtatgg tctcatgttg tttggtagga tattctacaa   42960
gtgttaaatt gttcctgttg gttgatggtg ttctgctata tccttgttga ttttctgtct   43020
atttgctcta tcagtttttg agagagggtt gttgaagtct ccaactataa ttgtggattt   43080 gtctgttct  ttttcagttc catcaatttt tgcttcaact attttgcagc ttttacttgg   43140
ttcatacaca tttagaatca tggtgtattc ttccttgatt gatcattatg taatgtatct   43200
ttgctaattt tctttgcttt taagtctgct ttatcagata ctaatgtatc cacttctgtt   43260
tttctttgat gtttgcatga tatatctttt cccatcattt tactttgaac ttgcctataa   43320
ctgttttgtt taagtgagtt tcttatggac agcacatttt tgggtcatgt tttttaatcc   43380
actctgccaa tctttgtttt ctaattgatg tatttagata tctgcattta atgtgattat   43440
tgttatgtta gggcttaagt atgccatctt atagtattgt tttctctttg ttctattttt   43500
cttttctctg ttttcatttt actggcatct tttgggttat ttaaacgttt tttagaattc   43560
tattttcttt tactatagta ctttcaagta tatctgtttg gatagctttt ttagtgattg   43620
ctccaggtgt tattatacac aaattaccac agtctactcg ttctcattat tttactaatt   43680
tgagtggaat atagaaactt tatctctcat tatattccct taccctcctc tatttataat   43740
aaaattatct gaactatttt atgtacaatt agaaatacat gaggcagtgt tataactttc   43800
gcttcaactg tcaaacataa tttagaaaac tcaggatgaa agtccattgt tttaaaccat   43860 atttggcat atcctgttct ttcttcctga taattcaagg tttgttcttt tatgtttaat   43920
ttctgtttaa agaacatcct ttagctgttt tttaagggta ggtctgctag tgacaaattc   43980
tcttagtttc tcttcatctg agaatatctt gatttcccct tcattcctga aatatatata   44040
tacatatata tatatgtata tacatatgta tatatccata tgtgtgtgtg tgtgtgtgta   44100
tatatatata tatatagcta ggtatagaat tctcggttga cagtacttt atttagcac    44160 tagaaaaatg ctgtgtaact gccttctgtt ctttggttt ctaatgagaa atctacttta    44220
attctaattg ttcttcctct gtaagtgagg tattgttttt ctttgctttc aagatttatt   44280
tctgcctgta gttttcagaa gtttgattat gatgtgtctt ggcatgcact cctctgagat   44340
tattctgttt gaggttcatt cagcttcttg aatctgtagg tttatttctc cttccaaatt   44400
tggccggttt tcagccatta ttaccttgag tacttttca gccccacttt ctttctcttc    44460
tccttccagg attctgttga catgaatgtt agatcttttc ttatagtctc ttaggttcct   44520
taggctccgt tcattttttt cattctattt tctctgttat tcagattggg taattacat    44580 tgttctattt tccagttcat tgattatttc ctctgtcccc tgcattctgt tgttgagcct   44640
atctactgag cttttatttt tggttattgt atttttttaa ttctaaaatt tccacttagt   44700
tattctttat atcttctatt cttattctct gtttctttgc atgtgttttc atttgtttca   44760
agcctgctca tattattttt tgaaacatgt tttatgatgg ccgctttaaa ttggatattt   44820
ttaacatctc tattatcttg gtgttggcat ccccttaattg tctttttaaa ttaattttga   44880
```

```
ggccaggcac ggtggctcac accttaatca cagcactttg ggaggccaag gcaggtggat    44940
cacttgaggt taagagttcc agaccagact agcctggcca acatggtgaa accccgtctc    45000
tactaaaaat acaaaaatta gccaggcatg gtggtgcacg cctgtaattc ccactactcg    45060
ggaggctgag gcacgacact tacttgaact tgggagacaa aggttgtagt gagcccagat    45120
cacgccactg cactccagcc tgggtgttgg agtgatacac tgtctcaaaa aaaaaaaaaa    45180
aattaatttt gagatctttc ctggttcttg gtatgatgag tgattttttt cctgtacatt    45240
ttcaatattt tgttatgagt ctctggatct tacttaaacc ttctgtttta acttacttcc    45300
tctcacaccc ctcttggaga aactgggagg tgctgcctca ttcatgccag gtagaagtcc    45360
aggctcgcca cttggccttc attgacacca aagggaggg atctcccttg ttattgttgt     45420
gtgtgagtag gagttctgga tcctccctag aatgatacct tcctggctgg aagagatagg    45480
aatgcttcat tatcttccac acttgacctc cactgacacc atatgggtag aggtgacctc    45540
attactactg agcagttgtg aaagtcctat acaactatta tgggctaagc tctagggtcc    45600
catctttggt ctaaatccag cctgccttcc aaattattcc ctgaaaattc ctttaactag    45660
agtagctggt cttccagtag ctatcaggat gtagagcact ttacaatagc aagactcatc    45720
ctctcatctt tgcctttgct cgtctttcag gtaatggagg tcagatgaag gcatgacata    45780
atggttaaga ggaatgatta tagtgtgatc aagcattcag ttctcccttt gcctaaaacc    45840
ttctgtgctt aagttgccat gtggtgccct tccccaaact cctcagcact atgccaagtc    45900
aaatcctgac actgtcttcc tggtcacctt ttagtttgca tcactctatt cctcaaatgt    45960
caagtgtttc ttctgtttga agtgtcttct gtcaccagta agacatgtgt ggcatctgtg    46020
cctggtcctc cttagcctat aacactaaga ctccaaccct gcctagagca tgatgaccta    46080
aattattttg gttgcccaac agccttctgg atgtttcaag agtgtcttca agccaagctg    46140
aactcttacc ttaccatgct cttcctcctc tcttcacagt ttagttagtg gcatcaccat    46200
gtctatgcaa acatcccaca ccagaaactc tggaggcatc tttgactctt ccctgttcc     46260 ctaatcccat acattcagct agggtccatg ccaatcttga ctcagttccc attctgcccc    46320
ctggcttcaa atatccatct ccaggccttt ctgtaacctg tgtttctga ggagtatagg     46380 gttttttaaca ccctttgagg ctggaggtcc ttgagctcct aaagtccaaa cttgggattc    46440
cttgtgagtt tctgaaataa acagaaactc aacatttcca taattactta attctctggg    46500
gagtttgaca tttatagtgg ttaagagttt gggctggagg gcatagctgc ccaggtatga    46560
atctggctct gctacttgct agtttcatga cgtttgggcaa gatacctaat ctgtctatgc    46620
ctcagtttcc tcattagtga aatggggata atgatagtac ttacctcaaa gggatttagt    46680
tggaattaaa tgagttaata cagttaaatt gtttagaact tgcctggcaa atagtaagtg    46740
ctcaataaat gctgttgtta ttattactgt cattattaat acctacatta tcttagtagc    46800
tctcgaaggc actgctatat tatactaaga aggctattgt ataattttgc agttttagtg    46860
gacagggaca gttagtaaaa gggcaagtta agttacacac actacataag tccagaagca    46920
tcactatatt actgcatagt acagtaattg ttcataacag tgtcccttgt tttctttttta    46980 ttaataccag atttcaatca aattaaggtc atgaaagttt aattacttat gcactaaaac    47040
ttaccagaaa atataaaata tctcattttc tggaatagat aaacgaagct taattgtatc    47100
aatgagctac cagaatcatt tcattaagga ggtcaccaga ttgttgtagt tagcaaagga    47160
ctctctccca attaggaaat tagttttttct attgagacct aataactgca gaaattagag    47220
```

```
catttgtaac aacttttttt ttcgttttct taaatatatc acattcaatc cacctgttct    47280
tttaaattaa gaactgagga cttgtgtaaa aaataaactt tagttccata ttaaaaccag    47340
ttatgatcag gaggaagaaa gggagaggta tgagaataga gaatagaagc aggatacttt    47400
gatgtgtatc agtcactatg tatctggtgc ttaacagctt acactggttt gtttgttttt    47460
cattttgtac ggggctttta cacatacatt atgtagttcc ttagaatagt cttgtggtaa    47520
ggcaattatc atctaaccca ttttatagat gaaatggagg cttacaaaag gcaatttctc    47580
caaactcact gagctaagga tgtggctgag cttgaactca aacccaggtc ttccctctct    47640
ttgaagaaag aaatggggag aaaggaactg gaagagaaaa taccggtcat ttttgaggtg    47700
ctggcagtat cattttactt tcattctaca ctctcatcac atcttctttc aaatgttgat    47760
cagctaattg tttatgtgac acctttactg taccatccta gagagtccat gtgaatgggt    47820
atttaatgcc atgggaaata atttgctgag ctacagaggt agtgactaag gcagtgtcac    47880
cccaggagct ctctactctt aatctagact gcagaagatt ttctttcttc tcctgactcc    47940
cattttaaaa ctctggcaga aaataattag cctaaatgag ctccttggtg gaatcattgc    48000
acttggcatt gttagaaatg caaagagtat tattcacttg attatctaat ctatttatat    48060
ctaaaagttt ctccagtatt tacgtttgtc cgttagtttc caaaatctgc ctaattccca    48120
acagactcca cataaagaca tggtataaca ggatatatcc atggtctctc attcctttct    48180
gtcaagatat gaatggtctt taaggcccc acttgctgca atgaaccaga aatatcttca    48240
aatctttaac aaaagaccta catttatga ctttgtaaat tcatttaaat ttgtttcagc    48300
aggagtgaat aatttattat agctgtaaaa ggaaggaaat atgtagtcgc ttttcttaac    48360
taaagtaatt cagattttca aagaatagcc ctatttgtaa agaaattatg catgtgggat    48420
agggatggtt ttgtctctgt aagtaaagca ttttttttaa aaaaatcaaa actactaaaa    48480
ccttaagaca caaataaag gatgaattta tagtgtctt ggtacctata gtatgtgtgg    48540
cagattcatg ttgatgtctg gggattccaa tttttatatt tttattgtat tagaaaaatg    48600 ttttttttctt acacttggaa ggaaataatg agatgtgaag gaaattttca tgcgtatata    48660
aaatgtattt agattattaa aataattaaa tttaagtgtg aaaagatagg ggaatgtcta    48720
cttaggtaaa tattttagt tcaaatattt ttagtcacatg gtattcaaga aacatgttta    48780
gttgttctac agaattttaa acttcaaccc taacatctgt acttacttct actagtgctt    48840
ttactatcac ccaatgactt ttagnnnnnn nnnnnnnnnn nnnnnnnnnn nnnnnnnnnn    48900
nnnnnnnnnn nnnnnnnnnn nnnnnnnnnn nnnnnnnnnn nnnnnnnnnn nnnnnnnnnn    48960
nnnnnnnnnn nnnnnnnnnn nnnnnnnnnn nnnnnnnnnn nnnnnnnnnn nnnnnnnnnn    49020
nnnnnnnnnn nnnnnnnnnn nnnnnnnnnn nnnnnnnnnn nnnnnnnnnn nnnnnnnnnn    49080
nnnnnnnnnn nnnnnnnnnn nnnnnnnnnn nnnnnnnnnn nnnnnnnnnn nnnnnnnnnn    49140
nnnnnnnnnn nnnnnnnnnn nnnnnnnnnn nnnnnnnnnn nnnnnnnnnn nnnnnnnnnn    49200
nnnnnnnnnn nnnnnnnnnn nnnnnnnnnn nnnnnnnnnn nnnnnnnnnn nnnnnnnnnn    49260
nnnnnnnnnn nnnnnnnnnn nnnnnnnnnn nnnnnnnnnn nnnnnnnnnn nnnnnnnnnn    49320
nnnnnnnnnn nnnnnnnnnn nnnnnnnnnn nnnnnnnnnn nnnnnnnnnn nnnnnnnnnn    49380
nnnnnnnnnn nnnnnnnnnn nnnnnnnnnn nnnnnnnnnn nnnnnnnnnn nnnnnnnnnn    49440
nnnnnnnnnn nnnnnnnnnn nnnnnnnnnn nnnnnnnnnn nnnnnaggtt gggaaaatat    49500
ttcaagtggg atccaaaatc attgttttaa tattgtattt catgtagcat tgcagatgaa    49560
agaggaatat gtaacttaag aatttatttc atttttagaa aaaatactaa tatataattg    49620
```

```
tggtaaatag tacaaccact aaaaaagata atcaaataaa cgccaatgaa attttcatct   49680
acattaaaag ctgaagtttc tagatgtggg ttgcttgatt atatcttaga gctcaggact   49740
agaatgatgt aatattttat ttttctatta cagatgactt gtttaaagtt cacaagctta   49800
agccaaatct gaagtggcga caggcttttg acagctactt aaaaactctg cctccatact   49860
acctattagt atgtatttgt gtgtatatat gtattaactg tatcaatgat aattcttgtc   49920
acaagaaatg ttagtgatca aaagctttta ctgttgcaat aagagagata tcttttattt   49980
ttacagatat ttgtgtcgtc actgtcttct caaatcatgt gtaagagttt ggagatgtca   50040
tggcggcaca aaagagagct gttttctcta ttttattcct ttaactgcca tggttatttt   50100
tataaaacac atctatgttt ctcttattaa agtaaccttt aatttcattg ggaatttaag   50160
aataaataga tctggattca tatattacat caacttccct ttttaactct agaaattctc   50220
agtatggggt ttccctctgg aaaaagaaaa tctgaagaca ttacagttgc ctattgcctc   50280
ttaaatgtgt cctagacaca gcatgaagtt ggggcactgg tggtgagagg cggaatccaa   50340
aaaaattcag aaatgacttg gcctcatttt ggatttcata atgtgaagta ttcatgattt   50400
tgaactggta atataatcta aatcaagatt accaaaataa tttcagaggt tgatgtggta   50460
acctttaagc gaagtttcta gaggtgaaaa ggcagaatct taaatggtac cattggtgtc   50520
actgggagga gaaattgggg tgtgttactg tttaccatgg cagtaatggg gcaaacaata   50580
aaatgcaatg tgaaatgatt tgatgatttg ggaaataaga ttgaacgcaa tttacttgtt   50640
tgaatttgct gttacttgct cttcttatcc cactctcttc tgatttttt ttactttctg   50700 ctccttactt ctctgctatt ttcattgcca cttttttaatg ttccatgttt ggttttatgt   50760
gcagcacctt gacttctaag aaatgaatca tgtccctttg cccctttataa ctgaactttg   50820 agtattttaa gatttattct attcttactg ttgtgtattt tgtttcctta tagccattaa   50880
agaaagcact aaggatgatg ggagctccaa atctgatatc agataattta gattgtggac   50940
ttagttacag tgttatctct taccttaaaa aactcagcca acaggtagta ttggtaaaaa   51000
caaacaaaca aaaatccttt gccctcagaa gtgcatttcc ttattcttta gtgtaattgt   51060
aatttttcaa attaaatgtg tatatatctc tacactttat ggattagtaa taatgtgatt   51120
ctctatggct tctagcttca ccattaagct gcagttaagg gtctgtcagt atcatttgat   51180
gctgtgccat ttctcctttt gcctgccagt ttgtcctacc cgcaagctgg ttgatatggg   51240
gcagaggttt aatagacttc tctcatgggt cacattttgt ctatcttcaa cctagttcct   51300
cctcagatca ctctgggcta cagcatccct cctgtttaga tcagcacact gaggcgtggt   51360
gtgattaaat gacttgtctg agattagttt tcaggcatgt gaaggactta tactcacatg   51420
ctagcccttg gataaagagc tatatgcttt tccctggaga gtggggagat gagaccagtg   51480
ttcctcacac tggagggtga tagaccccaa ggggaactga agagtggagc tcagtttcct   51540
ctcttctcac cctccacctg ttcctcattt gccattattc accttgtccc ttgcctgccc   51600
ctctctatta gtacctcatc ctccactcac cgttccttat catacttctc acctctactt   51660
agcccattct tgtaggatgg aaatatttga gaactactga gttagaactt tactatcata   51720
tgaatgtgtt atgttatatg acaaattaat gcagcagttt tacttacctt atgcacaaag   51780
gtattcccag gtagggggaca atagtagcat tcgcagtggt gataatgctt caaggtggat   51840
gtgtttggaa gtttggcctt taggaaatgg agagtagtga gcaaaacatc agatttcacc   51900
aaagaaccaa agtgactcca caattgggat gccgacacac cttgctagga actgacaaca   51960
```

```
acttcagtat ggtctggagc ttaccagctc ctaccagtcc agtgtgctta taagtgcaaa    52020
agaaagtaaa ggcaacccca gatttctaat ctaccaagtg tcccctaac ctcctttcct     52080 ctctgctaat agatttttg tggttgttgt aaatgttttg gtttggttat ttatttattt     52140
atctatctat tgatctatcg atttttttta atttgatgtt tacctaagcc tttaaggctg    52200
tgtcaccaag gtatggccac aaggaagaat agtgtacaga gattttaatt aatgcaagtt    52260
ctgggacctt tgggcaca tgtatcattt tacaaatgag ctttcaagac catttaagga     52320
aacagatgct tcatttgctc ttatctcata tttcatgact taagaatttt ttagtgataa    52380
taaacataga cttaattcca ataattaggg aaaattgata aatatctgtc accaaaccac    52440
aagaaatcca aaatcatttt aggtttacca acattggtg gaattccatc tttctgagaa     52500
aaagggaaga tcatagctaa tttataatag ctcaaattac taatttaata actgggtcac    52560
cagtgtttct tgagccattt cagatgtatg taaaacacaa aatatgccaa atatatattg    52620
ctataataca ctcaagcagt attaatcaat atggtatcac aatgcctatt aagaggcttt    52680
ttacaaatta cttacttagt aatatctgtt aaattaagca ttatcttcta agaccttttt    52740
tggatagtca aatataagag ataaatagtt taatttttc agcctttttt tggatagtcc     52800
aatattagag ataaatagtt taatttttc agatataatg ccagtcgatg tgatctgaat     52860
tttagtacta gtttacacgt ataaatacag tcttaaacct ttatgtctga gtctgaaatg    52920
aacctgttca cttagactag attttatagt aacaaaatgt gctttaaat gtctatgaat     52980 gaaattctta ttcatggttt ttattctctc catgatttta ttataatttt gacactagac    53040
aagaaaaaaa aatattattt gtctttcctg cccctatct gtttgctgtg atagtgcaaa     53100
gaagcacagg aaaatgttta attatccatt tttctgtgat ttgtaattga aaattgttct    53160
gtggggttct gaaagtatta tctttcttaa gtagtaaaaa tgacagtggt aatgtagatg    53220 ttttataac atactatgta ctttcatttt agaccaaact agagtcagaa cnnnnnnnn     53280 nnnnnnnnnn nnnnnnnnnn nnnnnnnnnn nnnnnnnnnn nnnnnnnnnn nnnnnnnnnn    53340
nnnnnnnnnn nnnnnnnnnn nnnnnnnnnn nnnnnnnnnn nnnnnnnnnn nnnnnnnnnn    53400
nnnnnnnnnn nnnnnnnnnn nnnnnnnnnn nnnnnnnnnn nnnnnnnnnn nnnnnnnnnn    53460
nnnnnnnnnn nnnnnnnnnn nnnnnnnnnn nnnnnnnnnn nnnnnnnnnn nnnnnnnnnn    53520
nnnnnnnnnn nnnnnnnnnn nnnnnnnnnn nnnnnnnnnn nnnnnnnnnn nnnnnnnnnn    53580
nnnnnnnnnn nnnnnnnnnn nnnnnnnnnn nnnnnnnnnn nnnnnnnnnn nnnnnnnnnn    53640
nnnnnnnnnn nnnnnnnnnn nnnnnnnnnn nnnnnnnnnn nnnnnnnnnn nnnnnnnnnn    53700
nnnnnnnnnn nnnnnnnnnn nnnnnnnnnn nnnnnnnnnn nnnnnnnnnn nnnnnnnnnn    53760
nnnnnnnnnn nnnnnnnnnn nnnnnnnnnn nnnnnnnnnn nnnnnnnnnn nnnnnnnnnn    53820
nnnnnnnnnn nnnnnnnnnn nnnnnnnnnn nnnnnnnnnn nnnnnnnnnn nnnnnnnnnn    53880
nnnnnnnnnn nnnnnnagaa agtcttggcc agcacagtgg ggacctctag caccaagatt    53940
tcctacagag gagggccaca ctgggcagag ctggccaggc cctaacaccc tgccattgtc    54000
tgttactggc tatgggcagc ctgggaaggg catggcctca gctcagtgct gcagcggatc    54060
cctatggcac cacagcagcg ggaggctctc tgctaactgc actccttgca ggatcagcca    54120
ttgctttcct gaagggagat cccagcagct cacctcccct ccatggctgc cagaggaata    54180
catctagagt acgagcagtg gtcctgcaag gcggccacag gtatcaatct cgggatttgg    54240
tgttttaaat gacatatttg aaagggata gtcccagtgg ctttaatacc ctgtaggtgt     54300
gttacaatgc agaacaaggc tagcaagtgg aattttgcca ctgggaaaat tctactgtag    54360
```

```
tcagttgtat tgatataaca ctcttcaata acatttttaag agagataagt atgacatttc    54420
tatattaaaa gccttaggag taactgaaat tatttgtttc atttcaaata ggatttgaaa    54480
cctcagacat acagaaatgc ttatgatatt ccccgtagag gtcttttaga ccagctgacc    54540
agaatgagat ccaatctgct gaaaacgcac aagtttattg ttggacaaga tgaaggtaaa    54600
ataactgtga aatacttttt ttttttttt ggaaaatgcc aggcatgact tacaggaagg    54660
tgtttattgc ataatgagta ggctatttta tagtatttta atgtttaaaa tgcctgtttt    54720
cactgaatcc ctatgtctgt ttaccaggca cattttttt ttcaagttta aggtcaagtg    54780
tgcattaatc agcacgtaca ctacacttgc catgctttag ctattgtaag cttcaaacaa    54840
ccccaggaaa tagatactgt ttttatgtcc aattcatgga catggaaact gagagtgagg    54900 attttagta gtttgcccaa gtttagccag ttggaaagtg gcagaaccta ggtctgtcag    54960
atttcccaat ttgcacaccc aaacactaac actcagccta ctgtgataaa ttcagtagag    55020
aatacctcat ttaaatgaaa gtaatcaacc taatggtatc caggataatt gtgactattt    55080
acaaattcca tttactccat tttgttaatt ttaaaaaggc tcacctgttc actaaaatga    55140
gcaaatctta ttctggtcaa ttccctgaaa ttatacacaa agttttgtgt gtaagagggc    55200
ttttctagga agagaaccta cagatttaat caaattctca ggattaagac ctactaacca    55260
agattctctg gatgataagt gaatgccata gagactagac tctttgaaat gcagaagata    55320
tgtggtgatt tgagttggga tggtggtgta gggtcagccc attctcaaac ctggtttgaa    55380
ggcaagggag ttgttctgat cctagcgatg tgagcctgta ggcagtagta acggtagact    55440
aagttatgat tgggatgaag agagatgatt ctagatccta gaatgctaga ttcgagactt    55500
taaatactat ttgatgccaa gacacacact gctaaaccaa actatgatca tgtcttctcg    55560
aaaggaccat acgcttcagc tataagcatc aatttctttt cctgtgattt tgcagattcc    55620
cttcatagtg ttccagttgc acaaatgggt aactatcagg aatatctgaa gacattggct    55680
tctccactgc gagagattga tccagaccaa cccaaaagac tgcatacttt tggcaatccg    55740
tttaaacaag ataagaaggt aggatacccta tgcctatgtc tgcctaaatt gggatattct    55800
tgctatataa ttatttttctt tttggcaaga taaatacaaa tcagaggttc ttcatttgtt    55860
tgtttaaaca ataaaatatg acactaaggc tcttagtggg agcctcctga tgcaagagtg    55920
tgttggttga ataaagtcag agctgccatg tattgagtac tagtaggagc tggtgttttta    55980 aatgatctca cttaatgctc acaactgttc tgtaagacaa atgttactgt ttgtcccttta    56040 aaagggagaa atcaaaggcc acagtggtca aacgccttac ctgtgacata gcacataaga    56100
gcaaggattt gaatccacgt ctttctcact ccagaatcta tattcattcc accacacact    56160 aatttctttta atatcaaaat cacagtttat ttcctgtttc catgattcat atctgtagtg    56220
cttgatctag aaaacgatga atgtgtccct tgaaatatga agtactaagt gatgttgttt    56280
tacttgaatg gtcctactaa aaatctaaat gtggggagtg tgtgtgtgtg tgtgtgtgtg    56340
tgtatgtgtg tgtgtgtgtg ttatactgac ttgcccatta aagcatgaaa acaaatggga    56400
ttatagctgc actcatggag gagaccattg gtgttaatta aggctcagac cacacaataa    56460
tctcttttgt gacaagactg attgaaaggt attccacgtc acctaaatcc tcaatttatc    56520
tttctatgct tcactttcct cattttgtag cactgggaat aataattaca cctaactatg    56580
ctggacgagg tggctcacgc ctgtaatccc agcacattgg gaggccgagg caggcaaatc    56640
acttgaggtt gggagtttga gaccagcctg gccaacatgg caaaaccctg tctctactaa    56700
```

-continued

```
aaatacaaaa attagccagg cgtggtggtg ggtgcctgta atcccagcta ctctggaagt    56760
cttaggcagg agaatcactt gaacctggga ggcggagatt gcagtgaacc aagatcgtac    56820
cactgcgctc cagcctgggt gacagagtga gactccatct caaaaaaaaa aaaaaaaaaa    56880
attacaccta attaactaat agaactctgc ataatattaa gtgagtacat gtacattgtt    56940
tacaacatga acaggcatgt agtaaattat ctgaaaatgt tttcccctt ctgtattgtt    57000 tatgagtaaa aaatcttttg gaaaagccat ttattattat tttattcaac taatgagggc    57060
acatattctt ggattattcc tggacaagaa cagctcttgg ctaaatttct atactgctgc    57120
ctctcatctt ttatctatcc ccccaagagt gaaaagcctc ctcactgcct gcccagcacc    57180
aaagtgggca tatttgaatc tctgtgaggc tgcagatggg gaagttacat tttccacctg    57240
cctgcctttc aacacgtaca tgtagcatac tgtacagtga taatcaatgt tgtttaatga    57300
tatgagtttg gagcataaaa aaggaaatta tttcccttat gaagagttga tgcaaaatag    57360
ttcgtacttc tctccttttg gttgaataat gctgcttatt tgcaaacttt ctgattaatc    57420
attattgtag tatgttttgc ttgggacaac atcctgtatg ttagtttcct ccttgttcca    57480
tttaaattgg attaaaattg agttgcatat ttctaagaac aaagttgggg tggggtaaga    57540
taaatcttcg gcccatgatt aaggtttata ttagttaatc tggcatggga tttaaaaaaa    57600
tgaaagaaaa aaagacatat tcgtgatata atgcaagatt gattatgtat gcatattaag    57660
agtgcttgca gttatataat agtgaattt tggtctttaa tgaaatacgt tcatttatgt    57720
gttttttagg gaatgatgat tgatgaagca gatgagtttg tagcagggcc acaaaacaaa    57780
gtgaaacgtc caggggaacc caacagtcct atgtcatcta agagaaggcg gagtatgtcc    57840
ctgctgttga ggaaaccaca aacaccacct actgtaacta accatgtggg cggaaaggga    57900
ccaccctcag cctcgtggtt cccatcttat ccaaacctca taaaaccac ccttgtacat    57960 acaggtatag agtagtggtt gtgatttcct tatggctcct agaggactaa gacgctaaac    58020
aattttattt cccttttgt gttccttcct ttgtgttcag tttgtgttca ttaagtaagc    58080
cattactaaa tcatctattt ggtaggtaca ataaacccca cagggagcag agaccctgtt    58140
tcaaggatct caatctacat gaggtgaaaa aaattataat tatatagtaa ttaacacaca    58200
gtaattaaca gtaatgaata cattgcttag caagtaaatg ccacagtaat taatgggaaa    58260
atggaaagag gtgagcatgt ctgctgcaac cttttggagt ggctgcaagg gtgaggagga    58320
taaagcaggt ttccctggca gtaggagcaa gtggactcag caagactgga tctgcacttg    58380
ctctttgtgt tatcaccacc tatgcatgct ctaatccggt gcagtctggt atctgcctcc    58440
tcgaccccac tgaaacattc tcatcaaggt cactagtgtg tgcagcacat tgccattcct    58500
tctccacagc atttgacaca gttgttcact ccctcctcca tgtgtacgtt gggtgctcag    58560
acaccataag cttatagctt tcttttccct ctaatagcaa ctcccttca acctcttttt    58620 ctggttttgc cttttcttc cacctctaaa tatcataggg cctcaaaact caatcctggt    58680
acctctcctg tccttcactg cgttctcttc ctaggtgacc ccatgcagtc ttggggctct    58740
aaatttgacc tctagaatat aaattgctcc tcaatttcag actcagactt acttgtggac    58800
atgcatctcc acttaggtgt ctaatagaca aataaaactc agtaggttc atgagtttca    58860 actgaactct cgaacttgcc cctctccaaa acagctctac ttgtagcctt ccacattgca    58920
gataatgaca ccatccagat atgtgccagt aaagctttaa catctgtcag ggttgaggag    58980
ggtagagaag ctctagattg tagtgtttgc agatttcctt catgtaaata atgctaatat    59040
ttatcaaagt caagctgtca acctgaggtc attgaaccag agtcgggaag aatgctctgg    59100
```

```
agggcagttg tgccctggct cctgccacac ttcagcacta tttacccagc ggctcagctg    59160
acaaaccata gagtcatcat gattttctc ttattcttcc ctcgctttga tacctttcac    59220
aagttcagga aacttgatgt tcaacataat ccctaaatcc cactatttct ctctatccct    59280
ccagtgcaca ctgctgtggc ctctcaccac actactacaa taccttctta tcccagcttc    59340
atgtttctaa tctagccccc atctatcaca tactctctaa ccctgtggcc agaaaattat    59400
gtctgcatgt atatcacatc atgccatgtc gctcctgaaa acctgtcctc aactctcctg    59460
agcactcaga agggaccctg aaccagcttt agtctgcaag actgcacggc tggcctctgt    59520
caccttctcc taacacggga gcccctgggg ctccctctgc tgctgtctcc caaaggcctg    59580
tagatgactt ccccaacacc agcccaatgc tgcttgtttc atttgctcat tgtgcatgta    59640
ctgtctgact gccccatgag gatgtgagct ccacaagggc agggaacgtt gctctggctg    59700
tttactgctg atctccagct cccgacacac tgcctgccac agacgatgaa taatgaaag    59760 aggtgtcaga tctggagtga aaagaaagta cttttctgac acagaaaaga aggattagga    59820
agataataca ctaagaggga ttttggtga tggagtgtgt atagaacttt cagcactaat    59880
ggccgcctct attttctcag aatgtatttg atgtaaagag gaggcaggtt gtggtgtatc    59940
caagttgtct ggcttccagc tcagtaaagc atggcaggtt gtatgtgaat ttgagaaatc    60000
atgaaataaa gtgagacttg ctgttttcaa cttgaaaagc ataacaagct gacactaacg    60060
catgagtacc agggatctgt gaatgtgtgt ttagagttgt actgtcttac ttggtttcca    60120
tatgtattca tagggccaga aaataagagg tggttttatt gtattatgtg tcctggcctc    60180
aatttgaggg gtctcagatc gccacctggt atatcatcct gctttatgag ataatttcct    60240
agaaattgag catcagaggg atatacctgt ggggttgaca taatacccctt acctcacagc    60300 tcaacctctt catttggttt ccagatgcta ctatcattca cgatggccat gaggagaaga    60360
tggaaaatgg tcagatcaca cctgatggct tcctgtcaaa atctgctcca tcagagctta    60420
taaatatgac aggagatgct tatgccaccc aaccaagtgg attctctatc ctgacgactt    60480
cacaagtact cagcaaagat gggctgattc aaaaacctgg tagtaacgca tttgtaggag    60540
gagccaaaaa ctgcagtctc tccgtagatg accaaaaaga cccagtagca tctactttgg    60600
gagctatgcc aaatacatta caaatcactc ctgctatggc acaaggaatc aatgctgata    60660
taaaacatca attaatgaag gaagttcgaa agtttggtcg aagtaagtag tgaaagaaca    60720
tctatcaata atgcaccagg aggtttctct cattctgtga ttcactatag attcaagcta    60780
tcccttgagg tacactgggg gcaatattgg gctttcacat agtttaaggc agttcctctt    60840
gttttaacta aaaaggtaca gtctatattt tcctgttttt tccccttatt tcttgtaatg    60900 tttcctttg ctgccgtaac aagttatcaa aagattccta gcttaaaaca atacaaatta    60960
ttatattaag ttctggaagt cagaattttg aaattatttt tgctgggcca aaatagtgtt    61020
ggcagaccag cattccttct gctagctcta gagagaattt ctttctttgc cttttcgagc    61080
ttctaagggc catctgtatt ccttggccca tggccccttc ctccatcttc atgaaaacac    61140
ccttagcact ttttctcctc tctgacctct gcttctgtct ttacatgttt tctctctgac    61200
cttaactcta ctgtttcatc ttataaggac acttgtgctt acattgggcc cacatgcata    61260
aacttggata atctccccat ctcaagatcc ttaacttaat tacacctgca agtaaagtc    61320 ttttttgcta tataaggtaa tgtattcaca ggttccaggg attaatatgt agacaatttt    61380
aagcagctgc tattcagcct gctacatttg gttagtgtta acaagagttg ccctagtaga    61440
```

-continued

```
tgcatgcaga tattttgata agaatgttaa aatacaaact acatctaact ttccactcac    61500
gaagaacaat tactaaggat gtacaacaat taaattttat ttcccattca tctttataaa    61560
aatactgaag ttttttaaa tatcttcaga atatgaaaga atttcattt tgcttgaaga      61620 agtgcaagga cctctggaga tgaagaaaca gtttgttgaa tttaccatca aggaagccgc    61680
aaggtaggta taaacaggaa ctcttcaatt ttttgttttt gttttagag cagtagggcc     61740 cagtgcagga aaaagagagg aataggctct gccttgcttt tttctcaaac cctggccctc    61800
actcatagtt aaggctgtct ccagaagtat ttggatttat gttatctgaa ctcaactcat    61860
tcatccttct acttttatca tagcctcagg taggcttggg ccctcaattg ccactattgg    61920
tacttgctct aagacatatc tttccatgag acaatcttt atattcctat gtagattgta     61980
agcttcgatt tgtatcccac acagtgcctt gaacatcatg agtactttaa gtatcttttg    62040
gttcataaaa tttctcttta ttttcaggtt taaaagacga gtcctaattc agtaccttga    62100
gaaggtacta gaaaaaataa attcccacca ccttcacaac aacattagtc acatcaacag    62160
cagatcatca tgttagtgca aagaccagtg agaaaaaaat gacaagtttt ctgtgctgta    62220
ggatggaaca ggatattgtt gaagcctcct ggaatgtttg agtcaaggga attgctttcc    62280
agatgctaag aagcagcagt gggcttttt gaatttatg attatctggc agtgaaagct      62340
gggcttttgc cttaataatt ttttaaagta tgaattgttt tgttttgttt tcctcaattg    62400
aggaagctga tgttattaat tcacaggcta aattcggtaa acaccactgc ccctaccacg    62460
ggtaatgaga ggtcactcac ttgaactttg ccattccagg cattctcaga gtggcgaggg    62520
gccacctgca agtggagcac aacttggtgc tcttactgtg tccttcagaa agaataggtg    62580
tacagaaagg aaatggcaat cttatgtgtg ctgaacaaag ttttcaacaa ttcctagttg    62640
tgccttttaa accatgcaat attcaggata gtttgaatca agaagtaag aagctgctat      62700 ttgggtaact tatttctctg tgggaagggg cagggagagt caccaaacaa tctacctcca    62760
actctcttct cttttgtcta gagacattac aaagtgcact tgaggctgcc cccaacctct    62820
gacatttgtt cttgcatgtg atgatagaaa gtcttcagat ggacttatac attctgtgct    62880
ttggaagcac aagaagaaca aaatatgtgt atatttcctt taatgtttat acaaaagttt    62940
atatggagca gtattgttat gtttgtatga atttgcaaaa attaaagtgt acaaagagat    63000
tttgattttg catatataaa ataaatcatt ttattgattt tcacaagttc attaatgctg    63060
gataaatttc tacttatatg tttcttgtga tttgttactc ctttcagaaa aagagtgtat    63120
gctgttaaac aagttaagat gttaacataa ggatttaaac ttcaaaacat cactcacaga    63180
attgagtgac gctagtgaaa aatcacagag tagagtaccc acggactagt cactttcaag    63240
aaacttggaa aacactgggg gaaaaaaaa cctgtcagaa tcaagttta ttggaactct       63300 agaatatagt aaaaggttta cagcaaccaa gccaatcctg aattaggaga gaagtcattg    63360
aaacatggta ggggagcttt gtggcatttc aactcaccct tggaatggct gagtaagaaa    63420
gaaatttgag gccaggtgca gtggcccaca tctgtaatcc cagcactttg ggaggccaag    63480
gtgggaagac cacttgagcc caggagttca agagcagctt gggcaacatg gcgagacccc    63540
atctctccaa aatatatgta tttttaatta gctggacgtg gttgcacaca attgtggtcc    63600
cagctactca ggagactcag gtgggaggac tgctggagcc caggaggtgg aggctgcagt    63660
gaactgtgat cacaccactg aactccagcc tgagcaacag agcaagaccc tgtctcaaat    63720
aataatatat acaagctgac ttctgaaatg gcatggctgc ttacttccca ccttcctacc    63780
cctctcaaac aaagagggag ttttgcatt ttctattcct ggttgcaaaa cacaaggaa       63840
```

```
aatggaaaaa tagtttgtgt gcattcatga tatgcttgct cctttgagac tctcaaacag  63900
ccagcaccat cccttcccat agcctgctag gagccaagat ggcttcccag tgcctgtttc  63960
tcgaccattt taatttaaaa gcatggtgag tagtattagc tgtgccttct ctgccacagg  64020
agagaaagcc tggtcaagag gtgtggtttt ggatgcaata agtccactgc ttcttggaga  64080
cgttcctgga cattcaatcg tgtctttcct gggtccttgg agtagttggt caggatgggc  64140
ttcccactca gtccacgggc ctggggctga ttcatggtgg tcccagagac ctcagccctc  64200
tgtgtttggc tggaagccca gaatggtgta cagttcctca ggcatgagcc ccagcaagtt  64260
ctggacgtca cacaaaaagc agcacatata gcactttccc gacatcttat ggatgatgtt  64320
cttgtcatga tagtaggtaa acccaggctc agcttcttgt agttcatctt gggcttattt  64380
ttcctgattc cccactggca ggcaacattg tcagggttgg caagtttaaa ctcccacctg  64440
tccctattcc agctgatgaa atgactggca agactgtcta aaattccagg aaaaactgct  64500
gtgggtgaat aggtccactt tctgtgaagc cagacagcac agccacaggt ataactggtt  64560
tgccttgctc caccggggttg ctcctctctt ggatgtaatc cttgaaaggc atggtcaact  64620
ttttgaggca gggggactga ctgcagtttt ctttgaagct ctcgaagaaa ggaacctgct  64680
gcacatccag taaggatgac tggttgttcc aggtgcctga gctctcaaag ctgtctgcct  64740
catgatttaa atgttaaaaa agcagacagc tttaaatgtc tgcaccattc tcagggatt   64800 tgtggtcttt aggcttccca gaattgttgg tgagcaaatt caagttgcct agaaagtcct  64860
gactgatgga gcatagttga ggctgataga gctgagctga gacttggaga acatctgaaa  64920
ctcctgttca gagctgagca cgctgggtgc agaagctgga cacatgctgt ccaggaggct  64980
gcctttgggg taattgtgtg tttgcatacc ataggtacc tgctttatgc caaaacctaa   65040
tg                                                                 65042
```

<210> SEQ ID NO 4
<211> LENGTH: 886
<212> TYPE: PRT
<213> ORGANISM: Human

<400> SEQUENCE: 4

Met Pro Ile Leu Leu Phe Leu Ile Asp Thr Ser Ala Ser Met Asn Gln
1               5                   10                  15

Arg Ser His Leu Gly Thr Thr Tyr Leu Asp Thr Ala Lys Gly Ala Val
            20                  25                  30

Glu Thr Phe Met Lys Leu Arg Ala Arg Asp Pro Ala Ser Arg Gly Asp
        35                  40                  45

Arg Tyr Met Leu Val Thr Phe Glu Glu Pro Tyr Ala Ile Lys Ala
    50                  55                  60

Gly Trp Lys Glu Asn His Ala Thr Phe Met Asn Glu Leu Lys Asn Leu
65                  70                  75                  80

Gln Ala Glu Gly Leu Thr Thr Leu Gly Gln Ser Leu Arg Thr Ala Phe
                85                  90                  95

Asp Leu Leu Asn Leu Asn Arg Leu Val Thr Gly Ile Asp Asn Tyr Gly
            100                 105                 110

Gln Gly Arg Asn Pro Phe Phe Leu Glu Pro Ala Ile Ile Ile Thr Ile
        115                 120                 125

Thr Asp Gly Ser Lys Leu Thr Thr Thr Ser Gly Val Gln Asp Glu Leu
    130                 135                 140

His Leu Pro Leu Asn Ser Pro Leu Pro Gly Ser Glu Leu Thr Lys Glu

```
                               -continued 145                 150                 155                 160

Pro Phe Arg Trp Asp Gln Arg Leu Phe Ala Leu Val Leu Arg Leu Pro
                165                 170                 175

Gly Thr Met Ser Val Glu Ser Glu Gln Leu Thr Gly Val Pro Leu Asp
                180                 185                 190

Asp Ser Ala Ile Thr Pro Met Cys Glu Val Thr Gly Arg Ser Tyr
            195                 200                 205

Ser Val Cys Ser Pro Arg Met Leu Asn Gln Cys Leu Glu Ser Leu Val
        210                 215                 220

Gln Lys Val Gln Ser Gly Val Val Ile Asn Phe Glu Lys Ala Gly Pro
225                 230                 235                 240

Asp Pro Ser Pro Val Glu Asp Gly Gln Pro Asp Ile Ser Arg Pro Phe
                245                 250                 255

Gly Ser Gln Pro Trp His Ser Cys His Lys Leu Ile Tyr Val Arg Pro
                260                 265                 270

Asn Pro Lys Thr Gly Val Pro Ile Gly His Trp Pro Val Pro Glu Ser
            275                 280                 285

Phe Trp Pro Asp Gln Asn Ser Pro Thr Leu Pro Pro Arg Thr Ser His
290                 295                 300

Pro Val Val Lys Phe Ser Cys Thr Asp Cys Glu Pro Met Val Ile Asp
305                 310                 315                 320

Lys Leu Pro Phe Asp Lys Tyr Glu Leu Glu Pro Ser Pro Leu Thr Gln
                325                 330                 335

Phe Ile Leu Glu Arg Lys Ser Pro Gln Thr Cys Trp Gln Val Tyr Val
                340                 345                 350

Ser Asn Ser Ala Lys Tyr Ser Glu Leu Gly His Pro Phe Gly Tyr Leu
            355                 360                 365

Lys Ala Ser Thr Ala Leu Asn Cys Val Asn Leu Phe Val Met Pro Tyr
370                 375                 380

Asn Tyr Pro Val Leu Leu Pro Leu Leu Asp Asp Leu Phe Lys Val His
385                 390                 395                 400

Lys Ala Lys Pro Thr Leu Lys Trp Arg Gln Ser Phe Glu Ser Tyr Leu
                405                 410                 415

Lys Thr Met Pro Pro Tyr Tyr Leu Gly Pro Leu Lys Lys Ala Val Arg
                420                 425                 430

Met Met Gly Ala Pro Asn Leu Ile Ala Asp Ser Met Glu Tyr Gly Leu
            435                 440                 445

Ser Tyr Ser Val Ile Ser Tyr Leu Lys Lys Leu Ser Gln Gln Ala Lys
        450                 455                 460

Ile Glu Ser Asp Arg Val Ile Gly Ser Val Gly Lys Lys Val Val Gln
465                 470                 475                 480

Glu Thr Gly Ile Lys Val Arg Ser Arg Ser His Gly Leu Ser Met Ala
                485                 490                 495

Tyr Arg Lys Asp Phe Gln Gln Leu Leu Gln Gly Ile Ser Glu Asp Val
                500                 505                 510

Pro His Arg Leu Leu Asp Leu Asn Met Lys Glu Tyr Thr Gly Phe Gln
            515                 520                 525

Val Ala Leu Leu Asn Lys Asp Leu Lys Pro Gln Thr Phe Arg Asn Ala
        530                 535                 540

Tyr Asp Ile Pro Arg Arg Asn Leu Leu Asp His Leu Thr Arg Met Arg
545                 550                 555                 560

Ser Asn Leu Leu Lys Ser Thr Arg Arg Phe Leu Lys Gly Gln Asp Glu
                565                 570                 575
```

```
Asp Gln Val His Ser Val Pro Ile Ala Gln Met Gly Asn Tyr Gln Glu
            580                 585                 590

Tyr Leu Lys Gln Val Pro Ser Pro Leu Arg Glu Leu Asp Pro Asp Gln
            595                 600                 605

Pro Arg Arg Leu His Thr Phe Gly Asn Pro Phe Lys Leu Asp Lys Lys
            610                 615                 620

Gly Met Met Ile Asp Glu Ala Asp Glu Phe Val Ala Gly Pro Gln Asn
625                 630                 635                 640

Lys His Lys Arg Pro Gly Glu Pro Asn Met Gln Gly Ile Pro Lys Arg
                645                 650                 655

Arg Arg Cys Met Ser Pro Leu Leu Arg Gly Arg Gln Gln Asn Pro Val
            660                 665                 670

Val Asn Asn His Ile Gly Gly Lys Gly Pro Pro Ala Pro Thr Thr Gln
            675                 680                 685

Ala Gln Pro Asp Leu Ile Lys Pro Leu Pro Leu His Lys Ile Ser Glu
            690                 695                 700

Thr Thr Asn Asp Ser Ile Ile His Asp Val Val Glu Asn His Val Ala
705                 710                 715                 720

Asp Gln Leu Ser Ser Asp Ile Thr Pro Asn Ala Met Asp Thr Glu Phe
                725                 730                 735

Ser Ala Ser Ser Pro Ala Ser Leu Leu Glu Arg Pro Thr Asn His Met
            740                 745                 750

Glu Ala Leu Gly His Asp His Leu Gly Thr Asn Asp Leu Thr Val Gly
            755                 760                 765

Gly Phe Leu Glu Asn His Glu Glu Pro Arg Asp Lys Glu Gln Cys Ala
770                 775                 780

Glu Glu Asn Ile Pro Ala Ser Ser Leu Asn Lys Gly Lys Lys Leu Met
785                 790                 795                 800

His Cys Arg Ser His Glu Glu Val Asn Thr Glu Leu Lys Ala Gln Ile
                805                 810                 815

Met Lys Glu Ile Arg Lys Pro Gly Arg Lys Tyr Glu Arg Ile Phe Thr
            820                 825                 830

Leu Leu Lys His Val Gln Gly Ser Leu Gln Thr Arg Leu Ile Phe Leu
            835                 840                 845

Gln Asn Val Ile Lys Glu Ala Ser Arg Phe Lys Lys Arg Met Leu Ile
850                 855                 860

Glu Gln Leu Glu Asn Phe Leu Asp Glu Ile His Arg Arg Ala Asn Gln
865                 870                 875                 880

Ile Asn His Ile Asn Ser
                885

<210> SEQ ID NO 5
<211> LENGTH: 770
<212> TYPE: PRT
<213> ORGANISM: Mus musculus

<400> SEQUENCE: 5

Gly Lys Lys Pro Leu Phe Leu Gly Lys Pro Ala Ile Ile Thr Ile
 1               5                  10                  15

Thr Asp Gly Ser Lys Leu Thr Thr Ser Gly Val Gln Asp Glu Leu
                20                  25                  30

His Leu Pro Leu Asn Ser Pro Leu Ala Gly Ser Glu Leu Thr Lys Glu
            35                  40                  45

Pro Phe Val Gly Ile Arg Asp Tyr Leu Leu Leu Val Leu Arg Leu Pro
```

-continued

```
            50                  55                  60
Gly Thr Met Ser Val Glu Ser Glu Gln Leu Thr Gly Val Pro Leu Asp
 65                  70                  75                  80

Asp Ser Ala Ile Thr Pro Met Cys Glu Val Thr Gly Gly Arg Ser Tyr
                 85                  90                  95

Ser Val Cys Ser Pro Arg Met Leu Asn Gln Cys Leu Glu Ser Leu Val
            100                 105                 110

Gln Lys Val Gln Ser Gly Val Val Ile Asn Phe Glu Lys Ala Gly Pro
        115                 120                 125

Asp Pro Pro Ala Glu Ala Glu Gly Gln Pro Asp Ile Ser Arg Pro
130                 135                 140

Phe Gly Ser Gln Pro Trp His Ser Cys His Lys Leu Ile Tyr Val Arg
145                 150                 155                 160

Pro Asn Pro Lys Thr Gly Val Pro Ile Gly His Trp Pro Val Pro Glu
                165                 170                 175

Ser Phe Trp Pro Asp Gln Asn Ser Pro Thr Leu Pro Pro Arg Thr Ser
                180                 185                 190

His Pro Val Val Lys Phe Ser Cys Thr Asp Cys Glu Pro Met Val Ile
            195                 200                 205

Asp Lys Leu Pro Phe Asp Lys Tyr Glu Leu Glu Pro Ser Pro Leu Thr
210                 215                 220

Gln Tyr Ser Arg Arg Lys Ser Pro Gln Thr Cys Trp Gln Val Tyr Val
225                 230                 235                 240

Ser Asn Ser Ala Lys Tyr Asn Glu Leu Gly His Pro Phe Gly Tyr Leu
                245                 250                 255

Lys Ala Ser Thr Ala Leu Thr Cys Val Asn Leu Phe Val Met Pro Tyr
            260                 265                 270

Asn Tyr Pro Val Leu Leu Pro Leu Leu Asp Asp Leu Phe Lys Val His
            275                 280                 285

Lys Ala Lys Pro Thr Leu Lys Trp Arg Gln Ser Phe Glu Ser Tyr Leu
        290                 295                 300

Lys Thr Met Pro Pro Tyr Tyr Leu Gly Pro Leu Lys Lys Ala Val Arg
305                 310                 315                 320

Met Met Gly Ala Pro Asn Leu Ile Ala Asp Ser Met Glu Tyr Gly Leu
                325                 330                 335

Ser Tyr Ser Val Ile Ser Tyr Leu Lys Lys Leu Ser Gln Gln Ala Lys
            340                 345                 350

Ile Glu Ser Asp Arg Val Ile Gly Ser Val Gly Lys Lys Val Val Gln
        355                 360                 365

Glu Thr Gly Ile Lys Val Arg Ser Arg Ser His Gly Leu Ser Met Ala
        370                 375                 380

His Arg Lys Gly Phe Gln Val Leu Gln Gly Ile Ser Glu Asp Val Pro
385                 390                 395                 400

His Arg Leu Leu Asp Leu Asn Met Lys Glu Tyr Thr Gly Phe Gln Val
                405                 410                 415

Ala Leu Leu Asn Lys Asp Leu Lys Pro Gln Thr Phe Arg Asn Ala Tyr
            420                 425                 430

Asp Ile Pro Arg Arg Asn Leu Leu Asp His Leu Thr Arg Met Arg Ser
            435                 440                 445

Asn Leu Leu Lys Ser Thr Arg Lys Phe Leu Lys Gly Gln Asp Glu Asp
        450                 455                 460

Gln Val His Ser Val Pro Ile Ala Gln Met Gly Asn Tyr Gln Glu Tyr
465                 470                 475                 480
```

-continued

```
Leu Lys Gln Val Pro Ser Pro Leu Arg Glu Leu Asp Pro Asp Gln Pro
            485                 490                 495
Arg Arg Leu His Thr Phe Gly Asn Pro Phe Lys Leu Asp Lys Lys Gly
            500                 505                 510
Met Met Ile Asp Glu Ala Asp Glu Phe Val Ala Gly Pro Gln Asn Lys
            515                 520                 525
His Lys Arg Pro Gly Glu Pro Ser Met Gln Gly Ile Pro Lys Arg Arg
    530                 535                 540
Arg Cys Ala Ser Pro Leu Leu Arg Gly Arg Arg Gln Ser Pro Ala Val
545                 550                 555                 560
Asn Ser His Ile Gly Gly Lys Gly Pro Pro Ala Pro Met Thr Gln Ala
            565                 570                 575
Gln Pro Gly Leu Ile Lys Pro Leu Pro Leu His Lys Glu Ala Thr Asn
            580                 585                 590
Asp Ser Ile Val Asp Asp Val Val Glu Asn His Val Ala Asp Gln Leu
            595                 600                 605
Ser Ser Asp Met Thr Pro Asn Ala Met Asp Thr Glu Phe Leu Thr Ser
    610                 615                 620
Pro Pro Asn Leu Leu Glu Pro Ser Thr Asn His Thr Glu Ala Leu Gly
625                 630                 635                 640
His Glu His Leu Gly Asn Asn Asp Leu Thr Val Gly Gly Phe Leu Glu
            645                 650                 655
Asn His Glu Glu Pro Arg Asn Lys Glu Gln Ser Ala Glu Glu Asn Ile
            660                 665                 670
Pro Ala Ser Ser Leu Asn Lys Gly Lys Lys Leu Met His Cys Arg Ser
            675                 680                 685
His Glu Glu Val Asn Thr Glu Leu Lys Ala Gln Ile Met Lys Glu Ile
    690                 695                 700
Arg Lys Pro Gly Arg Lys Tyr Glu Arg Ile Phe Thr Leu Leu Lys His
705                 710                 715                 720
Val Gln Gly Ser Leu Gln Thr Arg Leu Ile Phe Leu Gln Asn Val Ile
            725                 730                 735
Lys Glu Ala Ser Arg Phe Lys Lys Arg Met Leu Ile Glu Gln Leu Glu
            740                 745                 750
Asn Phe Leu Asp Glu Ile His Arg Arg Ala Asn Gln Ile Asn His Ile
            755                 760                 765
Asn Ser
    770
```